US012661437B2

(12) United States Patent (10) Patent No.: US 12,661,437 B2
Shelton, IV et al. (45) Date of Patent: Jun. 23, 2026

(54) THORACIC POST-SURGICAL MONITORING AND COMPLICATION PREDICTION

(71) Applicant: Cilag GmbH International, Zug (CH)

(72) Inventors: Frederick E. Shelton, IV, Hillsboro, OH (US); Jason L. Harris, Lebanon, OH (US); Chad Edward Eckert, Terrace Park, OH (US); Demetrius Harris, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 1393 days.

(21) Appl. No.: 17/156,272

(22) Filed: Jan. 22, 2021

(65) Prior Publication Data

US 2022/0241474 A1 Aug. 4, 2022

(51) Int. Cl.
    *A61M 1/04*     (2006.01)
    *A61B 5/00*     (2006.01)
    (Continued)

(52) U.S. Cl.
    CPC ............. *A61M 1/04* (2013.01); *A61B 5/0205* (2013.01); *A61B 5/4836* (2013.01); *A61B 5/486* (2013.01);
    (Continued)

(58) Field of Classification Search
None
See application file for complete search history.

(56) References Cited

U.S. PATENT DOCUMENTS 5,406,914 A    4/1995   Hyppanen
5,494,546 A    2/1996   Horvath
(Continued)

FOREIGN PATENT DOCUMENTS

CA    3032139 A1   2/2018
CA    3080325 A1   5/2019
(Continued)

OTHER PUBLICATIONS

Johnston et al.—Postoperative Hypoglycemia Is Associated With Worse Outcomes After Cardiac Surgery Ann Thorac Surg. Feb. 2017 ; 103(2): 526-532. (Year: 2017).*
(Continued)

*Primary Examiner* — Jay B Shah
(74) *Attorney, Agent, or Firm* — Condo Roccia Koptiw

(57) ABSTRACT

Patient biomarkers may be monitored before, during, and/or after thoracic surgery to predict complications, detect complications, track recovery, and/or make pre-, in- and/or post-surgery recommendations to avoid predicted complications and/or mitigate detected complications. Complications (e.g., prolonged air leak or esophageal stricture) may be predicted based on patient parameters and/or biomarker measurements. Complications may be predicted or detected based on biomarker measurements compared to thresholds associated with a biomarker (e.g., developed from baselines) generated based on patient parameters, pre- and/or in-surgery biomarker measurements, and/or surgical details (e.g., decrease in long capacity). Recovery milestones may be tracked based on biomarker measurements compared to predicted biomarker measurements for recovery stages. A recommendation (e.g., to avoid a predicted complication and/or mitigate a detected complication) may be a patient-specific selection and/or modification of more of: surgical preparation, in-surgery procedures, surgical instrument selection, surgical and/or post-surgical instrument settings, post-surgery procedures, in-surgery and/or post-surgery monitoring, etc.

20 Claims, 35 Drawing Sheets

(51) Int. Cl.

| | |
|---|---|
| *A61B 5/0205* | (2006.01) |
| *A61B 5/021* | (2006.01) |
| *A61B 5/024* | (2006.01) |
| *A61B 5/08* | (2006.01) |
| *A61B 5/091* | (2006.01) |
| *A61B 5/145* | (2006.01) |
| *A61M 1/00* | (2006.01) |

(52) U.S. Cl.
CPC ............ *A61B 5/7275* (2013.01); *A61B 5/742* (2013.01); *A61M 1/74* (2021.05); *A61B 5/021* (2013.01); *A61B 5/024* (2013.01); *A61B 5/0816* (2013.01); *A61B 5/091* (2013.01); *A61B 5/14542* (2013.01); *A61B 2560/0242* (2013.01); *A61M 2205/3303* (2013.01)

(56) References Cited

U.S. PATENT DOCUMENTS

| | | | |
|---|---|---|---|
| 6,036,446 A | 3/2000 | Goodman | |
| 6,317,731 B1 | 11/2001 | Luciano | |
| 6,491,701 B2 | 12/2002 | Tierney et al. | |
| 6,840,913 B2 | 1/2005 | Mansy et al. | |
| 7,321,862 B2 | 1/2008 | Rosenfeld et al. | |
| 8,417,342 B1 | 4/2013 | Abell | |
| 8,512,260 B2 | 8/2013 | Grudic et al. | |
| 8,583,224 B2 | 11/2013 | Lee et al. | |
| 8,696,616 B2 | 4/2014 | Baynham et al. | |
| 8,864,009 B2 | 10/2014 | Shelton et al. | |
| 9,011,427 B2 | 4/2015 | Price et al. | |
| 9,028,407 B1 | 5/2015 | Bennett-Guerrero | |
| 9,072,535 B2 | 7/2015 | Shelton et al. | |
| 9,123,155 B2 | 9/2015 | Cunningham et al. | |
| 9,345,481 B2 | 5/2016 | Hall et al. | |
| 9,525,482 B1 | 12/2016 | Tse | |
| 9,621,357 B2 | 4/2017 | Williams et al. | |
| 9,700,317 B2 | 7/2017 | Aronhalt et al. | |
| 9,855,431 B2 | 1/2018 | Ternes et al. | |
| 9,974,903 B1 | 5/2018 | Davis et al. | |
| 10,194,873 B2 | 2/2019 | Colman et al. | |
| 10,467,327 B1 | 11/2019 | Arazi | |
| 10,535,020 B2 | 1/2020 | Experton | |
| 10,813,710 B2 | 10/2020 | Grubbs | |
| 10,943,692 B1 | 3/2021 | Lynn et al. | |
| 10,993,645 B2 | 5/2021 | Naseri et al. | |
| 11,182,576 B1 | 11/2021 | Bhushan et al. | |
| 11,238,012 B1 | 2/2022 | Liang et al. | |
| 11,240,404 B2 | 2/2022 | Bangs et al. | |
| 2002/0111830 A1 | 8/2002 | Tahan | |
| 2003/0139942 A1 | 7/2003 | Rakshit et al. | |
| 2005/0021369 A1 | 1/2005 | Cohen et al. | |
| 2006/0085227 A1 | 4/2006 | Rosenfeld et al. | |
| 2008/0064965 A1 | 3/2008 | Jay et al. | |
| 2008/0300915 A1 | 12/2008 | Molmenti et al. | |
| 2009/0299924 A1 | 12/2009 | Bauer et al. | |
| 2010/0228314 A1 | 9/2010 | Goetz | |
| 2011/0054290 A1 | 3/2011 | Derchak | |
| 2011/0152759 A1 | 6/2011 | Clymer et al. | |
| 2011/0172504 A1* | 7/2011 | Wegerich ............ | A61B 5/6898 600/301 |
| 2011/0319746 A1 | 12/2011 | Kochba et al. | |
| 2012/0116365 A1 | 5/2012 | Price et al. | |
| 2012/0132211 A1 | 5/2012 | Halperin et al. | |
| 2012/0259389 A1 | 10/2012 | Starkebaum et al. | |
| 2012/0265549 A1 | 10/2012 | Virolainen | |
| 2012/0310670 A1 | 12/2012 | Pruitt | |
| 2013/0038707 A1 | 2/2013 | Cunningham et al. | |
| 2013/0137941 A1 | 5/2013 | Schardey | |
| 2013/0245481 A1 | 9/2013 | Tremper | |
| 2013/0265919 A1 | 10/2013 | Pochiraju et al. | |
| 2014/0051921 A1 | 2/2014 | Miller et al. | |
| 2014/0081659 A1 | 3/2014 | Nawana et al. | |
| 2014/0157288 A1 | 6/2014 | Wong | |
| 2014/0236159 A1 | 8/2014 | Haider et al. | |
| 2014/0263541 A1 | 9/2014 | Leimbach et al. | |
| 2014/0263551 A1 | 9/2014 | Hall et al. | |
| 2014/0263552 A1 | 9/2014 | Hall et al. | |
| 2014/0287393 A1 | 9/2014 | Kumar et al. | |
| 2015/0126839 A1 | 5/2015 | Li et al. | |
| 2015/0173674 A1* | 6/2015 | Hayes ................... | G16H 40/67 600/300 |
| 2015/0173697 A1 | 6/2015 | Parks et al. | |
| 2015/0199010 A1 | 7/2015 | Coleman et al. | |
| 2015/0250445 A1 | 9/2015 | Spiegel et al. | |
| 2015/0289929 A1 | 10/2015 | Toth et al. | |
| 2015/0302536 A1 | 10/2015 | Wahl et al. | |
| 2015/0302538 A1 | 10/2015 | Mazar et al. | |
| 2015/0302539 A1 | 10/2015 | Mazar et al. | |
| 2015/0317230 A1 | 11/2015 | Le Grand | |
| 2016/0030240 A1 | 2/2016 | Gonenc et al. | |
| 2016/0110504 A1 | 4/2016 | Fialkov | |
| 2016/0239611 A1 | 8/2016 | Heldt et al. | |
| 2016/0287184 A1* | 10/2016 | Diebold .............. | A61B 5/7475 |
| 2016/0303340 A1 | 10/2016 | Sinderby et al. | |
| 2016/0331248 A1 | 11/2016 | Satish et al. | |
| 2017/0041688 A1 | 2/2017 | Pitigoi-aron et al. | |
| 2017/0068785 A1 | 3/2017 | Experton et al. | |
| 2017/0119300 A1 | 5/2017 | Conner | |
| 2017/0143268 A1 | 5/2017 | Kovacs et al. | |
| 2017/0228501 A1 | 8/2017 | Turner, Jr. et al. | |
| 2017/0258408 A1 | 9/2017 | Stapelfeldt | |
| 2017/0281064 A1 | 10/2017 | Bayon | |
| 2017/0296139 A1 | 10/2017 | Giaya et al. | |
| 2017/0296213 A1 | 10/2017 | Swensgard et al. | |
| 2017/0326190 A1 | 11/2017 | Ansell et al. | |
| 2017/0331881 A1 | 11/2017 | Chandramouli et al. | |
| 2017/0360358 A1 | 12/2017 | Amiot et al. | |
| 2018/0028088 A1 | 2/2018 | Garbey et al. | |
| 2018/0042681 A1 | 2/2018 | Jagga | |
| 2018/0090029 A1 | 3/2018 | Fisher et al. | |
| 2018/0102960 A1 | 4/2018 | Rickert et al. | |
| 2018/0168579 A1 | 6/2018 | Aronhalt et al. | |
| 2018/0256051 A1 | 9/2018 | Stone et al. | |
| 2018/0262656 A1 | 9/2018 | Uchida et al. | |
| 2018/0286521 A1 | 10/2018 | Fong | |
| 2018/0353112 A1* | 12/2018 | Dassau ................. | G16H 50/30 |
| 2018/0360451 A1 | 12/2018 | Shelton, IV et al. | |
| 2018/0360452 A1 | 12/2018 | Shelton et al. | |
| 2019/0013099 A1 | 1/2019 | Esterberg et al. | |
| 2019/0014992 A1 | 1/2019 | Mestek et al. | |
| 2019/0059932 A1 | 2/2019 | Isosaki et al. | |
| 2019/0076380 A1 | 3/2019 | Baron et al. | |
| 2019/0079916 A1 | 3/2019 | Eyigoz | |
| 2019/0104919 A1 | 4/2019 | Shelton, IV et al. | |
| 2019/0113973 A1 | 4/2019 | Coleman et al. | |
| 2019/0190635 A1 | 6/2019 | Goel et al. | |
| 2019/0192072 A1 | 6/2019 | Bailey et al. | |
| 2019/0200844 A1 | 7/2019 | Shelton et al. | |
| 2019/0200981 A1 | 7/2019 | Harris et al. | |
| 2019/0201033 A1 | 7/2019 | Yates et al. | |
| 2019/0201043 A1 | 7/2019 | Shelton, IV et al. | |
| 2019/0201102 A1 | 7/2019 | Shelton, IV et al. | |
| 2019/0201104 A1 | 7/2019 | Shelton, IV et al. | |
| 2019/0201115 A1 | 7/2019 | Shelton, IV et al. | |
| 2019/0201129 A1 | 7/2019 | Shelton, IV et al. | |
| 2019/0201136 A1 | 7/2019 | Shelton, IV et al. | |
| 2019/0201137 A1 | 7/2019 | Shelton et al. | |
| 2019/0201140 A1 | 7/2019 | Yates et al. | |
| 2019/0204201 A1 | 7/2019 | Shelton, IV et al. | |
| 2019/0206050 A1 | 7/2019 | Yates et al. | |
| 2019/0206562 A1 | 7/2019 | Shelton, IV et al. | |
| 2019/0206563 A1 | 7/2019 | Shelton, IV et al. | |
| 2019/0206569 A1 | 7/2019 | Shelton et al. | |
| 2019/0216452 A1 | 7/2019 | Nawana et al. | |
| 2019/0223961 A1 | 7/2019 | Barral et al. | |
| 2019/0258672 A1 | 8/2019 | Sadrieh | |
| 2019/0259476 A1 | 8/2019 | Armijos | |
| 2019/0392162 A1 | 12/2019 | Stern et al. | |
| 2020/0022593 A1 | 1/2020 | Schardey | |
| 2020/0107781 A1 | 4/2020 | Navalgund et al. | |
| 2020/0131581 A1 | 4/2020 | Jain et al. | |
| 2020/0143594 A1 | 5/2020 | Lal et al. | |
| 2020/0168313 A1 | 5/2020 | Westerhoff | |

(56)　　　　　References Cited

U.S. PATENT DOCUMENTS

| | | | |
|---|---|---|---|
| 2020/0168334 A1 | 5/2020 | Mowery |
| 2020/0184850 A1 | 6/2020 | Pugh |
| 2020/0188028 A1 | 6/2020 | Feiner et al. |
| 2020/0204631 A1 | 6/2020 | Subramaniam et al. |
| 2020/0237452 A1 | 7/2020 | Wolf et al. |
| 2020/0246081 A1 | 8/2020 | Johnson et al. |
| 2020/0268472 A1 | 8/2020 | Wolf et al. |
| 2020/0273575 A1 | 8/2020 | Wolf et al. |
| 2020/0273581 A1 | 8/2020 | Wolf et al. |
| 2020/0297422 A1 | 9/2020 | Gocho et al. |
| 2020/0315454 A1 | 10/2020 | Gregg |
| 2020/0315734 A1 | 10/2020 | El Amm |
| 2020/0394334 A1 | 12/2020 | Bulut et al. |
| 2020/0397515 A1 | 12/2020 | Frimer et al. |
| 2021/0000347 A1 | 1/2021 | Stump |
| 2021/0000558 A1 | 1/2021 | Penny et al. |
| 2021/0005321 A1 | 1/2021 | Hwang |
| 2021/0007774 A1 | 1/2021 | Rodrigues et al. |
| 2021/0015432 A1 | 1/2021 | Konno et al. |
| 2021/0069513 A1 | 3/2021 | Beer et al. |
| 2021/0098088 A1 | 4/2021 | Hashimoto et al. |
| 2021/0117868 A1 | 4/2021 | Sriharsha |
| 2021/0158955 A1 | 5/2021 | Azizian et al. |
| 2021/0196384 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0241869 A1 | 8/2021 | Muse et al. |
| 2021/0257095 A1 | 8/2021 | Zacharia |
| 2021/0346583 A1 | 11/2021 | Diaz-chiosa et al. |
| 2021/0346853 A1 | 11/2021 | Hull et al. |
| 2021/0386489 A1 | 12/2021 | Wright et al. |
| 2022/0104896 A1 | 4/2022 | Shelton, IV et al. |
| 2022/0409285 A1 | 12/2022 | Chow et al. |
| 2024/0099647 A1 | 3/2024 | Pelssers et al. |

FOREIGN PATENT DOCUMENTS

| | | | |
|---|---|---|---|
| CA | 3101092 A1 | 10/2019 |
| CN | 109575143 A | 4/2019 |
| CN | 111616803 A | 9/2020 |
| CN | 112220562 A | 1/2021 |
| EP | 3501459 A2 | 6/2019 |
| EP | 3671759 A1 | 6/2020 |
| EP | 3895613 A1 | 10/2021 |
| JP | 2019-525276 A | 9/2019 |
| JP | 2019-177134 A | 10/2019 |
| WO | 2007/096931 A2 | 8/2007 |
| WO | 2010017192 A1 | 2/2010 |
| WO | 2016/046634 A1 | 3/2016 |
| WO | 2017/098503 A1 | 6/2017 |
| WO | 2017/147652 A1 | 9/2017 |
| WO | 2018023037 A1 | 2/2018 |
| WO | 2019084469 A1 | 5/2019 |
| WO | 2019130085 A1 | 7/2019 |
| WO | 2019147718 A1 | 8/2019 |
| WO | 2019181432 A1 | 9/2019 |
| WO | 2019200222 A1 | 10/2019 |
| WO | 2020075546 A1 | 4/2020 |
| WO | 2020/092701 A2 | 5/2020 |
| WO | 2020/180917 A1 | 9/2020 |
| WO | 2020/191494 A1 | 10/2020 |
| WO | 2021/007418 A2 | 1/2021 |
| WO | 2021/126163 A1 | 6/2021 |

OTHER PUBLICATIONS

McGillion et al. Postoperative Remote Automated Monitoring and Virtual Hospital-to-Home Care System Following Cardiac and Major Vascular Surgery: User Testing Study—J Med Internet Res 2020 | vol. 22 | iss. 3 | e15548 | p. 1 (Year: 2020).*

Ewenighi, Chinwe O. et al., "Electrolyte changes and urinalysis pattern in patients with vesicovaginal fistula compared to their healthy controls", Journal of Experimental and Integrative Medicine; Oct.-Dec. 2014; vol. 4., Issue 4, 2014, 5 pages.

Szarka, Lawrence A. et al., "Methods for measurement of gastric mobility", American Journal of Physiology-Gastrointestinal and Liver Physiology 296.3, Jan. 15, 2009, 15 pages.

Appelboom et al., "The Promise of Wearable Activity Sensors to Define Patient Recovery", Journal of Clinical Neuroscience, vol. 21, 2014, pp. 1089-1093.

Chen et al., "Type of Pelvic Disease as a Risk Factor for Surgical Site Infection in Women Undergoing Hysterectomy", Journal of Minimally Invasive Gynecology, vol. 26, No. 6, Sep. 1, 2019, pp. 1149-1156.

Erowele et al., "Treatment Options for Postoperative Ileus", U.S. Pharmacist, vol. 35, No. 12, 2010, 16 pages.

Fang et al., "Review of Colonic Anastomotic Leakage and Prevention Methods", Journal of Clinical Medicine, vol. 9, No. 4061, Dec. 16, 2020, 17 pages.

Jinbin, "Feedback Loops—Friend or Foe?", Available at <https://medium.com/unpackai/feedback-loops-friend-or-foe-81a552203228>, Oct. 19, 2020, pp. 1-3.

Li et al., "Attention-Aware Robotic Laparoscope for Human-Robot Cooperative Surgery", IEEE International Conference on Robotics and Biomimetics (ROBIO), 2013, 6 pages.

Machado, Lovina S. M., Emergency Peripartum Hysterectomy: Incidence, Indications, Risk Factors and Outcome, North American Journal of Medical Sciences, vol. 3, No. 8, Aug. 2011, doi: 10.4297/najms.2011.358, pp. 358-361.

Sugino et al., "Surgical Task Analysis of Simulated Laparoscopic Cholecystectomy with a Navigation System", International Journal of Computer Assisted Radiology and Surgery, vol. 9, Jan. 14, 2014, pp. 825-836.

Clarke-Pearson, et al., "Complications of Hysterectomy", Clinical Expert Series, vol. 121, No. 3, Mar. 2013, pp. 654-673.

Derbyshire, et al., "Lactate in Human Sweat: A Critical Review of Research to the Present Day", Journal of Physiotherapy, vol. 62, Jun. 8, 2012, pp. 429-440.

U.S. Appl. No. 17/156,287, filed Jan. 22, 2021, Shelton, et al.
U.S. Appl. No. 17/156,296, filed Jan. 22, 2021, Shelton, et al.
U.S. Appl. No. 17/156,300, filed Jan. 22, 2021, Shelton, et al.
U.S. Appl. No. 17/156,266, filed Jan. 22, 2021, Shelton, et al.
U.S. Appl. No. 17/156,304, filed Jan. 22, 2021, Shelton, et al.
U.S. Appl. No. 17/156,318, filed Jan. 22, 2021, Shelton, et al.
U.S. Appl. No. 17/156,309, filed Jan. 22, 2021, Shelton, et al.
U.S. Appl. No. 17/156,306, filed Jan. 22, 2021, Shelton, et al.
U.S. Appl. No. 17/156,321, filed Jan. 22, 2021, Shelton, et al.
U.S. Appl. No. 17/156,281, filed Jan. 22, 2021, Shelton, et al.
U.S. Appl. No. 17/156,279, filed Jan. 22, 2021, Shelton, et al.
U.S. Appl. No. 17/156,284, filed Jan. 22, 2021, Shelton, et al.
U.S. Appl. No. 17/156,282, filed Jan. 22, 2021, Shelton, et al.
U.S. Appl. No. 17/156,269, filed Jan. 22, 2021, Shelton, et al.
U.S. Appl. No. 17/156,286, filed Jan. 22, 2021, Shelton, et al.
U.S. Appl. No. 17/156,324, filed Jan. 22, 2021, Shelton, et al.
U.S. Appl. No. 17/156,329, filed Jan. 22, 2021, Shelton, et al.
U.S. Appl. No. 17/156,289, filed Jan. 22, 2021, Shelton, et al.
U.S. Appl. No. 17/156,293, filed Jan. 22, 2021, Shelton, et al.
U.S. Appl. No. 17/156,298, filed Jan. 22, 2021, Shelton, et al.
U.S. Appl. No. 17/156,274, filed Jan. 22, 2021, Shelton, et al.
U.S. Appl. No. 17/156,278, filed Jan. 22, 2021, Shelton, et al.
U.S. Appl. No. 17/062,509, filed Oct. 2, 2020, Shelton, et al.
U.S. Appl. No. 62/611,341, filed Dec. 28, 2017, Shelton, et al.

Aliverti, et al., "Wearable technology: role in respiratory health and disease", Breathe, 2017, 10 pages.

Kazamias, et al., "Blood pressure measurement with Doppler ultrasonic flowmeter", Journal of Applied Physiology vol. 30, No. 4, Apr. 1971, 1 page.

Cerfolio, et a., "Prospective Randomized Trial Compares Suction Versus Water Seal for Air Leaks", General Thoracic, May 1, 2001, 5 pages.

Brunelli, et al., "A Scoring System to Predict the Risk of Prolonged Air Leak After Lobectomy", General Thoracic, 2010, 6 pages.

Jacob, et al., "Clinical applications of magnets on cardiac rhythm management devices", European Society of Cardiology, May 26, 2011, 9 pages.

(56)                References Cited

OTHER PUBLICATIONS

Carroll, et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe", Journal of Cardiovascular Electrophysiology vol. 24, No. 9, Sep. 2013, 8 pages.

Singh, et al., "Esophageal Injury and Temperature Monitoring During Atrial Fibrillation Ablation", American Heart Association, Circulation: Arrhythmia and Electrophysiology, vol. 1, issue 3, Aug. 1, 2008, 7 pages.

Nair, et al., "Atrioesophageal Fistula: A Review", Journal of Atrial Fibrillation vol. 8, Issue 3, October Nov. 2015, 6 pages.

Drewry, et al., "Body temperature patterns as a predictor of hospital-acquired sepsis in afebrile adult intensive care unit patients: a case-control study", Critical Care 2013, 11 pages.

Diduch, et al., "Synchronization of Data Streams in Distributed Realtime Multimodal Signal Processing Environments Using Commodity Hardware", 4 pages.

Kwon, et al., "Electrocardiogram Sampling Frequency Range Acceptable for Heart Rate Variability Analysis", The Korean Society of Medical Informatics, 2018, 9 pages.

Pouchard, et al., "Open Standards for Sensor Information Processing", Oak Ridge National Laboratory, Jul. 2009, 49 pages.

Gill, et al., "Urinary Leakage following hysterectomy", Cambridge University Press, 2014, pp. 261-262.

"International Search Report and Written Opinion, received for PCT Application No. PCT/IB2022/050508", Mar. 24, 2022, 15 pages.

"International Search Report and Written Opinion, received for PCT Application No. PCT/IB2022/050511", Mar. 25, 2022, 17 pages.

"International Search Report and Written Opinion, received for PCT Application No. PCT/IB2022/050513", Mar. 25, 2022, 16 pages.

"International Search Report and Written Opinion, received for PCT Application No. PCT/IB2022/050515", May 17, 2022, 13 pages.

"International Search Report and Written Opinion, received for PCT Application No. PCT/IB2022/050518", Mar. 25, 2022, 12 pages.

"International Search Report and Written Opinion, received for PCT Application No. PCT/IB2022/050522", May 2, 2022, 17 pages.

"International Search Report and Written Opinion, received for PCT Application No. PCT/IB2022/050524", Apr. 21, 2022, 16 pages.

"International Search Report and Written Opinion, received for PCT Application No. PCT/IB2022/050525", May 4, 2022, 12 pages.

"International Search Report and Written Opinion, received for PCT Application No. PCT/IB2022/050529", Apr. 20, 2022, 9 pages.

"International Search Report and Written Opinion, received for PCT Application No. PCT/IB2022/050531", Apr. 13, 2022, 9 pages.

"International Search Report and Written Opinion, received for PCT Application No. PCT/IB2022/050533", Apr. 13, 2022, 11 pages.

"International Search Report and Written Opinion, received for PCT Application No. PCT/IB2022/050534", Apr. 22, 2022, 12 pages.

"International Search Report and Written Opinion, received for PCT Application No. PCT/IB2022/050537", Apr. 7, 2022, 12 pages.

"International Search Report and Written Opinion, received for PCT Application No. PCT/IB2022/050541", Jul. 26, 2022, 16 pages.

"International Search Report and Written Opinion, received for PCT Application No. PCT/IB2022/050542", May 2, 2022, 13 pages.

"International Search Report and Written Opinion, received for PCT Application No. PCT/IB2022/050543", Apr. 22, 2022, 17 pages.

"International Search Report and Written Opinion, received for PCT Application No. PCT/IB2022/050544", Apr. 28, 2022, 17 pages.

Davies, et al., "Preoperative Optimization of the High-Risk Surgical Patient", British Journal of Anaesthesia, vol. 93, Advance Access publication, Apr. 30, 2004, pp. 121-128.

Foroutan, et al., "An increase in heart rate variability can be an index for end point of resuscitation in trauma patients", Chinese Journal of Traumatology 22, vol. 22, No. 3, Apr. 16, 2019, pp. 134-137.

Gehrich, et al., "Risk of postoperative urinary tract infections following midurethral sling operations in women undergoing hysterectomy", International Urogynecology Journal, vol. 27, No. 3, Oct. 14, 2015, pp. 483-490.

Kirchhoff, et al., "Complications in Colorectal Surgery: Risk Factors and Preventive Strategies", Patient Safety in vol. 04, Mar. 25, 2010, 13 pages.

Levine, et al., "Computer Automated Total Perioperative Situational Awareness and Safety System", Computer Assisted Radiology and Surgery, International Series, vol. 1281, Jun. 2005, 6 pages.

Macefield, et al., "Development of a Single, Practical Measure of Surgical Site Infection (SSI) for Patient Report or Completion", Journal of Infection Prevention, vol. 18, No. 4, 2017, pp. 170-179.

Petrella, et al., "Predicting Prolonged Air Leak After Standard Pulmonary Lobectomy: Computed Tomography and Risk Factors Stratification", The Surgeon, vol. 9, 2011, pp. 72-77.

Schug, et al., "Postoperative Pain Management of the Obese Patient", Best Practice & Research Clinical vol. 25, No. 1, 2011, pp. 73-81.

Stoppelkamp, et al., "Identification of Predictive Early Biomarkers for Sterile-SIRS after Cardiovascular Surgery", PLOS vol. 10, No. 8, Aug. 11, 2015, 20 pages.

Veličković, V. J. "The Predictive Performance of the Possum Scoring System and Early Indicators of Peripheral Perfusion for Complications After Major Abdominal Surgery", University of Belgrade, School of Medicine, 2019, pp. 1-163.

* cited by examiner

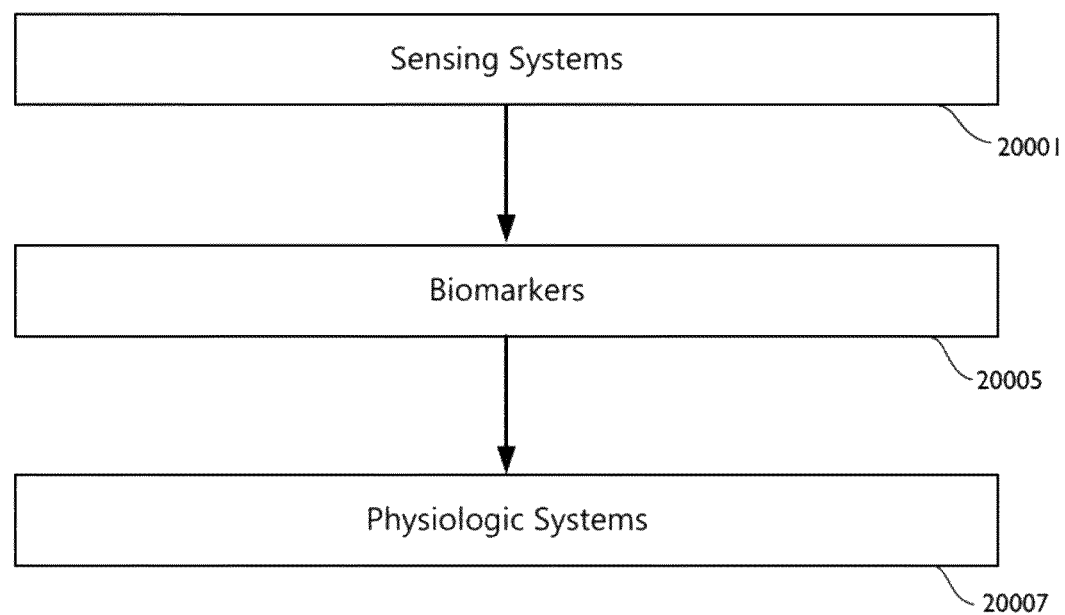
FIG. 1B

Computing System (e.g., surgical hub) 25258

Mobile device 25260

25270

25257

25252

25253

25274

25259

25256

25300

| Procedural Step | Effected Outcome | Potential Instruments Used During Procedural Step | Relevant Patient Biomarkers |
|---|---|---|---|
| Dissect parenchyma | • Homeostasis | • Monopolar Bovie<br>• Harmonic scalpel<br>• Advanced Bipolar RF | • Blood Pressure |
| Transect Arteries and Veins | • Homeostasis | • Harmonic scalpel<br>• Advanced Bipolar RF<br>• Staplers | • Blood Pressure<br>• Tissue perfusion pressure<br>• Edema<br>• Arterial stiffness<br>• Collagen content<br>• Thickness of connective tissue |
| Parenchyma transection | • Pneumostasis | • Staplers | • Edema<br>• Lung tissue thickness<br>• Lung tissue viscoelastic properties<br>• Lung tissue scarring/fibrous characterization |
| Lymph Node Dissection | • Homeostasis | • Monopolar Bovie<br>• Harmonic scalpel<br>• Advanced Bipolar RF | • Blood Pressure<br>• Edema<br>• Tissue Perfusion Pressure<br>• Urinary Tract Imaging |

25311 — receive measurement data from at least one sensing system, wherein the measurement data is associated with a set of patient biomarkers 25312 — predict or detect an occurrence of a prolonged air leak (PAL) based at least on the measurement data associated with the set of patient biomarkers 25313 — generate a set of recommendations for preventing the PAL

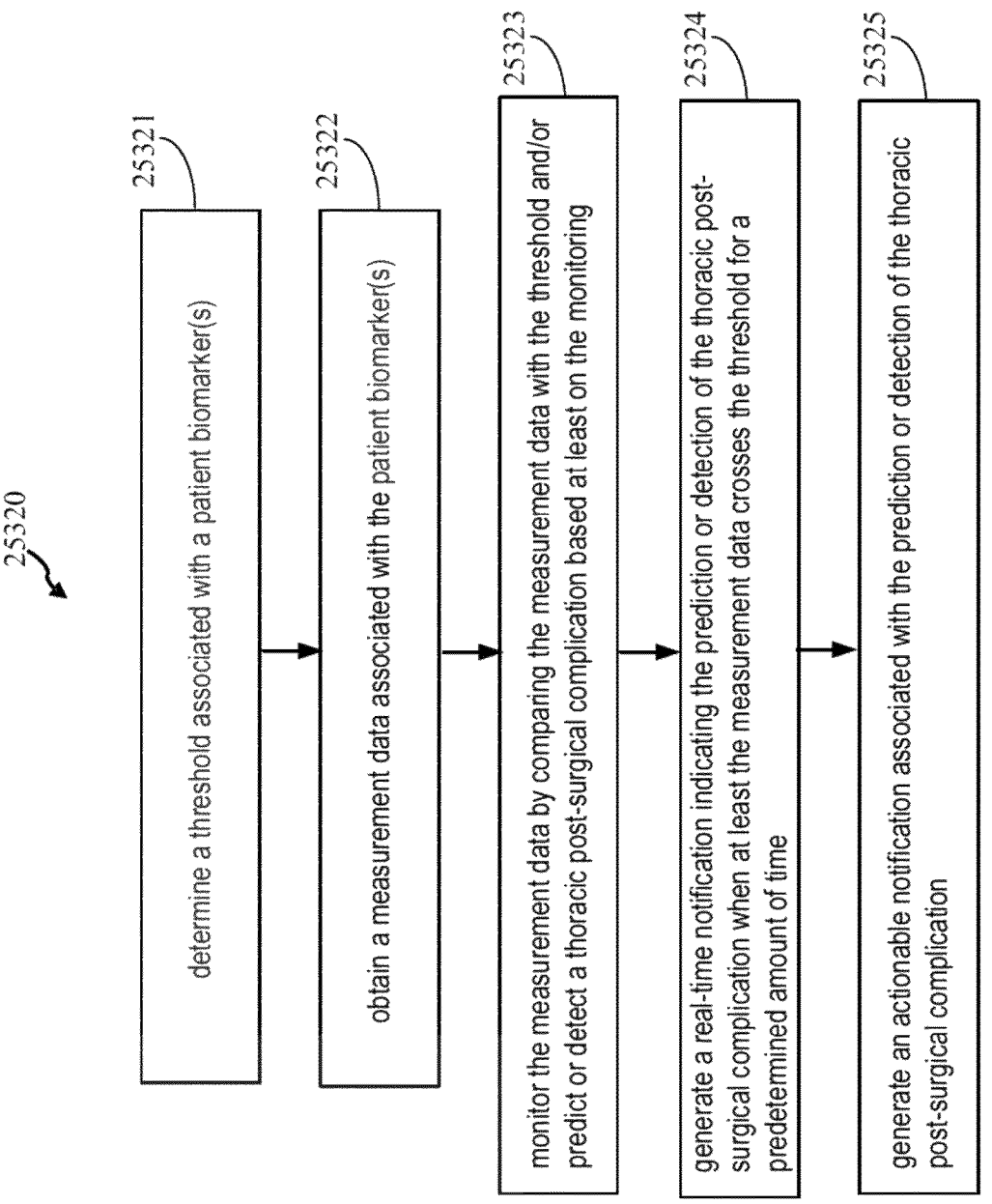

25320

25321 determine a threshold associated with a patient biomarker(s)

25322 obtain a measurement data associated with the patient biomarker(s)

25323 monitor the measurement data by comparing the measurement data with the threshold and/or predict or detect a thoracic post-surgical complication based at least on the monitoring 25324 generate a real-time notification indicating the prediction or detection of the thoracic post-surgical complication when at least the measurement data crosses the threshold for a predetermined amount of time 25325 generate an actionable notification associated with the prediction or detection of the thoracic post-surgical complication

FIG. 20

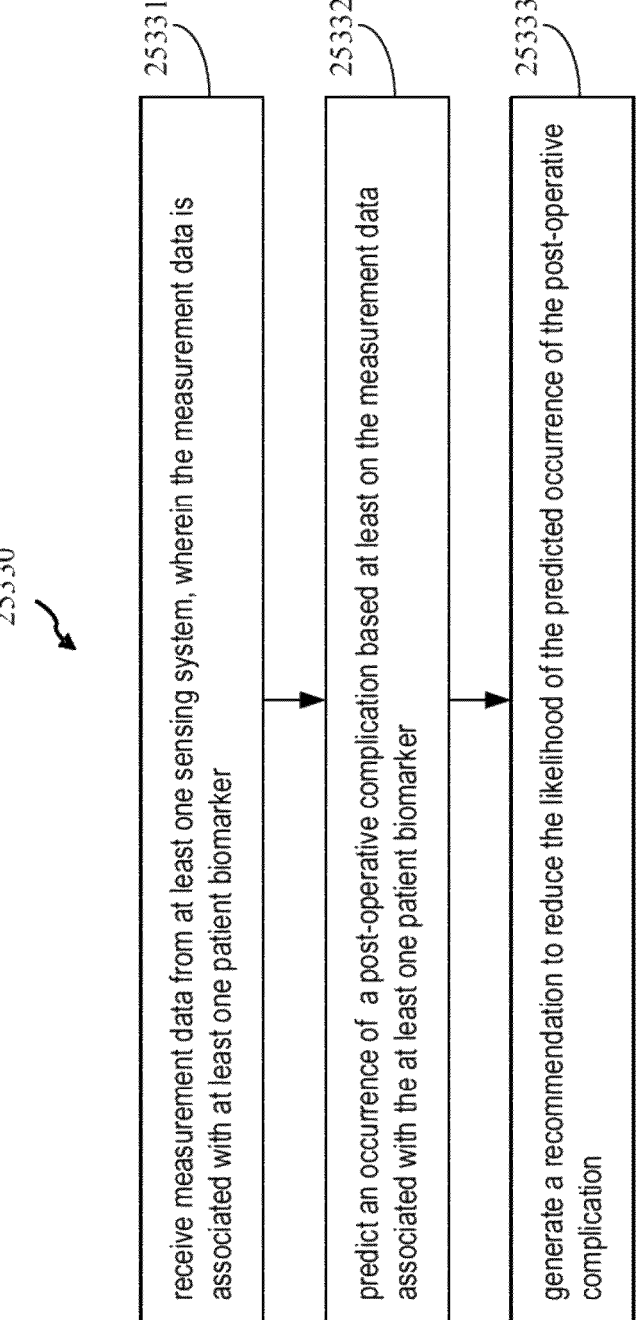

25330

25331 receive measurement data from at least one sensing system, wherein the measurement data is associated with at least one patient biomarker

25332 predict an occurrence of a post-operative complication based at least on the measurement data associated with the at least one patient biomarker

25333 generate a recommendation to reduce the likelihood of the predicted occurrence of the post-operative complication

FIG. 21

PATIENT SENSING - LUNG SEGMENTECTOMY- 1

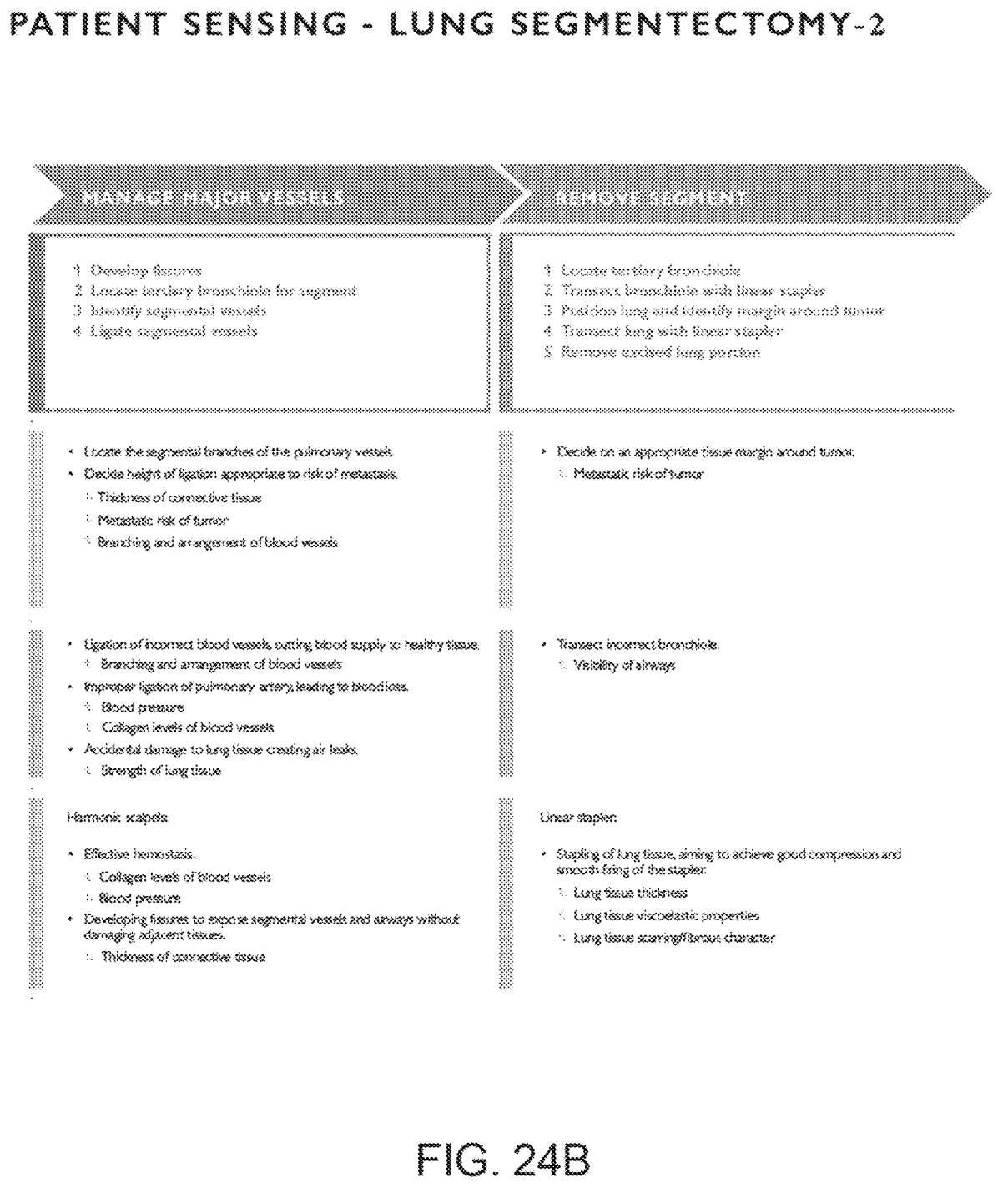

PATIENT SENSING - LUNG SEGMENTECTOMY-2

MANAGE MAJOR VESSELS

1. Develop fissures
2. Locate tertiary bronchiole for segment
3. Identify segmental vessels
4. Ligate segmental vessels

REMOVE SEGMENT

1. Locate tertiary bronchiole
2. Transect bronchiole with linear stapler
3. Position lung and identify margin around tumor
4. Transect lung with linear stapler
5. Remove excised lung portion

- Locate the segmental branches of the pulmonary vessels
- Decide height of ligation appropriate to risk of metastasis.
  - Thickness of connective tissue
  - Metastatic risk of tumor
  - Branching and arrangement of blood vessels

- Decide on an appropriate tissue margin around tumor.
  - Metastatic risk of tumor

- Ligation of incorrect blood vessels, cutting blood supply to healthy tissue.
  - Branching and arrangement of blood vessels
- Improper ligation of pulmonary artery, leading to blood loss.
  - Blood pressure
  - Collagen levels of blood vessels
- Accidental damage to lung tissue creating air leaks.
  - Strength of lung tissue

- Transect incorrect bronchiole.
  - Visibility of airways

Harmonic scalpels

- Effective hemostasis.
  - Collagen levels of blood vessels
  - Blood pressure
- Developing fissures to expose segmental vessels and airways without damaging adjacent tissues.
  - Thickness of connective tissue Linear stapler

- Stapling of lung tissue, aiming to achieve good compression and smooth firing of the stapler.
  - Lung tissue thickness
  - Lung tissue viscoelastic properties
  - Lung tissue scarring/fibrous character

FIG. 24B

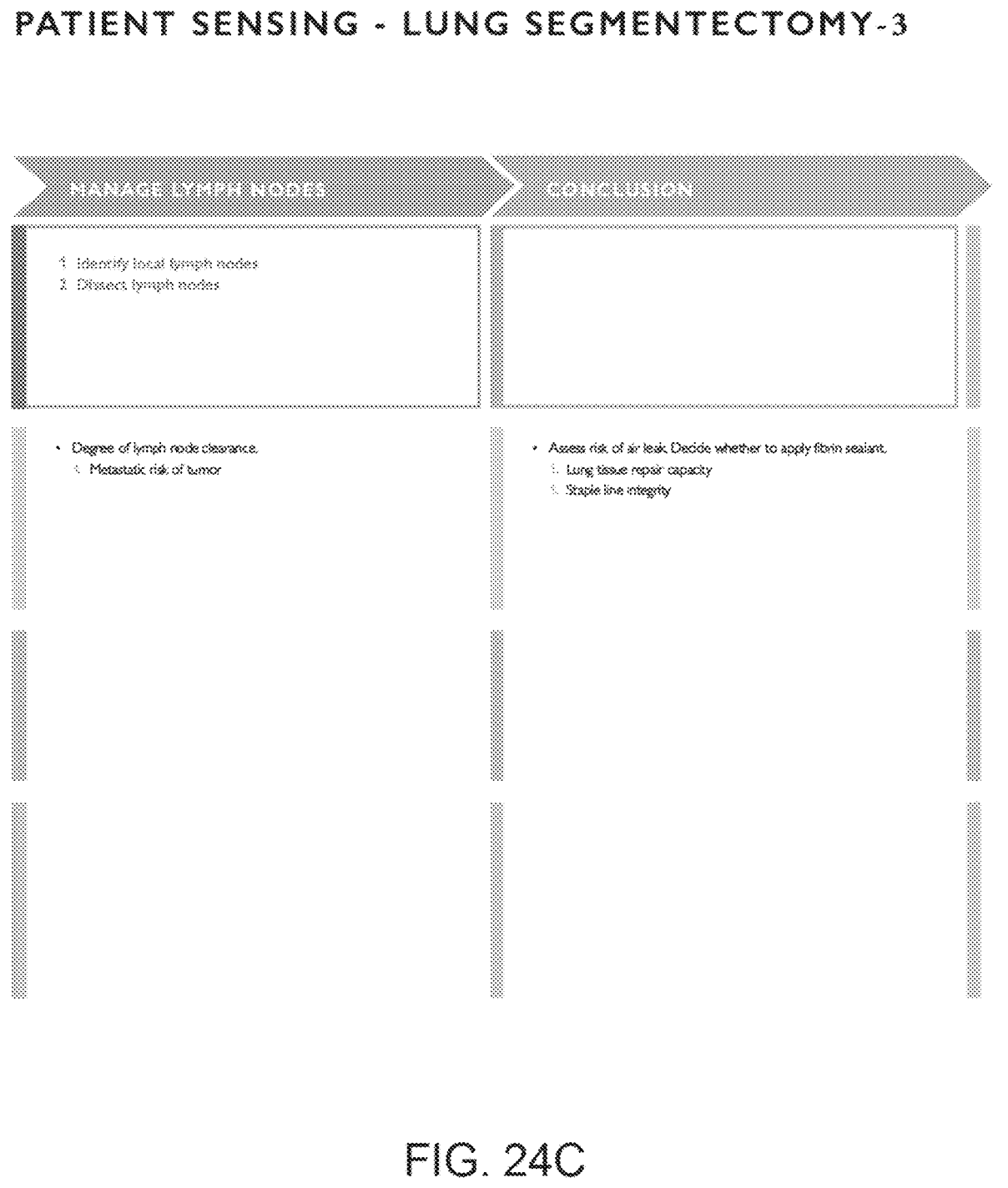

PATIENT SENSING - LUNG SEGMENTECTOMY-3

| MANAGE LYMPH NODES | CONCLUSION |
|---|---|
| 1. Identify local lymph nodes<br>2. Dissect lymph nodes | |

- Degree of lymph node clearance.
  - Metastatic risk of tumor

- Assess risk of air leak. Decide whether to apply fibrin sealant.
  - Lung tissue repair capacity
  - Staple line integrity

FIG. 24C

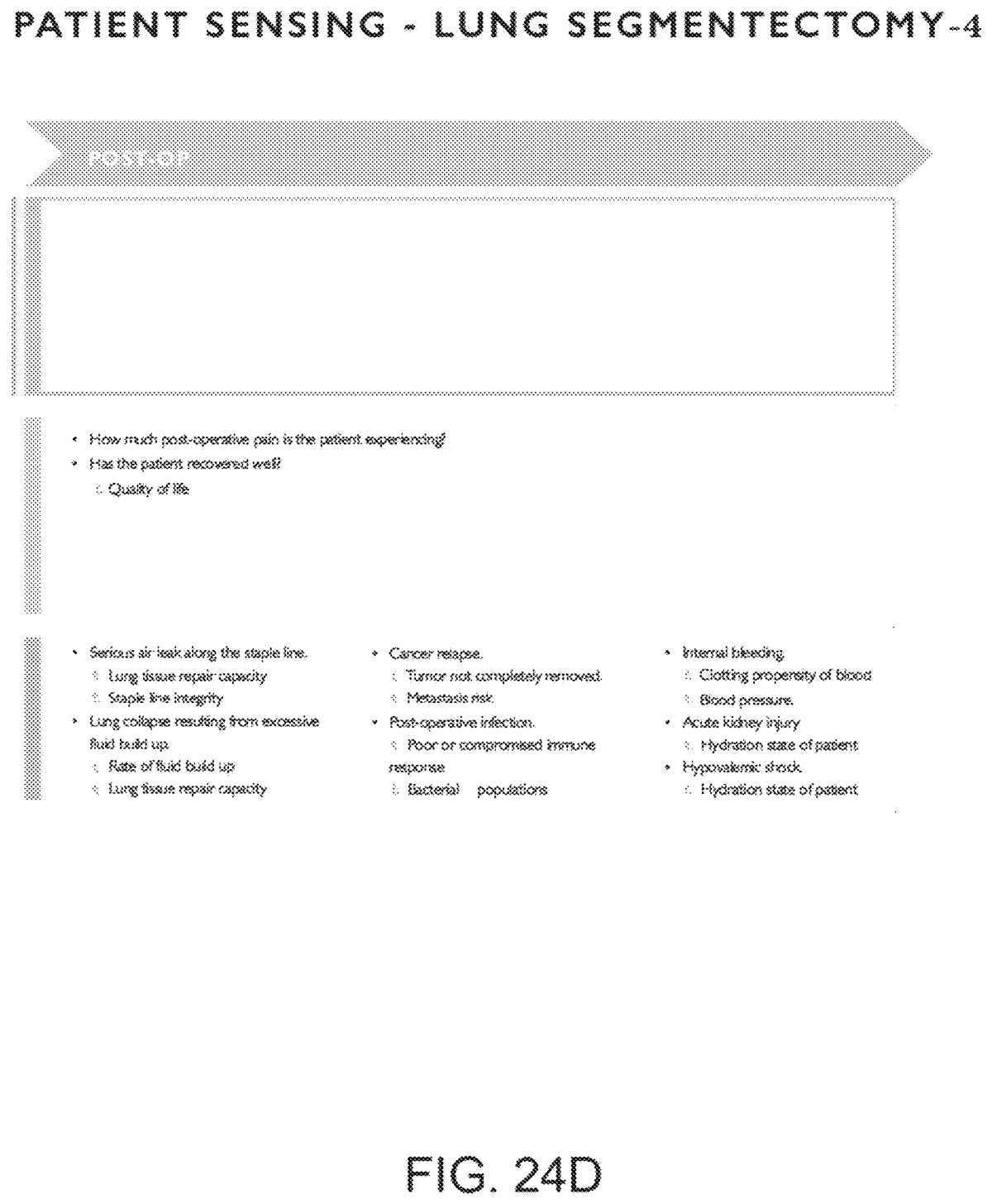

PATIENT SENSING - LUNG SEGMENTECTOMY-4

POST-OP

- How much post-operative pain is the patient experiencing?
- Has the patient recovered well?
  - Quality of life

- Serious air leak along the staple line.
  - Lung tissue repair capacity
  - Staple line integrity
- Lung collapse resulting from excessive fluid build up
  - Rate of fluid build up
  - Lung tissue repair capacity

- Cancer relapse.
  - Tumor not completely removed.
  - Metastasis risk
- Post-operative infection.
  - Poor or compromised immune response
  - Bacterial populations

- Internal bleeding.
  - Clotting propensity of blood
  - Blood pressure.
- Acute kidney injury
  - Hydration state of patient
- Hypovolemic shock
  - Hydration state of patient

FIG. 24D

THORACIC POST-SURGICAL MONITORING AND COMPLICATION PREDICTION

CROSS-REFERENCE TO RELATED APPLICATIONS

This application is related to the following, filed contemporaneously, the contents of each of which are incorporated by reference herein:

U.S. patent application Ser. No. 17/156,287, filed Jan. 22, 2021, entitled METHOD OF ADJUSTING A SURGICAL PARAMETER BASED ON BIOMARKER MEASUREMENTS.

BACKGROUND

Patient monitoring (e.g., monitoring post-surgery patients) in uncontrolled environments (e.g., when a patient is out of the hospital or other controlled environment) is typically discontinuous, delayed (e.g., received during follow-up visits or phone calls), immobile (e.g., restricts patient mobility), incomplete (e.g., lack of monitored parameters), and/or unscientific (e.g., based on patient self-assessment or other unprofessional measurement). Consumer sensing systems are typically unsuitable for patient monitoring. Consumer sensing systems may perform only generic biomarker sensing.

SUMMARY

Systems, methods, and instrumentalities are disclosed herein for a (e.g., pre-, in-, and/or post-operative) patient monitoring system. Patient biomarkers may be monitored before, during, and/or after thoracic surgery to predict complications, detect complications, track recovery, and/or make pre-, in- and/or post-surgery recommendations to avoid predicted complications and/or mitigate detected complications. Complications (e.g., prolonged air leak or esophageal stricture) may be predicted (e.g., by a model) based on patient parameters and/or patient biomarker measurements. Complications may be predicted or detected based on patient biomarker measurements compared to threshold values associated with a patient biomarker (e.g., developed from baselines) generated based on patient parameters, pre- and/or in-surgery patient biomarker measurements, and/or surgical details (e.g., decrease in lung capacity). Recovery milestones may be tracked based on patient biomarker measurements compared to predicted patient biomarker measurements for recovery stages. A recommendation (e.g., to avoid a predicted complication and/or mitigate a detected complication) may be a patient-specific selection and/or modification of more of the following: surgical preparation, in-surgery procedures, surgical instrument selection, surgical and/or post-surgical instrument settings (e.g., stapler force, suction control program), post-surgery procedures, in-surgery, and/or post-surgery monitoring, etc. Notifications (e.g., real-time notification) may be generated, for example, to indicate predictions, detections (e.g., of complications and/or milestones), recommendations (e.g., for manual and/or automated implementation), etc. Functionality may be variously implemented (e.g., distributed) among one or more of the following: wearable sensing system(s), hub(s), controllable device(s), display device(s), etc.

BRIEF DESCRIPTION OF THE DRAWINGS

FIG. 1B is a block diagram of an example relationship among sensing systems, biomarkers, and physiologic systems.

FIG. 18 shows example correlation between relevant patient biomarkers and thoracic surgical procedural steps.

FIG. 20 illustrates an example of a logic flow diagram for detecting post-operative complication, in accordance with at least one aspect of the present disclosure.

FIG. 21 illustrates an example of a logic flow diagram for predicting a post-operative complication, in accordance with at least one aspect of the present disclosure.

FIGS. 24A-24D illustrates example procedure steps of a lung segmentectomy or a thoracic surgical procedure and example use of patient biomarker measurements.

DETAILED DESCRIPTION

Figure 1A:
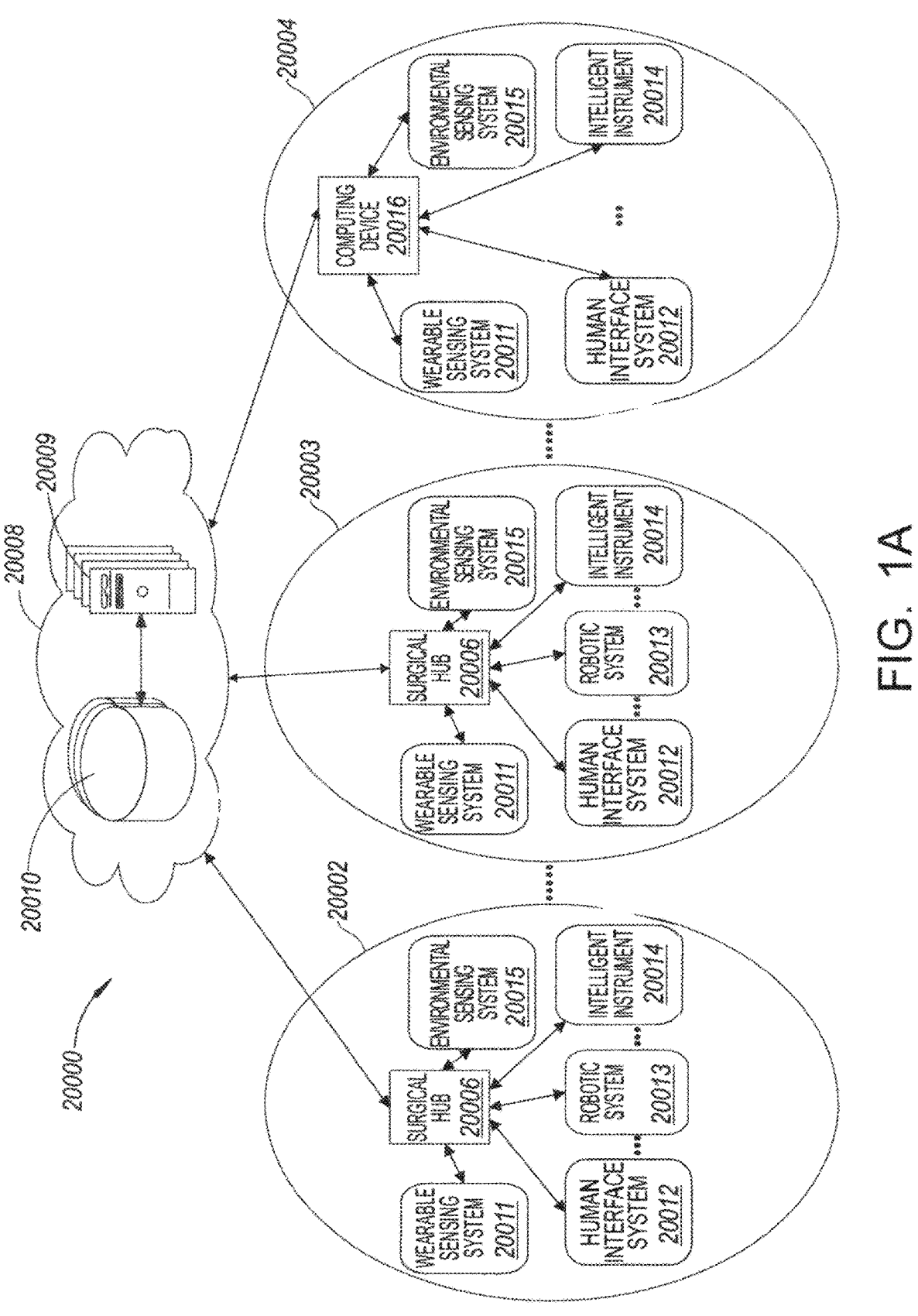
FIG. 1A is a block diagram of a computer-implemented patient and surgeon monitoring system.

FIG. 1A is a block diagram of a computer-implemented patient and surgeon monitoring system 20000. The patient and surgeon monitoring system 20000 may include one or more surgeon monitoring systems 20002 and a one or more patient monitoring systems (e.g., one or more controlled patient monitoring systems 20003 and one or more uncontrolled patient monitoring systems 20004). Each surgeon monitoring system 20002 may include a computer-implemented interactive surgical system. Each surgeon monitoring system 20002 may include at least one of the following: a surgical hub 20006 in communication with a cloud computing system 20008, for example, as described in FIG. 2A. Each of the patient monitoring systems may include at least one of the following: a surgical hub 20006 or a computing device 20016 in communication with a could computing system 20008, for example, as further described in FIG. 2B and FIG. 2C. The cloud computing system 20008 may include at least one remote cloud server 20009 and at least one remote cloud storage unit 20010. Each of the surgeon monitoring systems 20002, the controlled patient monitoring systems 20003, or the uncontrolled patient monitoring systems 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more surgeon sensing systems, and/or one or more patient sensing systems. The environmental sensing system 20015 may include one or more devices, for example, used for measuring one or more environmental attributes, for example, as further described in FIG. 2A. The robotic system 20013 (same as 20034 in FIG. 2A) may include a plurality of devices used for performing a surgical procedure, for example, as further described in FIG. 2A.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

FIG. 1B is a block diagram of an example relationship among sensing systems 20001, biomarkers 20005, and physiologic systems 20007. The relationship may be employed in the computer-implemented patient and surgeon monitoring system 20000 and in the systems, devices, and methods disclosed herein. For example, the sensing systems 20001 may include the wearable sensing system 20011 (which may include one or more surgeon sensing systems and one or more patient sensing systems) and the environmental sensing system 20015 as discussed in FIG. 1A. The one or more sensing systems 20001 may measure data relating to various biomarkers 20005. The one or more sensing systems 20001 may measure the biomarkers 20005 using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers 20005 as described herein using one of more of the following sensing technologies: photoplethysmography, electrocardiography, electroencephalography, colorimetry, impedimentary, potentiometry, amperometry, etc.

The biomarkers 20005 measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers 20005 may relate to physiologic systems 20007, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system 20000, for example. The information from the biomarkers may be determined and/or used by the computer-implemented patient and surgeon monitoring system 20000 to improve said systems and/or to improve patient outcomes, for example.

The one or more sensing systems 20001, biomarkers 20005, and physiological systems 20007 are described in more detail below.

A sleep sensing system may measure sleep data, including heart rate, respiration rate, body temperature, movement, and/or brain signals. The sleep sensing system may measure sleep data using a photoplethysmogram (PPG), electrocardiogram (ECG), microphone, thermometer, accelerometer, electroencephalogram (EEG), and/or the like. The sleep sensing system may include a wearable device such as a wristband.

Based on the measured sleep data, the sleep sensing system may detect sleep biomarkers, including but not limited to, deep sleep quantifier, REM sleep quantifier, disrupted sleep quantifier, and/or sleep duration. The sleep sensing system may transmit the measured sleep data to a processing unit. The sleep sensing system and/or the processing unit may detect deep sleep when the sensing system senses sleep data, including reduced heart rate, reduced respiration rate, reduced body temperature, and/or reduced movement. The sleep sensing system may generate a sleep quality score based on the detected sleep physiology.

In an example, the sleep sensing system may send the sleep quality score to a computing system, such as a surgical hub. In an example, the sleep sensing system may send the detected sleep biomarkers to a computing system, such as a surgical hub. In an example, the sleep sensing system may send the measured sleep data to a computing system, such as a surgical hub. The computing system may derive sleep physiology based on the received measured data and generate one or more sleep biomarkers such as deep sleep quantifiers. The computing system may generate a treatment plan, including a pain management strategy, based on the sleep biomarkers. The surgical hub may detect potential risk factors or conditions, including systemic inflammation and/or reduced immune function, based on the sleep biomarkers.

A core body temperature sensing system may measure body temperature data including temperature, emitted frequency spectra, and/or the like. The core body temperature sensing system may measure body temperature data using some combination of thermometers and/or radio telemetry. The core body temperature sensing system may include an ingestible thermometer that measures the temperature of the digestive tract. The ingestible thermometer may wirelessly transmit measured temperature data. The core body temperature sensing system may include a wearable antenna that measures body emission spectra. The core body temperature sensing system may include a wearable patch that measures body temperature data.

The core body temperature sensing system may calculate body temperature using the body temperature data. The core body temperature sensing system may transmit the calculated body temperature to a monitoring device. The monitoring device may track the core body temperature data over time and display it to a user.

The core body temperature sensing system may process the core body temperature data locally or send the data to a processing unit and/or a computing system. Based on the measured temperature data, the core body temperature sensing system may detect body temperature-related biomarkers, complications and/or contextual information that may include abnormal temperature, characteristic fluctuations, infection, menstrual cycle, climate, physical activity, and/or sleep.

For example, the core body temperature sensing system may detect abnormal temperature based on temperature being outside the range of 36.5° C. and 37.5° C. For example, the core body temperature sensing system may detect post-operation infection or sepsis based on certain temperature fluctuations and/or when core body temperature reaches abnormal levels. For example, the core body temperature sensing system may detect physical activities using measured fluctuations in core body temperature.

For example, the body temperature sensing system may detect core body temperature data and trigger the sensing system to emit a cooling or heating element to raise or lower the body temperature in line with the measured ambient temperature.

In an example, the body temperature sensing system may send the body temperature-related biomarkers to a computing system, such as a surgical hub. In an example, the body temperature sensing system may send the measured body temperature data to the computing system. The computer system may derive the body temperature-related biomarkers based on the received body temperature data.

A maximal oxygen consumption (VO2 max) sensing system may measure VO2 max data, including oxygen uptake, heart rate, and/or movement speed. The VO2 max sensing system may measure VO2 max data during physical activities, including running and/or walking. The VO2 max sensing system may include a wearable device. The VO2 max sensing system may process the VO2 max data locally or transmit the data to a processing unit and/or a computing system.

Based on the measured VO2 max data, the sensing system and/or the computing system may derive, detect, and/or calculate biomarkers, including a VO2 max quantifier, VO2 max score, physical activity, and/or physical activity intensity. The VO2 max sensing system may select correct VO2 max data measurements during correct time segments to calculate accurate VO2 max information. Based on the VO2 max information, the sensing system may detect dominating cardio, vascular, and/or respiratory limiting factors. Based on the VO2 max information, risks may be predicted including adverse cardiovascular events in surgery and/or increased risk of in-hospital morbidity. For example, increased risk of in-hospital morbidity may be detected when the calculated VO2 max quantifier falls below a specific threshold, such as 18.2 ml kg-1 min-1.

In an example, the VO2 max sensing system may send the VO2 max-related biomarkers to a computing system, such as a surgical hub. In an example, the VO2 max sensing system may send the measured VO2 max data to the computing system. The computer system may derive the VO2 max-related biomarkers based on the received VO2 max data.

A physical activity sensing system may measure physical activity data, including heart rate, motion, location, posture, range-of-motion, movement speed, and/or cadence. The physical activity sensing system may measure physical activity data including accelerometer, magnetometer, gyroscope, global positioning system (GPS), PPG, and/or ECG. The physical activity sensing system may include a wearable device. The physical activity wearable device may include, but is not limited to, a watch, wrist band, vest, glove, belt, headband, shoe, and/or garment. The physical activity sensing system may locally process the physical activity data or transmit the data to a processing unit and/or a computing system.

Based on the measured physical activity data, the physical activity sensing system may detect physical activity-related biomarkers, including but not limited to exercise activity, physical activity intensity, physical activity frequency, and/or physical activity duration. The physical activity sensing system may generate physical activity summaries based on physical activity information.

For example, the physical activity sensing system may send physical activity information to a computing system. For example, the physical activity sensing system may send measured data to a computing system. The computing system may, based on the physical activity information, generate activity summaries, training plans, and/or recovery plans. The computing system may store the physical activity information in user profiles. The computing system may display the physical activity information graphically. The computing system may select certain physical activity information and display the information together or separately.

An alcohol consumption sensing system may measure alcohol consumption data including alcohol and/or sweat. The alcohol consumption sensing system may use a pump to measure perspiration. The pump may use a fuel cell that reacts with ethanol to detect alcohol presence in perspiration. The alcohol consumption sensing system may include a wearable device, for example, a wristband. The alcohol consumption sensing system may use microfluidic applications to measure alcohol and/or sweat. The microfluidic applications may measure alcohol consumption data using sweat stimulation and wicking with commercial ethanol sensors. The alcohol consumption sensing system may include a wearable patch that adheres to skin. The alcohol consumption sensing system may include a breathalyzer. The sensing system may process the alcohol consumption data locally or transmit the data to a processing unit and/or computing system.

Based on the measured alcohol consumption data, the sensing system may calculate a blood alcohol concentration. The sensing system may detect alcohol consumption conditions and/or risk factors. The sensing system may detect alcohol consumption-related biomarkers including reduced immune capacity, cardiac insufficiency, and/or arrhythmia. Reduced immune capacity may occur when a patient consumes three or more alcohol units per day. The sensing system may detect risk factors for postoperative complications including infection, cardiopulmonary complication, and/or bleeding episodes. Healthcare providers may use the detected risk factors for predicting or detecting post-operative or post-surgical complications, for example, to affect decisions and precautions taken during post-surgical care.

In an example, the alcohol consumption sensing system may send the alcohol consumption-related biomarkers to a computing system, such as a surgical hub. In an example, the alcohol consumption sensing system may send the measured alcohol consumption data to the computing system. The computer system may derive the alcohol consumption-related biomarkers based on the received alcohol consumption data.

A respiration sensing system may measure respiration rate data, including inhalation, exhalation, chest cavity movement, and/or airflow. The respiration sensing system may measure respiration rate data mechanically and/or acoustically. The respiration sensing system may measure respiration rate data using a ventilator. The respiration sensing system may measure respiration data mechanically by detecting chest cavity movement. Two or more applied electrodes on a chest may measure the changing distance between the electrodes to detect chest cavity expansion and contraction during a breath. The respiration sensing system may include a wearable skin patch. The respiration sensing system may measure respiration data acoustically using a microphone to record airflow sounds. The respiration sensing system may locally process the respiration data or transmit the data to a processing unit and/or computing system.

Based on measured respiration data, the respiration sensing system may generate respiration-related biomarkers including breath frequency, breath pattern, and/or breath depth. Based on the respiratory rate data, the respiration sensing system may generate a respiration quality score.

Based on the respiration rate data, the respiration sensing system may detect respiration-related biomarkers including irregular breathing, pain, air leak, collapsed lung, lung tissue and strength, and/or shock. For example, the respiration sensing system may detect irregularities based on changes in breath frequency, breath pattern, and/or breath depth. For example, the respiration sensing system may detect post-operative pain based on short, sharp breaths. For example, the respiration sensing system may detect an air leak based on a volume difference between inspiration and expiration. For example, the respiration sensing system may detect a collapsed lung based on increased breath frequency combined with a constant volume inhalation. For example, the respiration sensing system may detect lung tissue strength and shock including systemic inflammatory response syndrome (SIRS) based on an increase in respiratory rate, including more than 2 standard deviations. In an example, the detection described herein may be performed by a computing system based on measured data and/or related biomarkers generated by the respiration sensing system.

An oxygen saturation sensing system may measure oxygen saturation data, including light absorption, light transmission, and/or light reflectance. The oxygen saturation sensing system may use pulse oximetry. For example, the oxygen saturation sensing system may use pulse oximetry by measuring the absorption spectra of deoxygenated and oxygenated hemoglobin. The oxygen saturation sensing system may include one or more light-emitting diodes (LEDs) with predetermined wavelengths. The LEDs may impose light on hemoglobin. The oxygen saturation sensing system may measure the amount of imposed light absorbed by the hemoglobin. The oxygen saturation sensing system may measure the amount of transmitted light and/or reflected light from the imposed light wavelengths. The oxygen saturation sensing system may include a wearable device, including an earpiece and/or a watch. The oxygen saturation sensing system may process the measured oxygen saturation data locally or transmit the data to a processing unit and/or computing system.

Based on the oxygen saturation data, the oxygen saturation sensing system may calculate oxygen saturation-related biomarkers including peripheral blood oxygen saturation (SpO2), hemoglobin oxygen concentration, and/or changes in oxygen saturation rates. For example, the oxygen saturation sensing system may calculate SpO2 using the ratio of measured light absorbances of each imposed light wavelength.

Based on the oxygen saturation data, the oxygen saturation sensing system may predict oxygen saturation-related biomarkers, complications, and/or contextual information including cardiothoracic performance, delirium, collapsed lung, and/or recovery rates. For example, the oxygen saturation sensing system may detect post-operation delirium when the sensing system measures pre-operation SpO2 values below 59.5%. For example, an oxygen saturation sensing system may help monitor post-operation patient recovery. Low SpO2 may reduce the repair capacity of tissues because low oxygen may reduce the amount of energy a cell can produce. For example, the oxygen saturation sensing system may detect a collapsed lung based on low post-operation oxygen saturation. In an example, the detection described herein may be performed by a computing system based on measured data and/or related biomarkers generated by the oxygen saturation sensing system.

A blood pressure sensing system may measure blood pressure data including blood vessel diameter, tissue volume, and/or pulse transit time. The blood pressure sensing system may measure blood pressure data using oscillometric measurements, ultrasound patches, photoplethysmography, and/or arterial tonometry. The blood pressure sensing system using photoplethysmography may include a photodetector to sense light scattered by imposed light from an optical emitter. The blood pressure sensing system using arterial tonometry may use arterial wall applanation. The blood pressure sensing system may include an inflatable cuff, wristband, watch and/or ultrasound patch.

Based on the measured blood pressure data, a blood pressure sensing system may quantify blood pressure-related biomarkers including systolic blood pressure, diastolic blood pressure, and/or pulse transit time. The blood pressure sensing system may use the blood pressure-related biomarkers to detect blood pressure-related conditions such as abnormal blood pressure. The blood pressure sensing system may detect abnormal blood pressure when the measured systolic and diastolic blood pressures fall outside the range of 90/60 to 120-90 (systolic/diastolic). For example, the blood pressure sensing system may detect post-operation septic or hypovolemic shock based on measured low blood pressure. For example, the blood pressure sensing system may detect a risk of edema based on detected high blood pressure. The blood pressure sensing system may predict the required seal strength of a harmonic seal based on measured blood pressure data. Higher blood pressure may require a stronger seal to overcome bursting. The blood pressure sensing system may display blood pressure information locally or transmit the data to a system. The sensing system may display blood pressure information graphically over a period of time.

A blood pressure sensing system may process the blood pressure data locally or transmit the data to a processing unit and/or a computing system. In an example, the detection, prediction and/or determination described herein may be performed by a computing system based on measured data and/or related biomarkers generated by the blood pressure sensing system.

A blood sugar sensing system may measure blood sugar data including blood glucose level and/or tissue glucose level. The blood sugar sensing system may measure blood sugar data non-invasively. The blood sugar sensing system may use an earlobe clip. The blood sugar sensing system may display the blood sugar data.

Based on the measured blood sugar data, the blood sugar sensing system may infer blood sugar irregularity. Blood sugar irregularity may include blood sugar values falling outside a certain threshold of normally occurring values. A normal blood sugar value may include the range between 70 and 120 mg/dL while fasting. A normal blood sugar value may include the range between 90 and 160 mg/dL while not-fasting.

For example, the blood sugar sensing system may detect a low fasting blood sugar level when blood sugar values fall below 50 mg/dL. For example, the blood sugar sensing system may detect a high fasting blood sugar level when blood sugar values exceed 315 mg/dL. Based on the measured blood sugar levels, the blood sugar sensing system may detect blood sugar-related biomarkers, complications, and/or contextual information including diabetes-associated peripheral arterial disease, stress, agitation, reduced blood flow, risk of infection, and/or reduced recovery times.

The blood sugar sensing system may process blood sugar data locally or transmit the data to a processing unit and/or computing system. In an example, the detection, prediction and/or determination described herein may be performed by a computing system based on measured data and/or related biomarkers generated by the blood sugar sensing system.

A heart rate variability (HRV) sensing system may measure HRV data including heartbeats and/or duration between consecutive heartbeats. The HRV sensing system may measure HRV data electrically or optically. The HRV sensing system may measure heart rate variability data electrically using ECG traces. The HRV sensing system may use ECG traces to measure the time period variation between R peaks in a QRS complex. An HRV sensing system may measure heart rate variability optically using PPG traces. The HRV sensing system may use PPG traces to measure the time period variation of inter-beat intervals. The HRV sensing system may measure HRV data over a set time interval. The HRV sensing system may include a wearable device, including a ring, watch, wristband, and/or patch.

Based on the HRV data, an HRV sensing system may detect HRV-related biomarkers, complications, and/or contextual information including cardiovascular health, changes in HRV, menstrual cycle, meal monitoring, anxiety levels, and/or physical activity. For example, an HRV sensing system may detect high cardiovascular health based on high HRV. For example, an HRV sensing system may predict pre-operative stress, and use pre-operative stress to predict post-operative pain. For example, an HRV sensing system may indicate post-operative infection or sepsis based on a decrease in HRV.

The HRV sensing system may locally process HRV data or transmit the data to a processing unit and/or a computing system. In an example, the detection, prediction, and/or determination described herein may be performed by a computing system based on measured data and/or related biomarkers generated by the HRV sensing system.

A potential of hydrogen (pH) sensing system may measure pH data including blood pH and/or sweat pH. The pH sensing system may measure pH data invasively and/or non-invasively. The pH sensing system may measure pH data non-invasively using a colorimetric approach and pH sensitive dyes in a microfluidic circuit. In a colorimetric approach, pH sensitive dyes may change color in response to sweat pH. The pH sensing system may measure pH using optical spectroscopy to match color change in pH sensitive dyes to a pH value. The pH sensing system may include a wearable patch. The pH sensing system may measure pH data during physical activity.

Based on the measured pH data, the pH sensing system may detect pH-related biomarkers, including normal blood pH, abnormal blood pH, and/or acidic blood pH. The pH sensing system may detect pH-related biomarkers, complications, and/or contextual information by comparing measured pH data to a standard pH scale. A standard pH scale may identify a healthy pH range to include values between 7.35 and 7.45.

The pH sensing system may use the pH-related biomarkers to indicate pH conditions including post-operative internal bleeding, acidosis, sepsis, lung collapse, and/or hemorrhage. For example, the pH sensing system may predict post-operative internal bleeding based on pre-operation acidic blood pH. Acidic blood may reduce blood clotting capacity by inhibiting thrombin generation. For example, the pH sensing system may predict sepsis and/or hemorrhage based on acidic pH. Lactic acidosis may cause acidic pH. The pH sensing system may continuously monitor blood pH data as acidosis may only occur during exercise.

The pH sensing system may locally process pH data or transmit pH data to a processing unit and/or computing system. In an example, the detection, prediction and/or determination described herein may be performed by a computing system based on measured data and/or related biomarkers generated by the pH sensing system.

A hydration state sensing system may measure hydration data including water light absorption, water light reflection, and/or sweat levels. The hydration state sensing system may use optical spectroscopy or sweat-based colorimetry. The hydration state sensing system may use optical spectroscopy by imposing emitted light onto skin and measuring the reflected light. Optical spectroscopy may measure water content by measuring amplitudes of the reflected light from certain wavelengths, including 1720 nm, 1750 nm, and/or 1770 nm. The hydration state sensing system may include a wearable device that may impose light onto skin. The wearable device may include a watch. The hydration state sensing system may use sweat-based colorimetry to measure sweat levels. Sweat-based colorimetry may be processed in conjunction with user activity data and/or user water intake data.

Based on the hydration data, the hydration state sensing system may detect water content. Based on the water content, a hydration state sensing system may identify hydration-related biomarkers, complications, and/or contextual information including dehydration, risk of kidney injury, reduced blood flow, risk of hypovolemic shock during or after surgery, and/or decreased blood volume.

For example, the hydration state sensing system, based on identified hydration, may detect health risks. Dehydration may negatively impact overall health. For example, the hydration state sensing system may predict risk of post-operation acute kidney injury when it detects reduced blood flow resulting from low hydration levels. For example, the hydration state sensing system may calculate the risk of hypovolemic shock during or after surgery when the sensing system detects dehydration or decreased blood volume. The hydration state sensing system may use the hydration level information to provide context for other received biomarker data, which may include heart rate. The hydration state sensing system may measure hydration state data continuously. Continuous measurement may consider various factors, including exercise, fluid intake, and/or temperature, which may influence the hydration state data.

The hydration state sensing system may locally process hydration data or transmit the data to a processing unit and/or computing system. In an example, the detection, prediction, and/or determination described herein may be performed by a computing system based on measured data and/or related biomarkers generated by the hydration state sensing system.

A heart rate sensing system may measure heart rate data including heart chamber expansion, heart chamber contraction, and/or reflected light. The heart rate sensing system may use ECG and/or PPG to measure heart rate data. For example, the heart rate sensing system using ECG may include a radio transmitter, receiver, and one or more electrodes. The radio transmitter and receiver may record voltages across electrodes positioned on the skin resulting from expansion and contraction of heart chambers. The heart rate sensing system may calculate heart rate using measured voltage. For example, the heart rate sensing system using PPG may impose green light on skin and record the reflected light in a photodetector. The heart rate sensing system may calculate heart rate using the measured light absorbed by the blood over a period of time. The heart rate sensing system may include a watch, a wearable elastic band, a skin patch, a bracelet, garments, a wrist strap, an earphone, and/or a headband. For example, the heart rate sensing system may include a wearable chest patch. The wearable chest patch may measure heart rate data and other vital signs or critical data including respiratory rate, skin temperature, body posture, fall detection, single-lead ECG, R-R intervals, and step counts. The wearable chest patch may locally process heart rate data or transmit the data to a processing unit. The processing unit may include a display.

Based on the measured heart rate data, the heart rate sensing system may calculate heart rate-related biomarkers including heart rate, heart rate variability, and/or average heart rate. Based on the heart rate data, the heart rate sensing system may detect biomarkers, complications, and/or contextual information including stress, pain, infection, and/or sepsis. The heart rate sensing system may detect heart rate conditions when heart rate exceeds a normal threshold. A normal threshold for heartrate may include the range of 60 to 100 heartbeats per minute. The heart rate sensing system may diagnose post-operation infection, sepsis, or hypovolemic shock based on increased heart rate, including heart rate in excess of 90 beats per minute.

The heart rate sensing system may process heart rate data locally or transmit the data to a processing unit and/or computing system. In an example, the detection, prediction, and/or determination described herein may be performed by a computing system based on measured data and/or related biomarkers generated by the heart rate sensing system. A heart rate sensing system may transmit the heart rate information to a computing system, such as a surgical hub. The computing system may collect and display cardiovascular parameter information including heart rate, respiration, temperature, blood pressure, arrhythmia, and/or atrial fibrillation. Based on the cardiovascular parameter information, the computing system may generate a cardiovascular health score.

A skin conductance sensing system may measure skin conductance data including electrical conductivity. The skin conductance sensing system may include one or more electrodes. The skin conductance sensing system may measure electrical conductivity by applying a voltage across the electrodes. The electrodes may include silver or silver chloride. The skin conductance sensing system may be placed on one or more fingers. For example, the skin conductance sensing system may include a wearable device. The wearable device may include one or more sensors. The wearable device may attach to one or more fingers. Skin conductance data may vary based on sweat levels.

The skin conductance sensing system may locally process skin conductance data or transmit the data to a computing system. Based on the skin conductance data, a skin conductance sensing system may calculate skin conductance-related biomarkers including sympathetic activity levels. For example, a skin conductance sensing system may detect high sympathetic activity levels based on high skin conductance.

A peripheral temperature sensing system may measure peripheral temperature data including extremity temperature. The peripheral temperature sensing system may include a thermistor, thermoelectric effect, or infrared thermometer to measure peripheral temperature data. For example, the peripheral temperature sensing system using a thermistor may measure the resistance of the thermistor. The resistance may vary as a function of temperature. For example, the peripheral temperature sensing system using the thermoelectric effect may measure an output voltage. The output voltage may increase as a function of temperature. For example, the peripheral temperature sensing system using an infrared thermometer may measure the intensity of radiation emitted from a body's blackbody radiation. The intensity of radiation may increase as a function of temperature.

Based on peripheral temperature data, the peripheral temperature sensing system may determine peripheral temperature-related biomarkers including basal body temperature, extremity skin temperature, and/or patterns in peripheral temperature. Based on the peripheral temperature data, the peripheral temperature sensing system may detect conditions including diabetes.

The peripheral temperature sensing system may locally process peripheral temperature data and/or biomarkers or transmit the data to a processing unit. For example, the peripheral temperature sensing system may send peripheral temperature data and/or biomarkers to a computing system, such as a surgical hub. The computing system may analyze the peripheral temperature information with other biomarkers, including core body temperature, sleep, and menstrual cycle. For example, the detection, prediction, and/or determination described herein may be performed by a computing system based on measured data and/or related biomarkers generated by the peripheral temperature sensing system.

A tissue perfusion pressure sensing system may measure tissue perfusion pressure data including skin perfusion pressure. The tissue perfusion sensing system may use optical methods to measure tissue perfusion pressure data. For example, the tissue perfusion sensing system may illuminate skin and measure the light transmitted and reflected to detect changes in blood flow. The tissue perfusion sensing system may apply occlusion. For example, the tissue perfusion sensing system may determine skin perfusion pressure based on the measured pressure used to restore blood flow after occlusion. The tissue perfusion sensing system may measure the pressure to restore blood flow after occlusion using a strain gauge or laser doppler flowmetry. The measured change in frequency of light caused by movement of blood may directly correlate with the number and velocity of red blood cells, which the tissue perfusion pressure sensing system may use to calculate pressure. The tissue perfusion pressure sensing system may monitor tissue flaps during surgery to measure tissue perfusion pressure data.

Based on the measured tissue perfusion pressure data, the tissue perfusion pressure sensing system may detect tissue perfusion pressure-related biomarkers, complications, and/or contextual information including hypovolemia, internal bleeding, and/or tissue mechanical properties. For example, the tissue perfusion pressure sensing system may detect hypovolemia and/or internal bleeding based on a drop in perfusion pressure. Based on the measured tissue perfusion pressure data, the tissue perfusion pressure sensing system may inform surgical tool parameters and/or medical procedures. For example, the tissue perfusion pressure sensing system may determine tissue mechanical properties using the tissue perfusion pressure data. Based on the determined mechanical properties, the sensing system may generate stapling procedure and/or stapling tool parameter adjustment(s). Based on the determined mechanical properties, the sensing system may inform dissecting procedures. Based on the measured tissue perfusion pressure data, the tissue perfusion pressure sensing system may generate a score for overall adequacy of perfusion.

The tissue perfusion pressure sensing system may locally process tissue perfusion pressure data or transmit the data to a processing unit and/or computing system. In an example, the detection, prediction, determination, and/or generation described herein may be performed by a computing system based on measured data and/or related biomarkers generated by the tissue perfusion pressure sensing system.

A coughing and sneezing sensing system may measure coughing and sneezing data including coughing, sneezing, movement, and sound. The coughing and sneezing sensing system may track hand or body movement that may result from a user covering her mouth while coughing or sneezing. The sensing system may include an accelerometer and/or a microphone. The sensing system may include a wearable device. The wearable device may include a watch.

Based on the coughing and sneezing data, the sensing system may detect coughing and sneezing-related biomarkers, including but not limited to, coughing frequency, sneezing frequency, coughing severity, and/or sneezing severity. The sensing system may establish a coughing and sneezing baseline using the coughing and sneezing information. The coughing and sneezing sensing system may locally process coughing and sneezing data or transmit the data to a computing system.

Based on the coughing and sneezing data, the sensing system may detect coughing and sneezing-related biomarkers, complications, and/or contextual information including respiratory tract infection, infection, collapsed lung, pulmonary edema, gastroesophaegeal reflux disease, allergic rhinitis, and/or systemic inflammation. For example, the coughing and sneezing sensing system may indicate gastroesophageal reflux disease when the sensing system measures chronic coughing. Chronic coughing may lead to inflammation of the lower esophagus. Lower esophagus inflammation may affect the properties of stomach tissue for sleeve gastrectomy. For example, the coughing and sneezing sensing system may detect allergic rhinitis based on sneezing. Sneezing may link to systemic inflammation. Systemic inflammation may affect the mechanical properties of the lungs and/or other tissues. In an example, the detection, prediction, and/or determination described herein may be performed by a computing system based on measured data and/or related biomarkers generated by the coughing and sneezing sensing system.

A gastrointestinal (GI) motility sensing system may measure GI motility data including pH, temperature, pressure, and/or stomach contractions. The GI motility sensing system may use electrogastrography, electrogastroenterography, stethoscopes, and/or ultrasounds. The GI motility sensing system may include a non-digestible capsule. For example, the ingestible sensing system may adhere to the stomach lining. The ingestible sensing system may measure contractions using a piezoelectric device which generates a voltage when deformed.

Based on the GI data, the sensing system may calculate GI motility-related biomarkers including gastric, small bowel, and/or colonic transit times. Based on the gastrointestinal motility information, the sensing system may detect GI motility-related conditions including ileus. The GI motility sensing system may detect ileus based on a reduction in small bowel motility. The GI motility sensing system may notify healthcare professionals when it detects GI motility conditions. The GI motility sensing system may locally process GI motility data or transmit the data to a processing unit. In an example, the detection, prediction, and/or determination described herein may be performed by a computing system based on measured data and/or related biomarkers generated by the GI motility sensing system.

A GI tract imaging/sensing system may collect images of a patient's colon. The GI tract imaging/sensing system may include an ingestible wireless camera and a receiver. The GI tract imaging/sensing system may include one or more white LEDs, a battery, radio transmitter, and antenna. The ingestible camera may include a pill. The ingestible camera may travel through the digestive tract and take pictures of the colon. The ingestible camera may take pictures up to 35 frames per second during motion. The ingestible camera may transmit the pictures to a receiver. The receiver may include a wearable device. The GI tract imaging/sensing system may process the images locally or transmit them to a processing unit. Doctors may look at the raw images to make a diagnosis.

Based on the GI tract images, the GI tract imaging sensing system may identify GI tract-related biomarkers including stomach tissue mechanical properties or colonic tissue mechanical properties. Based on the collected images, the GI tract imaging sensing system may detect GI tract-related biomarkers, complications, and/or contextual information including mucosal inflammation, Crohn's disease, anastomotic leak, esophagus inflammation, and/or stomach inflammation. The GI tract imaging/sensing system may replicate a physician diagnosis using image analysis software. The GI tract imaging/sensing system may locally process images or transmit the data to a processing unit. In an example, the detection, prediction, and/or determination described herein may be performed by a computing system based on measured data and/or related biomarkers generated by the GI tract imaging/sensing system.

A respiratory tract bacteria sensing system may measure bacteria data including foreign DNA or bacteria. The respiratory tract bacteria sensing system may use a radio frequency identification (RFID) tag and/or electronic nose (e-nose). The sensing system using an RFID tag may include one or more gold electrodes, graphene sensors, and/or layers of peptides. The RFID tag may bind to bacteria. When bacteria bind to the RFID tag, the graphene sensor may detect a change in signal-to-signal presence of bacteria. The RFID tag may include an implant. The implant may adhere to a tooth. The implant may transmit bacteria data. The sensing system may use a portable e-nose to measure bacteria data.

Based on measured bacteria data, the respiratory tract bacteria sensing system may detect bacteria-related biomarkers including bacteria levels. Based on the bacteria data, the respiratory tract bacteria sensing system may generate an oral health score. Based on the detected bacteria data, the respiratory tract bacteria sensing system may identify bacteria-related biomarkers, complications, and/or contextual information, including pneumonia, lung infection, and/or lung inflammation. The respiratory tract bacteria sensing system may locally process bacteria information or transmit the data to a processing unit. In an example, the detection, prediction, and/or determination described herein may be performed by a computing system based on measured data and/or related biomarkers generated by the respiratory tract bacteria sensing system.

An edema sensing system may measure edema data including lower leg circumference, leg volume, and/or leg water content level. The edema sensing system may include a force sensitive resistor, strain gauge, accelerometer, gyroscope, magnetometer, and/or ultrasound. The edema sensing system may include a wearable device. For example, the edema sensing system may include socks, stockings, and/or ankle bands.

Based on the measured edema data, the edema sensing system may detect edema-related biomarkers, complications, and/or contextual information, including inflammation, rate of change in inflammation, poor healing, infection, leak, colorectal anastomotic leak, and/or water build-up.

For example, the edema sensing system may detect a risk of colorectal anastomotic leak based on fluid build-up. Based on the detected edema physiological conditions, the edema sensing system may generate a score for healing quality. For example, the edema sensing system may generate the healing quality score by comparing edema information to a certain threshold lower leg circumference. Based on the detected edema information, the edema sensing system may generate edema tool parameters including responsiveness to stapler compression. The edema sensing system may provide context for measured edema data by using measurements from the accelerometer, gyroscope, and/or magnetometer. For example, the edema sensing system may detect whether the user is sitting, standing, or lying down.

The edema sensing system may process measured edema data locally or transmit the edema data to a processing unit. In an example, the detection, prediction, and/or determination described herein may be performed by a computing system based on measured data and/or related biomarkers generated by the edema sensing system.

A mental aspect sensing system may measure mental aspect data, including heart rate, heart rate variability, brain activity, skin conductance, skin temperature, galvanic skin response, movement, and/or sweat rate. The mental aspect sensing system may measure mental aspect data over a set duration to detect changes in mental aspect data. The mental aspect sensing system may include a wearable device. The wearable device may include a wristband.

Based on the mental aspect data, the sensing system may detect mental aspect-related biomarkers, including emotional patterns, positivity levels, and/or optimism levels. Based on the detected mental aspect information, the mental aspect sensing system may identify mental aspect-related biomarkers, complications, and/or contextual information including cognitive impairment, stress, anxiety, and/or pain. Based on the mental aspect information, the mental aspect sensing system may generate mental aspect scores, including a positivity score, optimism score, confusion or delirium score, mental acuity score, stress score, anxiety score, depression score, and/or pain score.

Mental aspect data, related biomarkers, complications, contextual information, and/or mental aspect scores may be used to determine treatment courses, including pain relief therapies. For example, post-operative pain may be predicted when it detects pre-operative anxiety and/or depression. For example, based on detected positivity and optimism levels, the mental aspect sensing system may determine mood quality and mental state. Based on mood quality and mental state, the mental aspect sensing system may indicate additional care procedures that would benefit a patient, including paint treatments and/or psychological assistance. For example, based on detected cognitive impairment, confusion, and/or mental acuity, the mental aspects sensing system may indicate conditions including delirium, encephalopathy, and/or sepsis. Delirium may be hyperactive or hypoactive. For example, based on detected stress and anxiety, the mental aspect sensing system may indicate conditions including hospital anxiety and/or depression. Based on detected hospital anxiety and/or depression, the mental aspect sensing system may generate a treatment plan, including pain relief therapy and/or pre-operative support.

In an example, the detection, prediction, and/or determination described herein may be performed by a computing system based on measured data and/or related biomarkers generated by the mental aspect sensing system. The mental aspect sensing system may process mental aspect data locally or transmit the data to a processing unit.

A sweat sensing system may measure sweat data including sweat, sweat rate, cortisol, adrenaline, and/or lactate. The sweat sensing system may measure sweat data using microfluidic capture, saliva testing, nanoporous electrode systems, e-noses, reverse iontophoresis, blood tests, amperometric thin film biosensors, textile organic electrochemical transistor devices, and/or electrochemical biosensors. The sensing system may measure sweat data with microfluidic capture using a colorimetric or impedimetric method. The microfluidic capture may include a flexible patch placed in contact with skin. The sweat sensing system may measure cortisol using saliva tests. The saliva tests may use electrochemical methods and/or molecularly selective organic electrochemical transistor devices. The sweat sensing system may measure ion build-up that bind to cortisol in sweat to calculate cortisol levels. The sweat sensing system may use enzyme reactions to measure lactate. Lactate may be measured using lactate oxidase and/or lactate dehydrogenase methods.

Based on the measured sweat data, the sweat sensing system or processing unit may detect sweat-related biomarkers, complications, and/or contextual information including cortisol levels, adrenaline levels, and/or lactate levels. Based on the detected sweat data and/or related biomarkers, the sweat sensing system may indicate sweat physiological conditions including sympathetic nervous system activity, psychological stress, cellular immunity, circadian rhythm, blood pressure, tissue oxygenation, and/or post-operation pain. For example, based on sweat rate data, the sweat sensing system may detect psychological stress. Based on the detected psychological stress, the sweat sensing system may indicate heightened sympathetic activity. Heightened sympathetic activity may indicate post-operation pain.

Based on the detected sweat information, the sweat sensing system may detect sweat-related biomarkers, complications, and/or contextual information including post-operation infection, metastasis, chronic elevation, ventricular failure, sepsis, hemorrhage, hyperlactemia, and/or septic shock. For example, the sensing system may detect septic shock when serum lactate concentration exceeds a certain level, such as 2 mmol/L. For example, based on detected patterns of adrenaline surges, the sweat sensing system may indicate a risk of heart attack and/or stroke. For example, surgical tool parameter adjustments may be determined based on detected adrenaline levels. The surgical tool parameter adjustments may include settings for surgical sealing tools. For example, the sweat sensing system may predict infection risk and/or metastasis based on detected cortisol levels. The sweat sensing system may notify healthcare professionals about the condition.

In an example, the detection, prediction, and/or determination described herein may be performed by a computing system based on measured data and/or related biomarkers generated by the sweat sensing system. The sweat sensing system may locally process sweat data or transmit the sweat data to a processing unit.

A circulating tumor cell sensing system may detect circulating tumor cells. The circulating tumor cell sensing system may detect circulating tumor cells using an imaging agent. The imaging agent may use microbubbles attached with antibodies which target circulating tumor cells. The imaging agent may be injected into the bloodstream. The imaging agent may attach to circulating tumor cells. The circulating tumor cell sensing system may include an ultrasonic transmitter and receiver. The ultrasonic transmitter and receiver may detect the imaging agent attached to circulating tumor cells. The circulating tumor cell sensing system may receive circulating tumor cell data.

Based on the detected circulating tumor cells data, the circulating tumor cell sensing system may calculate metastatic risk. The presence of circulating cancerous cells may indicate metastatic risk. Circulating cancerous cells per milliliter of blood exceeding a threshold amount may indicate a metastatic risk. Cancerous cells may circulate the bloodstream when tumors metastasize. Based on the calculated metastatic risk, the circulating tumor cell sensing system may generate a surgical risk score. Based on the generated surgical risk score, the circulating tumor cell sensing system may indicate surgery viability and/or suggested surgical precautions.

In an example, the detection, prediction and/or determination described herein may be performed by a computing system based on measured data and/or related biomarkers generated by the circulating tumor cells sensing system. The circulating tumor cell sensing system may process the circulating tumor cell data locally or transmit the circulating tumor cells data to a processing unit.

An autonomic tone sensing system may measure autonomic tone data including skin conductance, heart rate variability, activity, and/or peripheral body temperature. The autonomic tone sensing system may include one or more electrodes, PPG trace, ECG trace, accelerometer, GPS, and/or thermometer. The autonomic tone sensing system may include a wearable device that may include a wristband and/or finger band.

Based on the autonomic tone data, the autonomic tone sensing system may detect autonomic tone-related biomarkers, complications, and/or contextual information, including sympathetic nervous system activity level and/or parasympathetic nervous system activity level. The autonomic tone may describe the basal balance between the sympathetic and parasympathetic nervous system. Based on the measured autonomic tone data, the autonomic tone sensing system may indicate risk for post-operative conditions including inflammation and/or infection. High sympathetic activity may associate with increase in inflammatory mediators, suppressed immune function, postoperative ileus, increased heart rate, increased skin conductance, increased sweat rate, and/or anxiety.

In an example, the detection, prediction, and/or determination described herein may be performed by a computing system based on measured data and/or related biomarkers generated by the autonomic tone sensing system. The autonomic tone sensing system may process the autonomic tone data locally or transmit the data to a processing unit.

A circadian rhythm sensing system may measure circadian rhythm data including light exposure, heart rate, core body temperature, cortisol levels, activity, and/or sleep. Based on the circadian rhythm data the circadian rhythm sensing system may detect circadian rhythm-related biomarkers, complications, and/or contextual information including sleep cycle, wake cycle, circadian patterns, disruption in circadian rhythm, and/or hormonal activity.

For example, based on the measured circadian rhythm data, the circadian rhythm sensing system may calculate the start and end of the circadian cycle. The circadian rhythm sensing system may indicate the beginning of the circadian day based on measured cortisol. Cortisol levels may peak at the start of a circadian day. The circadian rhythm sensing system may indicate the end of the circadian day based on measured heart rate and/or core body temperature. Heart rate and/or core body temperature may drop at the end of a circadian day. Based on the circadian rhythm-related biomarkers, the sensing system or processing unit may detect conditions including risk of infection and/or pain. For example, disrupted circadian rhythm may indicate pain and discomfort.

In an example, the detection, prediction, and/or determination described herein may be performed by a computing system based on measured data and/or related biomarkers generated by the circadian rhythm sensing system. The circadian rhythm sensing system may process the circadian rhythm data locally or transmit the data to a processing unit.

A menstrual cycle sensing system may measure menstrual cycle data including heart rate, heart rate variability, respiration rate, body temperature, and/or skin perfusion. Based on the menstrual cycle data, the menstrual cycle unit may indicate menstrual cycle-related biomarkers, complications, and/or contextual information, including menstrual cycle phase. For example, the menstrual cycle sensing system may detect the periovulatory phase in the menstrual cycle based on measured heart rate variability. Changes in heart rate variability may indicate the periovulatory phase. For example, the menstrual cycle sensing system may detect the luteal phase in the menstrual cycle based on measured wrist skin temperature and/or skin perfusion. Increased wrist skin temperature may indicate the luteal phase. Changes in skin perfusion may indicate the luteal phase. For example, the menstrual cycle sensing system may detect the ovulatory phase based on measured respiration rate. Low respiration rate may indicate the ovulatory phase.

Based on menstrual cycle-related biomarkers, the menstrual cycle sensing system may determine conditions including hormonal changes, surgical bleeding, scarring, bleeding risk, and/or sensitivity levels. For example, the menstrual cycle phase may affect surgical bleeding in rhinoplasty. For example, the menstrual cycle phase may affect healing and scarring in breast surgery. For example, bleeding risk may decrease during the periovulatory phase in the menstrual cycle.

In an example, the detection, prediction, and/or determination described herein may be performed by a computing system based on measured data and/or related biomarkers generated by the menstrual cycle sensing system. The menstrual cycle sensing system may locally process menstrual cycle data or transmit the data to a processing unit.

An environmental sensing system may measure environmental data including environmental temperature, humidity, mycotoxin spore count, and airborne chemical data. The environmental sensing system may include a digital thermometer, air sampling, and/or chemical sensors. The sensing system may include a wearable device. The environmental sensing system may use a digital thermometer to measure environmental temperature and/or humidity. The digital thermometer may include a metal strip with a determined resistance. The resistance of the metal strip may vary with environmental temperature. The digital thermometer may apply the varied resistance to a calibration curve to determine temperature. The digital thermometer may include a wet bulb and a dry bulb. The wet bulb and dry bulb may determine a difference in temperature, which then may be used to calculate humidity.

The environmental sensing system may use air sampling to measure mycotoxin spore count. The environmental sensing system may include a sampling plate with adhesive media connected to a pump. The pump may draw air over the plate over set time at a specific flow rate. The set time may last up to 10 minutes. The environmental sensing system may analyze the sample using a microscope to count the number of spores. The environmental sensing system may use different air sampling techniques including high-performance liquid chromatography (HPLC), liquid chromatography-tandem mass spectrometry (LC-MS/MS), and/or immunoassays and nanobodies.

The environmental sensing system may include chemical sensors to measure airborne chemical data. Airborne chemical data may include different identified airborne chemicals, including nicotine and/or formaldehyde. The chemical sensors may include an active layer and a transducer layer. The active layer may allow chemicals to diffuse into a matrix and alter some physical or chemical property. The changing physical property may include refractive index and/or H-bond formation. The transducer layer may convert the physical and/or chemical variation into a measurable signal, including an optical or electrical signal. The environmental sensing system may include a handheld instrument. The handheld instrument may detect and identify complex chemical mixtures that constitute aromas, odors, fragrances, formulations, spills, and/or leaks. The handheld instrument may include an array of nanocomposite sensors. The handheld instrument may detect and identify substances based on chemical profile.

Based on the environmental data, the sensing system may determine environmental information including climate, mycotoxin spore count, mycotoxin identification, airborne chemical identification, airborne chemical levels, and/or inflammatory chemical inhalation. For example, the environmental sensing system may approximate the mycotoxin spore count in the air based on the measured spore count from a collected sample. The sensing system may identify the mycotoxin spores which may include molds, pollens, insect parts, skin cell fragments, fibers, and/or inorganic particulate. For example, the sensing system may detect inflammatory chemical inhalation, including cigarette smoke. The sensing system may detect second-hand or third-hand smoke.

Based on the environmental information, the sensing system may generate environmental aspects conditions including inflammation, reduced lung function, airway hyper-reactivity, fibrosis, and/or reduce immune functions. For example, the environmental aspects sensing system may detect inflammation and fibrosis based on the measured environmental aspects information. The sensing system may generate instructions for a surgical tool, including a staple and sealing tool used in lung segmentectomy, based on the inflammation and/or fibrosis. Inflammation and fibrosis may affect the surgical tool usage. For example, cigarette smoke may cause higher pain scores in various surgeries.

The environmental sensing system may generate an air quality score based on the measured mycotoxins and/or airborne chemicals. For example, the environmental sensing system may notify about hazardous air quality if it detects a poor air quality score. The environmental sensing system may send a notification when the generated air quality score falls below a certain threshold. The threshold may include exposure exceeding 105 spores of mycotoxins per cubic meter. The environmental sensing system may display a readout of the environment condition exposure over time.

The environmental sensing system may locally process environmental data or transmit the data to a processing unit. In an example, the detection, prediction, and/or determination described herein may be performed by a computing system based on measured data generated by the environmental sensing system.

A light exposure sensing system may measure light exposure data. The light exposure sensing system may include one or more photodiode light sensors. For example, the light exposure sensing system using photodiode light sensors may include a semiconductor device in which the device current may vary as a function of light intensity. Incident photons may create electron-hole pairs that flow across the semiconductor junction, which may create current. The rate of electron-hole pair generation may increase as a function of the intensity of the incident light. The light exposure sensing system may include one or more photoresistor light sensors. For example, the light exposure sensing system using photoresistor light sensors may include a light-dependent resistor in which the resistance decreases as a function of light intensity. The photoresistor light sensor may include passive devices without a PN-junction. The photoresistor light sensors may be less sensitive than photodiode light sensors. The light exposure sensing system may include a wearable, including a necklace and/or clip-on button.

Based on the measured light exposure data, the light exposure sensing system may detect light exposure information including exposure duration, exposure intensity, and/or light type. For example, the sensing system may determine whether light exposure consists of natural light or artificial light. Based on the detected light exposure information, the light exposure sensing system may detect light exposure-related biomarker(s) including circadian rhythm. Light exposure may entrain the circadian cycle.

The light exposure sensing system may locally process the light exposure data or transmit the data to a processing unit. In an example, the detection, prediction, and/or determination described herein may be performed by a computing system based on measured data and/or related biomarkers generated by the light exposure sensing system.

The various sensing systems described herein may measure data, derive related biomarkers, and send the biomarkers to a computing system, such as a surgical hub as described herein with reference to FIGS. 1-12. The various sensing systems described herein may send the measured data to the computing system. The computing system may derive the related biomarkers based on the received measurement data.

The biomarker sensing systems may include a wearable device. In an example, the biomarker sensing system may include eyeglasses. The eyeglasses may include a nose pad sensor. The eyeglasses may measure biomarkers, including lactate, glucose, and/or the like. In an example, the biomarker sensing system may include a mouthguard. The mouthguard may include a sensor to measure biomarkers including uric acid and/or the like. In an example, the biomarker sensing system may include a contact lens. The contact lens may include a sensor to measure biomarkers including glucose and/or the like. In an example, the biomarker sensing system may include a tooth sensor. The tooth sensor may be graphene-based. The tooth sensor may measure biomarkers including bacteria and/or the like. In an example, the biomarker sensing system may include a patch. The patch may be wearable on the chest skin or arm skin. For example, the patch may include a chem-phys hybrid sensor. The chem-phys hybrid sensor may measure biomarkers including lactate, ECG, and/or the like. For example, the patch may include nanomaterials. The nanomaterials patch may measure biomarkers including glucose and/or the like. For example, the patch may include an iontophoretic biosensor. The iontophoretic biosensor may measure biomarkers including glucose and/or the like. In an example, the biomarker sensing system may include a microfluidic sensor. The microfluidic sensor may measure biomarkers including lactate, glucose, and/or the like. In an example, the biomarker sensing system may include an integrated sensor array. The integrated sensory array may include a wearable wristband. The integrated sensory array may measure biomarkers including lactate, glucose, and/or the like. In an example, the biomarker sensing system may include a wearable diagnostics device. The wearable diagnostic device may measure biomarkers including cortisol, interleukin-6, and/or the like. In an example, the biomarker sensing system may include a self-powered textile-based biosensor. The self-powered textile-based biosensor may include a sock. The self-powered textile-based biosensor may measure biomarkers including lactate and/or the like.

The various biomarkers described herein may be related to various physiologic systems, including behavior and psychology, cardiovascular system, renal system, skin system, nervous system, GI system, respiratory system, endocrine system, immune system, tumor, musculoskeletal system, and/or reproductive system.

Behavior and psychology may include social interactions, diet, sleep, activity, and/or psychological status. Behavior and psychology-related biomarkers, complications, contextual information, and/or conditions may be determined and/or predicted based on analyzed biomarker sensing systems data. A computing system, as described herein, may select one or more biomarkers (e.g., data from biomarker sensing systems) from behavior and psychology-related biomarkers, including sleep, circadian rhythm, physical activity, and/or mental aspects for analysis. Behavior and psychology scores may be generated based on the analyzed biomarkers, complications, contextual information, and/or conditions. Behavior and psychology scores may include scores for social interaction, diet, sleep, activity, and/or psychological status.

For example, based on the selected biomarker sensing systems data, sleep-related biomarkers, complications, and/or contextual information may be determined, including sleep quality, sleep duration, sleep timing, immune function, and/or post-operation pain. Based on the selected biomarker sensing systems data, sleep-related conditions may be predicted, including inflammation. In an example, inflammation may be predicted based on analyzed pre-operation sleep. Elevated inflammation may be determined and/or predicted based on disrupted pre-operation sleep. In an example, immune function may be determined based on analyzed pre-operation sleep. Reduced immune function may be predicted based on disrupted pre-operation sleep. In an example, post-operation pain may be determined based on analyzed sleep. Post-operation pain may be determined and/or predicted based on disrupted sleep. In an example, pain and discomfort may be determined based on analyzed circadian rhythm. A compromised immune system may be determined based on analyzed circadian rhythm cycle disruptions.

For example, based on the selected biomarker sensing systems data, activity-related biomarkers, complications, and/or contextual information may be determined, including activity duration, activity intensity, activity type, activity pattern, recovery time, mental health, physical recovery, immune function, and/or inflammatory function. Based on the selected biomarker sensing systems data, activity-related conditions may be predicted. In an example, improved physiology may be determined based on analyzed activity intensity. Moderate intensity exercise may indicate shorter hospital stays, better mental health, better physical recovery, improved immune function, and/or improved inflammatory function. Physical activity type may include aerobic activity and/or non-aerobic activity. Aerobic physical activity may be determined based on analyzed physical activity, including running, cycling, and/or weight training. Non-aerobic physical activity may be determined based on analyzed physical activity, including walking and/or stretching.

For example, based on the selected biomarker sensing systems data, psychological status-related biomarkers, complications, and/or contextual information may be determined, including stress, anxiety, pain, positive emotions, abnormal states, and/or post-operative pain. Based on the selected biomarker sensing systems data, psychological status-related conditions may be predicted, including physical symptoms of disease. Higher post-operative pain may be determined and/or predicted based on analyzed high levels of pre-operative stress, anxiety, and/or pain. Physical symptoms of disease may be predicted based on determined high optimism.

The detection, prediction, determination, and/or generation described herein may be performed by a computing system described herein, such as a surgical hub, a computing device, and/or a smart device based on measured data and/or related biomarkers generated by the biomarker sensing systems.

The cardiovascular system may include the lymphatic system, blood vessels, blood, and/or heart. Cardiovascular system-related biomarkers, complications, contextual information, and/or conditions may be determined and/or predicted based on analyzed biomarker sensing systems data. Systemic circulation conditions may include conditions for the lymphatic system, blood vessels, and/or blood. A computing system may select one or more biomarkers (e.g., data from biomarker sensing systems) from cardiovascular system-related biomarkers, including blood pressure, VO2 max, hydration state, oxygen saturation, blood pH, sweat, core body temperature, peripheral temperature, edema, heart rate, and/or heart rate variability for analysis.

For example, based on the selected biomarker sensing systems data, lymphatic system-related biomarkers, complications, and/or contextual information may be determined, including swelling, lymph composition, and/or collagen deposition. Based on the selected biomarker sensing systems data, lymphatic system-related conditions may be predicted, including fibrosis, inflammation, and/or post-operation infection. Inflammation may be predicted based on determined swelling. Post-operation infection may be predicted based on determined swelling. Collagen deposition may be determined based on predicted fibrosis. Increased collagen deposition may be predicted based on fibrosis. Harmonic tool parameter adjustments may be generated based on determined collagen deposition increases. Inflammatory conditions may be predicted based on analyzed lymph composition. Different inflammatory conditions may be determined and/or predicted based on changes in lymph peptidome composition. Metastatic cell spread may be predicted based on predicted inflammatory conditions. Harmonic tool parameter adjustments and margin decisions may be generated based on predicted inflammatory conditions.

For example, based on the selected biomarker sensing systems data, blood vessel-related biomarkers, complications, and/or contextual information may be determined, including permeability, vasomotion, pressure, structure, healing ability, harmonic sealing performance, and/or cardiothoracic health fitness. Surgical tool usage recommendations and/or parameter adjustments may be generated based on the determined blood vessel-related biomarkers. Based on the selected biomarker sensing systems data, blood vessel-related conditions may be predicted, including infection, anastomotic leak, septic shock and/or hypovolemic shock. In an example, increased vascular permeability may be determined based on analyzed edema, bradykinin, histamine, and/or endothelial adhesion molecules. Endothelial adhesion molecules may be measured using cell samples to measure transmembrane proteins. In an example, vasomotion may be determined based on selected biomarker sensing systems data. Vasomotion may include vasodilators and/or vasoconstrictors. In an example, shock may be predicted based on the determined blood pressure-related biomarkers, including vessel information and/or vessel distribution. Individual vessel structure may include arterial stiffness, collagen content, and/or vessel diameter. Cardiothoracic health fitness may be determined based on VO2 max. Higher risk of complications may be determined and/or predicted based on poor VO2 max.

For example, based on the selected biomarker sensing systems data, blood-related biomarkers, complications, and/or contextual information may be determined, including volume, oxygen, pH, waste products, temperature, hormones, proteins, and/or nutrients. Based on the selected biomarker sensing systems data, blood-related complications and/or contextual information may be determined, including cardiothoracic health fitness, lung function, recovery capacity, anaerobic threshold, oxygen intake, carbon dioxide ($CO_2$) production, fitness, tissue oxygenation, colloid osmotic pressure, and/or blood clotting ability. Based on derived blood-related biomarkers, blood-related conditions may be predicted, including post-operative acute kidney injury, hypovolemic shock, acidosis, sepsis, lung collapse, hemorrhage, bleeding risk, infection, and/or anastomotic leak.

For example, post-operative acute kidney injury and/or hypovolemic shock may be predicted based on the hydration state. For example, lung function, lung recovery capacity, cardiothoracic health fitness, anaerobic threshold, oxygen uptake, and/or $CO_2$ product may be predicted based on the blood-related biomarkers, including red blood cell count and/or oxygen saturation. For example, cardiovascular complications may be predicted based on the blood-related biomarkers, including red blood cell count and/or oxygen saturation. For example, acidosis may be predicted based on the pH. Based on acidosis, blood-related conditions may be indicated, including sepsis, lung collapse, hemorrhage, and/or increased bleeding risk. For example, based on sweat, blood-related biomarkers may be derived, including tissue oxygenation. Insufficient tissue oxygenation may be predicted based on high lactate concentration. Based on insufficient tissue oxygenation, blood-related conditions may be predicted, including hypovolemic shock, septic shock, and/or left ventricular failure. For example, based on the temperature, blood temperature-related biomarkers may be derived, including menstrual cycle and/or basal temperature. Based on the blood temperature-related biomarkers, blood temperature-related conditions may be predicted, including sepsis and/or infection. For example, based on proteins, including albumin content, colloid osmotic pressure may be determined. Based on the colloid osmotic pressure, blood protein-related conditions may be predicted, including edema risk and/or anastomotic leak. Increased edema risk and/or anastomotic leak may be predicted based on low colloid osmotic pressure. Bleeding risk may be predicted based on blood clotting ability. Blood clotting ability may be determined based on fibrinogen content. Reduced blood clotting ability may be determined based on low fibrinogen content.

For example, based on the selected biomarker sensing systems data, the computing system may derive heart-related biomarkers, complications, and/or contextual information, including heart activity, heart anatomy, recovery rates, cardiothoracic health fitness, and/or risk of complications. Heart activity biomarkers may include electrical activity and/or stroke volume. Recovery rate may be determined based on heart rate biomarkers. Reduced blood supply to the body may be determined and/or predicted based on irregular heart rate. Slower recovery may be determined and/or predicted based on reduced blood supply to the body. Cardiothoracic health fitness may be determined based on analyzed VO2 max values. VO2 max values below a certain threshold may indicate poor cardiothoracic health fitness. VO2 max values below a certain threshold may indicate a higher risk of heart-related complications.

The detection, prediction, determination, and/or generation described herein may be performed by a computing system described herein, such as a surgical hub, a computing device, and/or a smart device, based on measured data and/or related biomarkers generated by the biomarker sensing systems.

Renal system-related biomarkers, complications, contextual information, and/or conditions may be determined and/or predicted based on analyzed biomarker sensing systems data. A computing system, as described herein, may select one or more biomarkers (e.g., data from biomarker sensing systems) from renal system-related biomarkers for analysis. Based on the selected biomarker sensing systems data, renal system-related biomarkers, complications, and/or contextual information may be determined including ureter, urethra, bladder, kidney, general urinary tract, and/or ureter fragility. Based on the selected biomarker sensing systems data, renal system-related conditions may be predicted, including acute kidney injury, infection, and/or kidney stones. In an example, ureter fragility may be determined based on urine inflammatory parameters. In an example, acute kidney injury may be predicted based on analyzed Kidney Injury Molecule-1 (KIM-1) in urine.

The detection, prediction, determination, and/or generation described herein may be performed by a computing system described herein, such as a surgical hub, a computing device, and/or a smart device based on measured data and/or related biomarkers generated by the biomarker sensing systems.

The skin system may include biomarkers relating to microbiome, skin, nails, hair, sweat, and/or sebum. Skin-related biomarkers may include epidermis biomarkers and/or dermis biomarkers. Sweat-related biomarkers may include activity biomarkers and/or composition biomarkers. Skin system-related biomarkers, complications, contextual information, and/or conditions may be determined and/or predicted based on analyzed biomarker sensing systems data. A computing system, as described herein, may select one or more biomarkers (e.g., data from biomarker sensing systems) from skin-related biomarkers, including skin conductance, skin perfusion pressure, sweat, autonomic tone, and/or pH for analysis.

For example, based on selected biomarker sensing systems data, skin-related biomarkers, complications, and/or contextual information may be determined, including color, lesions, trans-epidermal water loss, sympathetic nervous system activity, elasticity, tissue perfusion, and/or mechanical properties. Stress may be predicted based on determined skin conductance. Skin conductance may act as a proxy for sympathetic nervous system activity. Sympathetic nervous system activity may correlate with stress. Tissue mechanical properties may be determined based on skin perfusion pressure. Skin perfusion pressure may indicate deep tissue perfusion. Deep tissue perfusion may determine tissue mechanical properties. Surgical tool parameter adjustments may be generated based on determined tissue mechanical properties.

Based on selected biomarker sensing systems data, skin-related conditions may be predicted.

For example, based on selected biomarker sensing systems data, sweat-related biomarkers, complications, and/or contextual information may be determined, including activity, composition, autonomic tone, stress response, inflammatory response, blood pH, blood vessel health, immune function, circadian rhythm, and/or blood lactate concentration. Based on selected biomarker sensing systems data, sweat-related conditions may be predicted, including ileus, cystic fibrosis, diabetes, metastasis, cardiac issues, and/or infections.

For example, sweat composition-related biomarkers may be determined based on selected biomarker data. Sweat composition biomarkers may include proteins, electrolytes, and/or small molecules. Based on the sweat composition biomarkers, skin system complications, conditions, and/or contextual information may be predicted, including ileus, cystic fibrosis, acidosis, sepsis, lung collapse, hemorrhage, bleeding risk, diabetes, metastasis, and/or infection. For example, based on protein biomarkers, including sweat neuropeptide Y and/or sweat antimicrobials, stress response may be predicted. Higher sweat neuropeptide Y levels may indicate greater stress response. Cystic fibrosis and/or acidosis may be predicted based on electrolyte biomarkers, including chloride ions, pH, and other electrolytes. High lactate concentrations may be determined based on blood pH. Acidosis may be predicted based on high lactate concentrations. Sepsis, lung collapse, hemorrhage, and/or bleeding risk may be predicted based on predicted acidosis. Diabetes, metastasis, and/or infection may be predicted based on small molecule biomarkers. Small molecule biomarkers may include blood sugar and/or hormones. Hormone biomarkers may include adrenaline and/or cortisol. Based on predicted metastasis, blood vessel health may be determined. Infection due to lower immune function may be predicted based on detected cortisol. Lower immune function may be determined and/or predicted based on high cortisol. For example, sweat-related conditions, including stress response, inflammatory response, and/or ileus, may be predicted based on determined autonomic tone. Greater stress response, greater inflammatory response, and/or ileus may be determined and/or predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

Nervous system-related biomarkers, complications, contextual information, and/or conditions may be determined and/or predicted based on analyzed biomarker sensing systems data. A computing system, as described herein, may select one or more biomarkers (e.g., data from biomarker sensing systems) from nervous system-related biomarkers, including circadian rhythm, oxygen saturation, autonomic tone, sleep, activity, and/or mental aspects for. The nervous system may include the central nervous system (CNS) and/or the peripheral nervous system. The CNS may include brain and/or spinal cord. The peripheral nervous system may include the autonomic nervous system, motor system, enteric system, and/or sensory system.

For example, based on the selected biomarker sensing systems data, CNS-related biomarkers, complications, and/or contextual information may be determined, including post-operative pain, immune function, mental health, and/or recovery rate. Based on the selected biomarker sensing systems data, CNS-related conditions may be predicted, including inflammation, delirium, sepsis, hyperactivity, hypoactivity, and/or physical symptoms of disease. In an example, a compromised immune system and/or high pain score may be predicted based on disrupted sleep. In an example, post-operation delirium may be predicted based on oxygen saturation. Cerebral oxygenation may indicate post-operation delirium.

For example, based on the selected biomarker sensing systems data, peripheral nervous system-related biomarkers, complications, and/or contextual information may be determined. Based on the selected biomarker sensing systems data, peripheral nervous system-related conditions may be predicted, including inflammation and/or ileus. In an example, high sympathetic tone may be predicted based on autonomic tone. Greater stress response may be predicted based on high sympathetic tone. Inflammation and/or ileus may be predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

The GI system may include the upper GI tract, lower GI tract, ancillary organs, peritoneal space, nutritional states, and microbiomes. The upper GI may include the mouth, esophagus, and/or stomach. The lower GI may include the small intestine, colon, and/or rectum. Ancillary organs may include pancreas, liver, spleen, and/or gallbladder. Peritoneal space may include mesentry and/or adipose blood vessels. Nutritional states may include short-term, long-term, and/or systemic. GI-related biomarkers, complications, contextual information, and/or conditions may be determined and/or predicted based on analyzed biomarker sensing systems data. A computing system, as described herein, may select one or more biomarkers (e.g., data from biomarker sensing systems) from GI-related biomarkers, including coughing and sneezing, respiratory bacteria, GI tract imaging/sensing, GI motility, pH, tissue perfusion pressure, environmental, and/or alcohol consumption for analysis.

The upper GI may include the mouth, esophagus, and/or stomach. For example, based on the selected biomarker sensing systems data, mouth and esophagus-related biomarkers, complications, and/or contextual information, may be determined, including stomach tissue properties, esophageal motility, colonic tissue change, bacteria presence, tumor size, tumor location, and/or tumor tension. Based on the selected biomarker sensing systems data, mouth and esophagus-related conditions may be predicted, including inflammation, surgical site infection (SSI), and/or gastro-esophageal disease. The mouth and esophagus may include mucosa, muscularis, lumen, and/or mechanical properties. Lumen biomarkers may include lumen contents, lumen microbial flora, and/or lumen size. In an example, inflammation may be predicted based on analyzed coughing biomarkers. Gastro-esophageal reflux disease may be predicted based on inflammation. Stomach tissue properties may be predicted based on gastro-esophageal disease. In an example, esophageal motility may be determined based on collagen content and/or muscularis function. In an example, changes to colonic tissue may be indicated based on salivary cytokines. Inflammatory bowel disease (IBD) may be predicted based on changes to colonic tissue. Salivary cytokines may increase in IBD. SSI may be predicted based on analyzed bacteria. Based on the analyzed bacteria, the bacteria may be identified. Respiratory pathogens in the mouth may indicate likelihood of SSI. Based on lumen size and/or location, surgical tool parameter adjustments may be generated. Surgical tool parameter adjustments may include staple sizing, surgical tool fixation, and/or surgical tool approach. In an example, based on mechanical properties, including elasticity, a surgical tool parameter adjustment to use adjunct material may be generated to minimize tissue tension. Additional mobilization parameter adjustments may be generated to minimize tissue tension based on analyzed mechanical properties.

For example, based on the selected biomarker sensing systems data, stomach-related biomarkers, complications, and/or contextual information, may be determined including tissue strength, tissue thickness, recovery rate, lumen location, lumen shape, pancreas function, stomach food presence, stomach water content, stomach tissue thickness, stomach tissue shear strength, and/or stomach tissue elasticity. Based on the selected biomarker sensing systems data, stomach-related conditions may be predicted, including ulcer, inflammation, and/or gastro-esophageal reflux disease. The stomach may include mucosa, muscularis, serosa, lumen, and mechanical properties. Stomach-related conditions, including ulcers, inflammation, and/or gastro-esophageal disease may be predicted based on analyzed coughing and/or GI tract imaging. Stomach tissue properties may be determined based on gastro-esophageal reflux disease. Ulcers may be predicted based on analyzed *H. pylori*. Stomach tissue mechanical properties may be determined based on GI tract images. Surgical tool parameter adjustments may be generated based on the determined stomach tissue mechanical properties. Risk of post-operative leak may be predicted based on determined stomach tissue mechanical properties. In an example, key components for tissue strength and/or thickness may be determined based on analyzed collagen content. Key components of tissue strength and thickness may affect recovery. In an example, blood supply and/or blood location may be determined based on serosa biomarkers. In an example, biomarkers, including pouch size, pouch volume, pouch location, pancreas function, and/or food presence may be determined based on analyzed lumen biomarkers. Lumen biomarkers may include lumen location, lumen shape, gastric emptying speed, and/or lumen contents. Pouch size may be determined based on start and end locations of the pouch. Gastric emptying speed may be determined based on GI motility. Pancreas function may be determined based on gastric emptying speed. Lumen content may be determined based on analyzed gastric pH. Lumen content may include stomach food presence. For example, solid food presence may be determined based on gastric pH variation. Low gastric pH may be predicted based on an empty stomach. Basic gastric pH may be determined based on eating. Buffering by food may lead to basic gastric pH. Gastric pH may increase based on stomach acid secretion. Gastric pH may return to low value when the buffering capacity of food is exceeded. Intraluminal pH sensors may detect eating. For example, stomach water content, tissue thickness, tissue shear strength, and/or tissue elasticity may be determined based on tissue perfusion pressure. Stomach mechanical properties may be determined based on stomach water content. Surgical tool parameter adjustments may be generated based on the stomach mechanical properties. Surgical tool parameter adjustments may be generated based on key components of tissue strength and/or friability. Post-surgery leakage may be predicted based on key components of tissue strength and/or friability.

The lower GI may include the small intestine, colon, and/or rectum. For example, based on the selected biomarker sensing systems data, small intestine-related biomarkers, complications, contextual information, and/or conditions may be determined, including caloric absorption rate, nutrient absorption rate, bacteria presence, and/or recovery rate. Based on the selected biomarker sensing systems data, small intestine-related conditions may be predicted, including ileus and/or inflammation. The small intestine biomarkers may include muscularis, serosa, lumen, mucosa, and/or mechanical properties. For example, post-operation small bowel motility changes may be determined based on GI motility. Ileus may be predicted based on post-operation small bowel motility changes. GI motility may determine caloric and/or nutrient absorption rates. Future weight loss may be predicted based on accelerated absorption rates. Absorption rates may be determined based on fecal rates, composition, and/or pH. Inflammation may be predicted based on lumen content biomarkers. Lumen content biomarkers may include pH, bacteria presence, and/or bacteria amount. Mechanical properties may be determined based on predicted inflammation. Mucosa inflammation may be predicted based on stool inflammatory markers. Stool inflammatory markers may include calprotectin. Tissue property changes may be determined based on mucosa inflammation. Recovery rate changes may be determined based on mucosa inflammation.

For example, based on the selected biomarker sensing systems data, colon and rectum-related biomarkers, complications, and/or contextual information may be determined, including small intestine tissue strength, small intestine tissue thickness, contraction ability, water content, colon and rectum tissue perfusion pressure, colon and rectum tissue thickness, colon and rectum tissue strength, and/or colon and rectum tissue friability. Based on the selected biomarker sensing systems data, colon and rectum-related conditions may be predicted, including inflammation, anastomotic leak, ulcerative colitis, Crohn's disease, and/or infection. Colon and rectum may include mucosa, muscularis, serosa, lumen, function, and/or mechanical properties. In an example, mucosa inflammation may be predicted based on stool inflammatory markers. Stool inflammatory markers may include calprotectin. An increase in anastomotic leak risk may be determined based on inflammation.

Surgical tool parameter adjustments may be generated based on the determined increased risk of anastomotic leak. Inflammatory conditions may be predicted based on GI tract imaging. Inflammatory conditions may include ulcerative colitis and/or Crohn's disease. Inflammation may increase the risk of anastomotic leak. Surgical tool parameter adjustments may be generated based on inflammation. In an example, the key components of tissue strength and/or thickness may be determined based on collagen content. In an example, colon contraction ability may be determined based on smooth muscle alpha-actin expression. In an example, the inability of colon areas to contract may be determined based on abnormal expression. Colon contraction inability may be determined and/or predicted based on pseudo-obstruction and/or ileus. In an example, adhesions, fistula, and/or scar tissue may be predicted based on serosa biomarkers. Colon infection may be predicted based on bacterial presence in stool. The stool bacteria may be identified. The bacteria may include commensals and/or pathogens. In an example, inflammatory conditions may be predicted based on pH. Mechanical properties may be determined based on inflammatory conditions. Gut inflammation may be predicted based on ingested allergens. Constant exposure to ingested allergens may increase gut inflammation. Gut inflammation may change mechanical properties. In an example, mechanical properties may be determined based on tissue perfusion pressure. Water content may be determined based on tissue perfusion pressure. Surgical tool parameter adjustments may be generated based on determined mechanical properties.

Ancillary organs may include the pancreas, liver, spleen, and/or gallbladder. Based on the selected biomarker sensing systems data, ancillary organ-related biomarkers, complications, and/or contextual information may be determined including gastric emptying speed, liver size, liver shape, liver location, tissue health, and/or blood loss response. Based on the selected biomarker sensing systems data, ancillary organ-related conditions may be predicted, including gastroparesis. For example, gastric emptying speed may be determined based on enzyme load and/or titratable base biomarkers. Gastroparesis may be predicted based on gastric emptying speed. Lymphatic tissue health may be determined based on lymphocyte storage status. A patient's ability to respond to an SSI may be determined based on lymphatic tissue health. Venous sinuses tissue health may be determined based on red blood cell storage status. A patient's response to blood loss in surgery may be predicted based on venous sinuses tissue health.

Nutritional states may include short-term nutrition, long-term nutrition, and/or systemic nutrition. Based on the selected biomarker sensing systems data, nutritional state-related biomarkers, complications, and/or contextual information may be determined, including immune function. Based on the selected biomarker sensing systems data, nutritional state-related conditions may be predicted, including cardiac issues. Reduced immune function may be determined based on nutrient biomarkers. Cardiac issues may be predicted based on nutrient biomarkers. Nutrient biomarkers may include macronutrients, micronutrients, alcohol consumption, and/or feeding patterns.

Patients who have had gastric bypass may have an altered gut microbiome that may be measured in the feces.

The detection, prediction, determination, and/or generation described herein may be performed by a computing system described herein, such as a surgical hub, a computing device, and/or a smart device based on measured data and/or related biomarkers generated by the biomarker sensing systems.

The respiratory system may include the upper respiratory tract, lower respiratory tract, respiratory muscles, and/or system contents. The upper respiratory tract may include the pharynx, larynx, mouth and oral cavity, and/or nose. The lower respiratory tract may include the trachea, bronchi, aveoli, and/or lungs. The respiratory muscles may include the diaphragm and/or intercostal muscles. Respiratory system-related biomarkers, complications, contextual information, and/or conditions may be determined and/or predicted based on analyzed biomarker sensing systems data. A computing system, as described herein, may select one or more biomarkers (e.g., data from biomarker sensing systems) from respiratory system-related biomarkers, including bacteria, coughing and sneezing, respiration rate, VO2 max, and/or activity for analysis.

The upper respiratory tract may include the pharynx, larynx, mouth and oral cavity, and/or nose. For example, based on the selected biomarker sensing systems data, upper respiratory tract-related biomarkers, complications, and/or contextual information may be determined. Based on the selected biomarker sensing systems data, upper respiratory tract-related conditions may be predicted, including SSI, inflammation, and/or allergic rhinitis. In an example, SSI may be predicted based on bacteria and/or tissue biomarkers. Bacteria biomarkers may include commensals and/or pathogens. Inflammation may be indicated based on tissue biomarkers. Mucosa inflammation may be predicted based on nose biomarkers, including coughing and sneezing. General inflammation and/or allergic rhinitis may be predicted based on mucosa biomarkers. Mechanical properties of various tissues may be determined based on systemic inflammation.

The lower respiratory tract may include the trachea, bronchi, aveoli, and/or lungs. For example, based on the selected biomarker sensing systems data, lower respiratory tract-related biomarkers, complications, and/or contextual information may be determined, including bronchopulmonary segments. Based on the selected biomarker sensing systems data, lower respiratory tract-related conditions may be predicted. Surgical tool parameter adjustments may be generated based on the determined biomarkers, complications, and/or contextual information. Surgical tool parameter adjustments may be generated based on the predicted conditions.

Based on the selected biomarker sensing systems data, lung-related biomarkers, complications, and/or contextual information may be determined, including poor surgical tolerance. Lung-related biomarkers may include lung respiratory mechanics, lung disease, lung surgery, lung mechanical properties, and/or lung function. Lung respiratory mechanics may include total lung capacity (TLC), tidal volume (TV), residual volume (RV), expiratory reserve volume (ERV), inspiratory reserve volume (IRV), inspiratory capacity (IC), inspiratory vital capacity (IVC), vital capacity (VC), functional residual capacity (FRC), residual volume expressed as a percent of total lung capacity (RV/TLC %), alveolar gas volume (VA), lung volume (VL), forced vital capacity (FVC), forced expiratory volume over time (FEVt), difference between inspired and expired carbon monoxide (DLco), volume exhaled after first second of forced expiration (FEV1), forced expiratory flow related to portion of functional residual capacity curve (FEFx), maximum instantaneous flow during functional residual capacity (FEFmax), forced inspiratory flow (FIF), highest forced expiratory flow measured by peak flow meter (PEF), and maximal voluntary ventilation (MVV).

TLC may be determined based on lung volume at maximal inflation. TV may be determined based on volume of air moved into or out of the lungs during quiet breathing. RV may be determined based on air volume remaining in lungs after a maximal exhalation. ERV may be determined based on maximal volume inhaled from the end-inspiratory level. IC may be determined based on aggregated IRV and TV values. IVC may be determined based on maximum air volume inhaled at the point of maximum expiration. VC may be determined based on the difference between the RV value and TLC value. FRC may be determined based on the lung volume at the end-expiratory position. FVC may be determined based on the VC value during a maximally forced expiratory effort. Poor surgical tolerance may be determined based on the difference between inspired and expired carbon monoxide, such as when the difference falls below 60%. Poor surgical tolerance may be determined based on the volume exhaled at the end of the first second of force expiration, such as when the volume falls below 35%. MVV may be determined based on the volume of air expired in a specified period during repetitive maximal effort.

Based on the selected biomarker sensing systems data, lung-related conditions may be predicted, including emphysema, chronic obstructive pulmonary disease, chronic bronchitis, asthma, cancer, and/or tuberculosis. Lung diseases may be predicted based on analyzed spirometry, x-rays, blood gas, and/or diffusion capacity of the aveolar capillary membrane. Lung diseases may narrow airways and/or create airway resistance. Lung cancer and/or tuberculosis may be detected based on lung-related biomarkers, including persistent coughing, coughing blood, shortness of breath, chest pain, hoarseness, unintentional weight loss, bone pain, and/or headaches. Tuberculosis may be predicted based on lung symptoms including coughing for 3 to 5 weeks, coughing blood, chest pain, pain while breathing or coughing, unintentional weight loss, fatigue, fever, night sweats, chills, and/or loss of appetite.

Surgical tool parameter adjustments and surgical procedure adjustments may be generated based on lung-related biomarkers, complications, contextual information, and/or conditions. Surgical procedure adjustments may include pneumonectomy, lobectomy, and/or sub-local resections. In an example, a surgical procedure adjustment may be generated based on a cost-benefit analysis between adequate resection and the physiologic impact on a patient's ability to recover functional status. Surgical tool parameter adjustments may be generated based on determined surgical tolerance. Surgical tolerance may be determined based on the FEC1 value. Surgical tolerance may be considered adequate when FEV1 exceeds a certain threshold, which may include values above 35%. Post-operation surgical procedure adjustments, including oxygenation and/or physical therapy, may be generated based on determined pain scores. Post-operation surgical procedure adjustments may be generated based on air leak. Air leak may increase cost associated with the post-surgical recovery and morbidity following lung surgery.

Lung mechanical property-related biomarkers may include perfusion, tissue integrity, and/or collagen content. Plura perfusion pressure may be determined based on lung water content levels. Mechanical properties of tissue may be determined based on plura perfusion pressure. Surgical tool parameter adjustments may be generated based on plura perfusion pressure. Lung tissue integrity may be determined based on elasticity, hydrogen peroxide ($H_2O_2$) in exhaled breath, lung tissue thickness, and/or lung tissue shear strength. Tissue friability may be determined based on elasticity. Surgical tool parameter adjustments may be generated based on post-surgery leakage. Post-surgery leakage may be predicted based on elasticity. In an example, fibrosis may be predicted based on $H_2O_2$ in exhaled breath. Fibrosis may be determined and/or predicted based on increased $H_2O_2$ concentration. Surgical tool parameter adjustments may be generated based on predicted fibrosis. Increased scarring in lung tissue may be determined based on predicted fibrosis. Surgical tool parameter adjustments may be generated based on determined lung tissue strength. Lung tissue strength may be determined based on lung thickness and/or lung tissue shear strength. Post-surgery leakage may be predicted based on lung tissue strength.

Respiratory muscles may include the diaphragm and/or intercostal muscles. Based on the selected biomarker sensing systems data, respiratory muscle-related biomarkers, complications, and/or contextual information may be determined. Based on the selected biomarker sensing systems data, respiratory muscle-related conditions may be predicted, including respiratory tract infections, collapsed lung, pulmonary edema, post-operation pain, air leak, and/or serious lung inflammation. Respiratory muscle-related conditions, including respiratory tract infections, collapsed lung, and/or pulmonary edema, may be predicted based on diaphragm-related biomarkers, including coughing and/or sneezing. Respiratory muscle-related conditions, including post-operation pain, air leak, collapsed lung, and/or serious lung inflammation may be predicted based on intercostal muscle biomarkers, including respiratory rate.

Based on the selected biomarker sensing systems data, respiratory system content-related biomarkers, complications, and/or contextual information may be determined, including post-operation pain, healing ability, and/or response to surgical injury. Based on the selected biomarker sensing systems data, respiratory system content-related conditions may be predicted, including inflammation and/or fibrosis. The selected biomarker sensing systems data may include environmental data, including mycotoxins and/or airborne chemicals. Respiratory system content-related conditions may be predicted based on airborne chemicals. Inflammation and/or fibrosis may be predicted based on irritants in the environment. Mechanical properties of tissue may be determined based on inflammation and/or fibrosis. Post-operation pain may be determined based on irritants in the environment. Airway inflammation may be predicted based on analyzed mycotoxins and/or arsenic. Surgical tool parameter adjustments may be generated based on airway inflammation. Altered tissue properties may be determined based on analyzed arsenic.

The detection, prediction, determination, and/or generation described herein may be performed by a computing system described herein, such as a surgical hub, a computing system, and/or a smart device based on measured data and/or related biomarkers generated by the biomarker sensing systems.

The endocrine system may include the hypothalamus, pituitary gland, thymus, adrenal gland, pancreas, testes, intestines, ovaries, thyroid gland, parathyroid, and/or stomach. Endocrine system-related biomarkers, complications, and/or contextual information may be determined based on analyzed biomarker sensing systems data, including immune system function, metastasis, infection risk, insulin secretion, collagen production, menstrual phase, and/or high blood pressure. Endocrine system-related conditions may be predicted based on analyzed biomarker sensing systems data. A computing system, as described herein, may select one or more biomarkers (e.g., data from biomarker sensing systems) from endocrine system-related biomarkers, including hormones, blood pressure, adrenaline, cortisol, blood glucose, and/or menstrual cycle for analysis. Surgical tool parameter adjustments and/or surgical procedure adjustments may be generated based on the endocrine system-related biomarkers, complications, contextual information, and/or conditions.

For example, based on the selected biomarker sensing systems data, hypothalamus-related biomarkers, complications, and/or contextual information may be determined, including blood pressure regulation, kidney function, osmotic balance, pituitary gland control, and/or pain tolerance. Based on the selected biomarker sensing systems data, hypothalamus-related conditions may be predicted, including edema. The hormone biomarkers may include anti-diuretic hormone (ADH) and/or oxytocin. ADH may affect blood pressure regulation, kidney function, osmotic balance, and/or pituitary gland control. Pain tolerance may be determined based on analyzed oxytocin. Oxytocin may have an analgesic effect. Surgical tool parameter adjustments may be generated based on predicted edema.

For example, based on the selected biomarker sensing systems data, pituitary gland-related biomarkers, complications, and/or contextual information may be determined, including circadian rhythm entrainment, menstrual phase, and/or healing speed. Based on the selected biomarker sensing systems data, pituitary gland-related conditions may be predicted. Circadian entrainment may be determined based on adrenocorticotropic hormones (ACTH). Circadian rhythm entrainment may provide context for various surgical outcomes. Menstrual phase may be determined based on reproduction function hormone biomarkers. Reproduction function hormone biomarkers may include luteinizing hormone and/or follicle stimulating hormone. Menstrual phase may provide context for various surgical outcomes. The menstrual cycle may provide context for biomarkers, complications, and/or conditions, including those related to the reproductive system. Wound healing speed may be determined based on thyroid regulation hormones, including thyrotropic releasing hormone (TRH).

For example, based on the selected biomarker sensing systems data, thymus-related biomarkers, complications, and/or contextual information may be determined, including immune system function. Based on the selected biomarker sensing systems data, thymus-related conditions may be predicted. Immune system function may be determined based on thymosins. Thymosins may affect adaptive immunity development.

For example, based on the selected biomarker sensing systems data, adrenal gland-related biomarkers, complications, and/or contextual information may be determined, including metastasis, blood vessel health, immunity level, and/or infection risk. Based on the selected biomarker sensing system data, adrenal gland-related conditions may be predicted, including edema. Metastasis may be determined based on analyzed adrenaline and/or nonadrenaline. Blood vessel health may be determined based on analyzed adrenaline and/or nonadrenaline. A blood vessel health score may be generated based on the determined blood vessel health. Immunity capability may be determined based on analyzed cortisol. Infection risk may be determined based on analyzed cortisol. Metastasis may be predicted based on analyzed cortisol. Circadian rhythm may be determined based on measured cortisol. High cortisol may lower immunity, increase infection risk, and/or lead to metastasis. High cortisol may affect circadian rhythm. Edema may be predicted based on analyzed aldosterone. Aldosterone may promote fluid retention. Fluid retention may relate to blood pressure and/or edema.

For example, based on the selected biomarker sensing systems data, pancreas-related biomarkers, complications, and/or contextual information may be determined, including blood sugar, hormones, polypeptides, and/or blood glucose control. Based on the selected biomarker sensing systems data, pancreas-related conditions may be predicted. The pancreas-related biomarkers may provide contextual information for various surgical outcomes. Blood sugar biomarkers may include insulin. Hormone biomarkers may include somatostatin. Polypeptide biomarkers may include pancreatic polypeptide. Blood glucose control may be determined based on insulin, somatostatin, and/or pancreatic polypeptide. Blood glucose control may provide contextual information for various surgical outcomes.

For example, based on the selected biomarker sensing systems data, testes-related biomarkers, complications, and/or contextual information may be determined, including reproductive development, sexual arousal, and/or immune system regulation. Based on the selected biomarker sensing systems data, testes-related conditions may be predicted. Testes-related biomarkers may include testosterone. Testosterone may provide contextual information for biomarkers, complications, and/or conditions, including those relating to the reproductive system. High levels of testosterone may suppress immunity.

For example, based on the selected biomarker sensing systems data, stomach/testes-related biomarkers, complications, and/or contextual information may be determined, including glucose handling, satiety, insulin secretion, digestion speed, and/or sleeve gastrectomy outcomes. Glucose handling and satiety biomarkers may include glucagon-like peptide-1 (GLP-1), cholecystokinin (CCK), and/or peptide YY. Appetite and/or insulin secretion may be determined based on analyzed GLP-1. Increased GLP-1 may be determined based on enhanced appetite and insulin secretion. Sleeve gastrectomy outcomes may be determined based on analyzed GLP-1. Satiety and/or sleeve gastrectomy outcomes may be determined based on analyzed CCK. Enhanced CCK levels may be predicted based on previous sleeve gastrectomy. Appetite and digestion speeds may be determined based on analyzed peptide YY. Increased peptide YY may reduce appetite and/or increase digestion speeds.

For example, based on the selected biomarker sensing systems data, hormone-related biomarkers, complications, and/or contextual information may be determined, including estrogen, progesterone, collagen product, fluid retention, and/or menstrual phase. Collagen production may be determined based on estrogen. Fluid retention may be determined based on estrogen. Surgical tool parameter adjustments may be generated based on determined collagen production and/or fluid retention.

For example, based on the selected biomarker sensing systems data, thyroid gland and parathyroid-related biomarkers, complications, and/or contextual information may be determined, including calcium handling, phosphate handling, metabolism, blood pressure, and/or surgical complications. Metabolism biomarkers may include triiodothyronine (T3) and/or thyroxine (T4). Blood pressure may be determined based on analyzed T3 and T4. High blood pressure may be determined based on increased T3 and/or increased T4. Surgical complications may be determined based on analyzed T3 and/or T4.

For example, based on the selected biomarker sensing systems data, stomach-related biomarkers, complications, and/or contextual information may be determined, including appetite. Stomach-related biomarkers may include ghrelin. Ghrelin may induce appetite.

The detection, prediction, determination, and/or generation described herein may be performed by a computing system described herein, such as a surgical hub, a computing system, and/or a smart device based on measured data and/or related biomarkers generated by the biomarker sensing systems.

Immune system-related biomarkers may relate to antigens and irritants, antimicrobial enzymes, the complement system, chemokines and cytokines, the lymphatic system, bone marrow, pathogens, damage-associated molecular patterns (DAMPs), and/or cells. Immune system-related biomarkers, complications, and/or contextual information may be determined based on analyzed biomarker sensing systems data. A computing system, as described herein, may select one or more biomarkers (e.g., data from biomarker sensing systems) from immune system-related biomarkers, including alcohol consumption, pH, respiratory rate, edema, sweat, and/or environment for analysis. Antigens/irritants For example, based on the selected biomarker sensing systems data, antigen and irritant-related biomarkers, complications, and/or contextual information may be determined, including healing ability, immune function, and/or cardiac issues. Based on the selected biomarker sensing systems data, antigen and irritant-related conditions may be predicted, including inflammation. Antigen and irritant-related biomarkers may include inhaled chemicals, inhaled irritants, ingested chemicals, and/or ingested irritants. Inhaled chemicals or irritants may be determined based on analyzed environmental data, including airborne chemicals, mycotoxins, and/or arsenic. Airborne chemicals may include cigarette smoke, asbestos, crystalline silica, alloy particles, and/or carbon nanotubes. Lung inflammation may be predicted based on analyzed airborne chemicals. Surgical tool parameter adjustments may be generated based on determined lung inflammation. Airway inflammation may be predicted based on analyzed mycotoxin and/or arsenic. Surgical tool parameter adjustments may be generated based on determined airway inflammation. Arsenic exposure may be determined based on urine, saliva, and/or ambient air sample analyses.

For example, based on the selected biomarker sensing systems data, antimicrobial enzyme-related biomarkers, complications, and/or contextual information may be determined, including colon state. Based on the selected biomarker sensing systems data, antimicrobial enzyme-related conditions may be predicted, including GI inflammation, acute kidney injury, *E. faecalis* infection, and/or *S. aureus* infection. Antimicrobial enzyme biomarkers may include lysozyme, lipocalin-2 (NGAL), and/or orosomuccoid. GI inflammation may be predicted based on analyzed lysozyme. Increased levels in lysozyme may be determined and/or predicted based on GI inflammation. Colon state may be determined based on analyzed lysozyme. Surgical tool parameter adjustments may be generated based on analyzed lysozyme levels. Acute kidney injury may be predicted based on analyzed NGAL. NGAL may be detected from serum and/or urine.

For example, based on the selected biomarker sensing systems data, complement system-related biomarkers, complications, and/or contextual information may be determined, including bacterial infection susceptibility. Bacterial infection susceptibility may be determined based on analyzed complement system deficiencies.

For example, based on the selected biomarker sensing systems data, chemokine and cytokine-related biomarkers, complications, and/or contextual information may be determined, including infection burden, inflammation burden, vascular permeability regulation, omentin, colonic tissue properties, and/or post-operation recovery. Based on the selected biomarker sensing systems data, chemokine and cytokine-related conditions may be predicted, including inflammatory bowel diseases, post-operation infection, lung fibrosis, lung scarring, pulmonary fibrosis, gastroesophageal reflux disease, cardiovascular disease, edema, and/or hyperplasia. Infection and/or inflammation burden biomarkers may include oral, salivary, exhaled, and/or C-reactive protein (CRP) data. Salivary cytokines may include interleukin-1 beta (IL-1$\beta$), interleukin-6 (IL-6), tumor necrosis factor alpha (TNF-$\alpha$) and/or interleukin-8 (IL-8).

In an example, inflammatory bowel diseases may be predicted based on analyzed salivary cytokines. Increased salivary cytokines may be determined based on inflammatory bowel diseases. Colonic tissue properties may be determined based on predicted inflammatory bowel diseases. Colonic tissue properties may include scarring, edema, and/or ulcering. Post-operation recovery and/or infection may be determined based on predicted inflammatory bowel diseases. Tumor size and/or lung scarring may be determined based on analyzed exhaled biomarkers. Lung fibrosis, pulmonary fibrosis, and/or gastroesophageal reflux disease may be predicted based on analyzed exhaled biomarkers. Exhaled biomarkers may include exhaled cytokines, pH, hydrogen peroxide (H2O2), and/or nitric oxide. Exhaled cytokines may include IL-6, TNF-α, and/or interleukin-17 (IL-17). Lung fibrosis may be predicted based on measured pH and/or H2O2 from exhaled breath. Fibrosis may be predicted based on increased H2O2 concentration. Increased lung tissue scarring may be predicted based on fibrosis. Surgical tool parameter adjustments may be generated based on predicted lung fibrosis. In an example, pulmonary fibrosis and/or gastroesophageal reflux disease may be predicted based on analyzed exhaled nitric oxide. Pulmonary fibrosis may be predicted based on determined increased nitrates and/or nitrites. Gastroesophageal disease may be predicted based on determined reduced nitrates and/or nitrites. Surgical tool parameter adjustments may be generated based on predicted pulmonary fibrosis and/or gastroesophageal reflux disease. Cardiovascular disease, inflammatory bowel diseases, and/or infection may be predicted based on analyzed CRP biomarkers. Risk of serious cardiovascular disease may increase with high CRP concentration. Inflammatory bowel disease may be predicted based on elevated CRP concentration. Infection may be predicted based on elevated CRP concentration. In an example, edema may be predicted based on analyzed vascular permeability regulation biomarkers. Increased vascular permeability during inflammation may be determined based on analyzed bradykinin and/or histamine. Edema may be predicted based on increased vascular permeability during inflammation. Vascular permeability may be determined based on endothelial adhesion molecules. Endothelial adhesion molecules may be determined based on cell samples. Endothelial adhesion molecules may affect vascular permeability, immune cell recruitment, and/or fluid build-up in edema. Surgical tool parameter adjustments may be generated based on analyzed vascular permeability regulation biomarkers. In an example, hyperplasia may be predicted based on analyzed omentin. Hyperplasia may alter tissue properties. Surgical tool parameter adjustments may be generated based on predicted hyperplasia.

For example, based on the selected biomarker sensing systems data, lymphatic system-related biomarkers, complications, and/or contextual information may be determined, including lymph nodes, lymph composition, lymph location, and/or lymph swelling. Based on the selected biomarker sensing systems data, lymphatic system-related conditions may be predicted, including post-operation inflammation, post-operation infection, and/or fibrosis. Post-operation inflammation and/or infection may be predicted based on determined lymph node swelling. Surgical tool parameter adjustments may be generated based on the analyzed lymph node swelling. Surgical tool parameter adjustments, including harmonic tool parameter adjustments, may be generated based on the determined collagen deposition. Collagen deposition may increase with lymph node fibrosis. Inflammatory conditions may be predicted based on lymph composition. Metastatic cell spread may be determined based on lymph composition. Surgical tool parameter adjustments may be generated based on lymph peptidome. Lymph peptidome may change based on inflammatory conditions.

For example, based on the selected biomarker sensing systems data, pathogen-related biomarkers, complications, and/or contextual information may be determined, including pathogen-associated molecular patterns (PAMPs), pathogen burden, H. Pylori, and/or stomach tissue properties. Based on the selected biomarker sensing systems data, pathogen-related conditions may be predicted, including infection, stomach inflammation, and/or ulcering. PAMPs biomarkers may include pathogen antigens. Pathogen antigens may impact pathogen burden. Stomach inflammation and/or potential ulcering may be predicted based on predicted infection. Stomach tissue property alterations may be determined based on predicted infection.

For example, based on the selected biomarker sensing systems data, DAMPs-related biomarkers, complications, and/or contextual information may be determined, including stress (e.g., cardiovascular, metabolic, glycemic, and/or cellular) and/or necrosis. Based on the selected biomarker sensing systems data, DAMPs-related conditions may be predicted, including acute myocardial infarction, intestinal inflammation, and/or infection. Cellular stress biomarkers may include creatine kinase MB, pyruvate kinase isoenzyme type M2 (M2-PK), irisin, and/or microRNA. In an example, acute myocardial infarction may be predicted based on analyzed creatine kinase MB biomarkers. Intestinal inflammation may be predicted based on analyzed M2-PK biomarkers. Stress may be determined based on analyzed irisin biomarkers. Inflammatory diseases and/or infection may be predicted based on analyzed microRNA biomarkers. Surgical tool parameter adjustments may be generated based on predicted inflammation and/or infection. Inflammation and/or infection may be predicted based on analyzed necrosis biomarkers. Necrosis biomarkers may include reactive oxygen species (ROS). Inflammation and/or infection may be predicted based on increased ROS. Post-operation recovery may be determined based on analyzed ROS.

For example, based on the selected biomarker sensing systems, cell-related biomarkers, complications, and/or contextual information may be determined, including granulocytes, natural killer cells (NK cells), macrophages, lymphocytes, and/or colonic tissue properties. Based on the selected biomarker sensing systems, cell-related conditions may be predicted, including post-operation infection, ulceratic colitis, inflammation, and/or inflammatory bowel disease. Granulocyte biomarkers may include eosinophilia and/or neutrophils. Eosinophilia biomarkers may include sputum cell count, eosinophilic cationic protein, and/or fractional exhaled nitric oxide. Neutrophil biomarkers may include S100 proteins, myeloperoxidase, and/or human neutrophil lipocalin. Lymphocyte biomarkers may include antibodies, adaptive response, and/or immune memory. The antibodies may include immunoglobulin A (IgA) and/or immunoglobulin M (IgM). In an example, post-operational infection and/or pre-operation inflammation may be predicted based on analyzed sputum cell count. Ulcerative colitis may be predicted based on analyzed eosinophilic cationic protein. Altered colonic tissue properties may be determined based on the predicted ulcerative colitis. Eosinophils may produce eosinophilic cationic protein which may be determined based on ulcerative colitis. Inflammation may be predicted based on analyzed fractional exhaled nitric oxide. The inflammation may include type 1 asthma-like inflammation. Surgical tool parameter adjustments may be generated based on the predicted inflammation. In an example, inflammatory bowel diseases may be predicted based on S100 proteins. The S100 proteins may include calprotectin. Colonic tissue properties may be determined based on the predicted inflammatory bowel diseases. Ulcerative colitis may be predicted based on analyzed myeloperoxidase and/or human neutrophil lipocalin. Altered colonic tissue properties may be determined based on predicted ulcerative colitis. In an example, inflammation may be predicted based on antibody biomarkers. Bowel inflammation may be predicted based on IgA. Cardiovascular inflammation may be predicted based on IgM.

The detection, prediction, determination, and/or generation described herein may be performed by a computing system described herein, such as a surgical hub, a computing device, and/or a smart device based on measured data and/or related biomarkers generated by the biomarker sensing systems.

Tumors may include benign and/or malignant tumors. Tumor-related biomarkers, complications, contextual information, and/or conditions may be determined and/or predicted based on analyzed biomarker sensing systems data. A computing system, as described herein, may select one or more biomarkers (e.g., data from biomarker sensing systems) from tumor-related biomarkers, including circulating tumor cells for analysis.

For example, based on the selected biomarker sensing systems data, benign tumor-related biomarkers, conditions, and/or contextual information may be determined, including benign tumor replication, benign tumor metabolism, and/or benign tumor synthesis. Benign tumor replication may include rate of mitotic activity, mitotic metabolism, and/or synthesis biomarkers. Benign tumor metabolism may include metabolic demand and/or metabolic product biomarkers. Benign tumor synthesis may include protein expression and/or gene expression biomarkers.

For example, based on the selected biomarker sensing systems data, malignant tumor-related biomarkers, complications, and/or contextual information may be determined, including malignant tumor synthesis, malignant tumor metabolism, malignant tumor replication, microsatellite stability, metastatic risk, metastatic tumors, tumor growth, tumor recession, and/or metastatic activity. Based on the selected biomarker sensing systems data, malignant tumor-related conditions may be predicted, including cancer. Malignant tumor synthesis may include gene expression and/or protein expression biomarkers. Gene expression may be determined based on tumor biopsy and/or genome analysis. Protein expression biomarkers may include cancer antigen 125 (CA-125) and/or carcinoembryonic antigen (CEA). CEA may be measured based on urine and/or saliva. Malignant tumor replication data may include rate of mitotic activity, mitotic encapsulation, tumor mass, and/or microRNA 200c.

In an example, microsatellite stability may be determined based on analyzed gene expression. Metastatic risk may be determined based on determined microsatellite stability. Higher metastatic risk may be determined and/or predicted based on low microsatellite instability. In an example, metastatic tumors, tumor growth, tumor metastasis, and/or tumor recession may be determined based on analyzed protein expression. Metastatic tumors may be determined and/or predicted based on elevated CA-125. Cancer may be predicted based on CA-125. Cancer may be predicted based on certain levels of CEA. Tumor growth, metastasis, and/or recession may be monitored based on detected changes in CEA. Metastatic activity may be determined based on malignant tumor replication. Cancer may be predicted based on malignant tumor replication. MicroRNA 200c may be released into blood by certain cancers. Metastatic activity may be determined and/or predicted based on presence of circulating tumor cells.

The detection, prediction, determination, and/or generation described herein may be performed by a computing system described herein, such as a surgical hub, a computing device, and/or a smart device based on measured data and/or related biomarkers generated by the biomarker sensing systems.

The musculoskeletal system may include muscles, bones, marrow, and/or cartilage. The muscles may include smooth muscle, cardiac muscle, and/or skeletal muscle. The smooth muscle may include calmodulin, connective tissue, structural features, hyperplasia, actin, and/or myosin. The bones may include calcified bone, osteoblasts, and/or osteoclasts. The marrow may include red marrow and/or yellow marrow. The cartilage may include cartilaginous tissue and/or chondrocytes. Musculoskeletal system-related biomarkers, complications, contextual information, and/or conditions may be determined and/or predicted based on analyzed biomarker sensing systems data. A computing system, as described herein, may select one or more biomarkers (e.g., data from biomarker sensing systems) from musculoskeletal-related biomarkers for analysis.

For example, based on the selected biomarker sensing systems data, muscle-related biomarkers, complications, and/or contextual information may be determined, including serum calmodulin levels, mechanical strength, muscle body, hyperplasia, muscle contraction ability, and/or muscle damage. Based on the selected biomarker sensing systems data, muscle-related conditions may be predicted. In an example, neurological conditions may be predicted based on analyzed serum calmodulin levels. Mechanical strength may be determined based on analyzed smooth muscle collagen levels. Collagen may affect mechanical strength as collagen may bind smooth muscle filament together. Muscle body may be determined based on analyzed structural features. The muscle body may include an intermediate body and/or a dense body. Hyperplasia may be determined based on analyzed omentin levels. Omentin may indicate hyperplasia. Hyperplasia may be determined and/or predicted based on thick areas of smooth muscles. Muscle contraction ability may be determined based on analyzed smooth muscle alpha-actin expression. Muscle contraction inability may result from an abnormal expression of actin in smooth muscle. In an example, muscle damage may be determined based on analyzed circulating smooth muscle myosin and/or skeletal muscle myosin. Muscle strength may be determined based on analyzed circulating smooth muscle myosin. Muscle damage and/or weak, friable smooth muscle may be determined and/or predicted based on circulating smooth muscle myosin and/or skeletal muscle myosin. Smooth muscle myosin may be measured from urine. In an example, muscle damage may be determined based on cardiac and/or skeletal muscle biomarkers. Cardiac and/or skeletal muscle biomarkers may include circulating troponin. Muscle damage may be determined and/or predicted based on circulating troponin alongside myosin.

For example, based on the selected biomarker sensing systems data, bone-related biomarkers, complications, and/or contextual information may be determined, including calcified bone properties, calcified bone functions, osteoblasts number, osteoid secretion, osteoclasts number, and/or secreted osteoclasts.

For example, based on the selected biomarker sensing systems data, marrow-related biomarkers, complications, and/or contextual information may be determined, including tissue breakdown and/or collagen secretion. Arthritic breakdown of cartilaginous tissue may be determined based on analyzed cartilaginous tissue biomarkers. Collage secretion by muscle cells may be determined based on analyzed chondrocyte biomarkers.

The detection, prediction, determination, and/or generation described herein may be performed by a computing system described herein, such as a surgical hub, a computing device, and/or a smart device based on measured data and/or related biomarkers generated by the biomarker sensing systems.

Reproductive system-related biomarkers, complications, contextual information, and/or conditions may be determined and/or predicted based on analyzed biomarker sensing systems data. A computing system, as described herein, may select one or more biomarkers (e.g., data from biomarker sensing systems) from reproductive system-related biomarkers for analysis. Reproductive system-related biomarkers, complications, and/or contextual information may be determined based on analyzed biomarker sensing systems data, including female anatomy, female function, menstrual cycle, pH, bleeding, wound healing, and/or scarring. Female anatomy biomarkers may include the ovaries, vagina, cervix, fallopian tubes, and/or uterus. Female function biomarkers may include reproductive hormones, pregnancy, menopause, and/or menstrual cycle. Reproductive system-related conditions may be predicted based on analyzed biomarker sensing systems data, including endometriosis, adhesions, vaginosis, bacterial infection, SSI, and/or pelvic abscesses.

In an example, endometriosis may be predicted based on female anatomy biomarkers. Adhesions may be predicted based on female anatomy biomarkers. The adhesions may include sigmoid colon adhesions. Endometriosis may be predicted based on menstrual blood. Menstrual blood may include molecular signals from endometriosis. Sigmoid colon adhesions may be predicted based on predicted endometriosis. In an example, menstrual phase and/or menstrual cycle length may be determined based on the menstrual cycle. Bleeding, wound healing, and/or scarring may be determined based on the analyzed menstrual phase. Risk of endometriosis may be predicted based on the analyzed menstrual cycle. Higher risk of endometriosis may be predicted based on shorter menstrual cycle lengths. Molecular signals may be determined based on analyzed menstrual blood and/or discharge pH. Endometriosis may be predicted based on the determined molecular signals. Vaginal pH may be determined based on analyzed discharge pH. Vaginosis and/or bacterial infections may be predicted based on the analyzed vaginal pH. Vaginosis and/or bacterial infections may be predicted based on changes in vaginal pH. Risk of SSI and/or pelvic abscesses during gynecologic procedures may be predicted based on predicted vaginosis.

The detection, prediction, determination, and/or generation described herein may be performed by any of the computing systems within any of the computer-implemented patient and surgeon monitoring systems described herein, such as a surgical hub, a computing device, and/or a smart device based on measured data and/or related biomarkers generated by the one or more sensing systems.

Figure 2A:
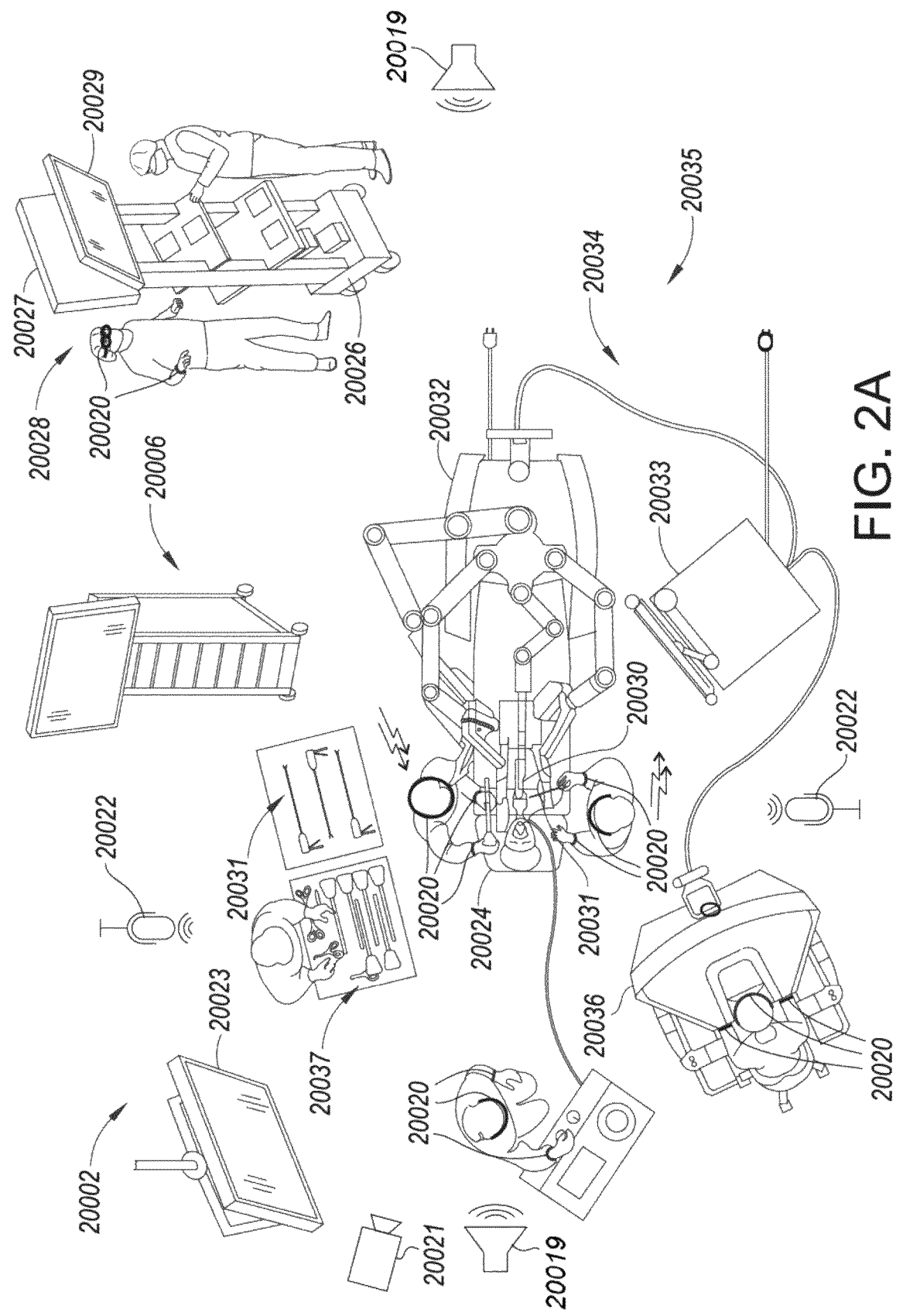
FIG. 2A shows an example of a surgeon monitoring system in a surgical operating room.

FIG. 2A shows an example of a surgeon monitoring system 20002 in a surgical operating room. As illustrated in FIG. 2A, a patient is being operated on by one or more health care professionals (HCPs). The HCPs are being monitored by one or more surgeon sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The surgeon sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2A, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2A, a surgical instrument 20031 is being used in the surgical procedure as part of the surgeon monitoring system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2A illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, surgeon sensing systems 20020 as shown in FIG. 2A. The surgeon sensing systems 20020 may include sensing systems to monitor and detect a set of physical states and/or a set of physiological states of a healthcare provider (HCP). An HCP may be a surgeon or one or more healthcare personnel assisting the surgeon or other healthcare service providers in general. In an example, a sensing system 20020 may measure a set of biomarkers to monitor the heart rate of an HCP. In another example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the surgeon sensing systems 20020 may measure one or more surgeon biomarkers associated with an HCP and send the measurement data associated with the surgeon biomarkers to the surgical hub 20006. The surgeon sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 2B:
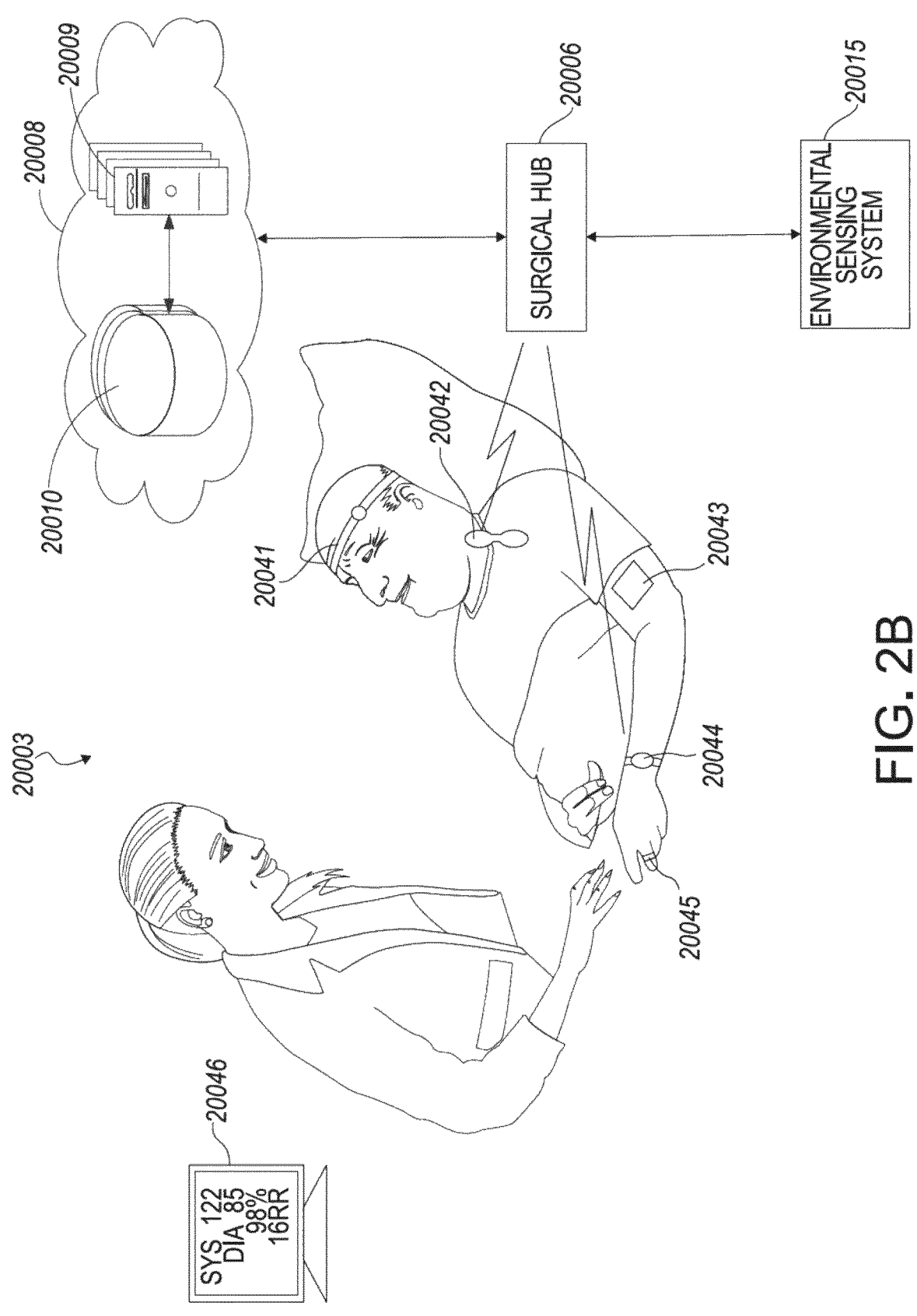
FIG. 2B shows an example of a patient monitoring system (e.g., a controlled patient monitoring system).

FIG. 2B shows an example of a patient monitoring system 20003 (e.g., a controlled patient monitoring system). As illustrated in FIG. 2B, a patient in a controlled environment (e.g., in a hospital recovery room) may be monitored by a plurality of sensing systems (e.g., patient sensing systems 20041). A patient sensing system 20041 (e.g., a head band) may be used to measure an electroencephalogram (EEG) to measure electrical activity of the brain of a patient. A patient sensing system 20042 may be used to measure various biomarkers of the patient including, for example, heart rate, VO2 level, etc. A patient sensing system 20043 (e.g., flexible patch attached to the patient's skin) may be used to measure sweat lactate and/or potassium levels by analyzing small amounts of sweat that is captured from the surface of the skin using microfluidic channels. A patient sensing system 20044 (e.g., a wristband or a watch) may be used to measure blood pressure, heart rate, heart rate variability, VO2 levels, etc. using various techniques, as described herein. A patient sensing system 20045 (e.g., a ring on finger) may be used to measure peripheral temperature, heart rate, heart rate variability, VO2 levels, etc. using various techniques, as described herein. The patient sensing systems 20041-20045 may use a radio frequency (RF) link to be in communication with the surgical hub 20006. The patient sensing systems 20041-20045 may use one or more of the following RF protocols for communication with the surgical hub 20006: Bluetooth, Bluetooth Low-Energy (BLE), Bluetooth Smart, Zigbee, Z-wave, IPv6 Low-power wireless Personal Area Network (6LoWPAN), Thread, Wi-Fi, etc.

The sensing systems 20041-20045 may be in communication with a surgical hub 20006, which in turn may be in communication with a remote server 20009 of the remote cloud computing system 20008. The surgical hub 20006 is also in communication with an HID 20046. The HID 20046 may display measured data associated with one or more patient biomarkers. For example, the HID 20046 may display blood pressure, Oxygen saturation level, respiratory rate, etc. The HID 20046 may display notifications for the patient or an HCP providing information about the patient, for example, information about a recovery milestone or a complication. In an example, the information about a recovery milestone or a complication may be associated with a surgical procedure the patient may have undergone. In an example, the HID 20046 may display instructions for the patient to perform an activity. For example, the HID 20046 may display inhaling and exhaling instructions. In an example the HID 20046 may be part of a sensing system.

As illustrated in FIG. 2B, the patient and the environment surrounding the patient may be monitored by one or more environmental sensing systems 20015 including, for example, a microphone (e.g., for detecting ambient noise associated with or around a patient), a temperature/humidity sensor, a camera for detecting breathing patterns of the patient, etc. The environmental sensing systems 20015 may be in communication with the surgical hub 20006, which in turn is in communication with a remote server 20009 of the remote cloud computing system 20008.

In an example, a patient sensing system 20044 may receive a notification information from the surgical hub 20006 for displaying on a display unit or an HID of the patient sensing system 20044. The notification information may include a notification about a recovery milestone or a notification about a complication, for example, in case of post-surgical recovery. In an example, the notification information may include an actionable severity level associated with the notification. The patient sensing system 20044 may display the notification and the actionable severity level to the patient. The patient sensing system may alert the patient using a haptic feedback. The visual notification and/or the haptic notification may be accompanied by an audible notification prompting the patient to pay attention to the visual notification provided on the display unit of the sensing system.

Figure 2C:
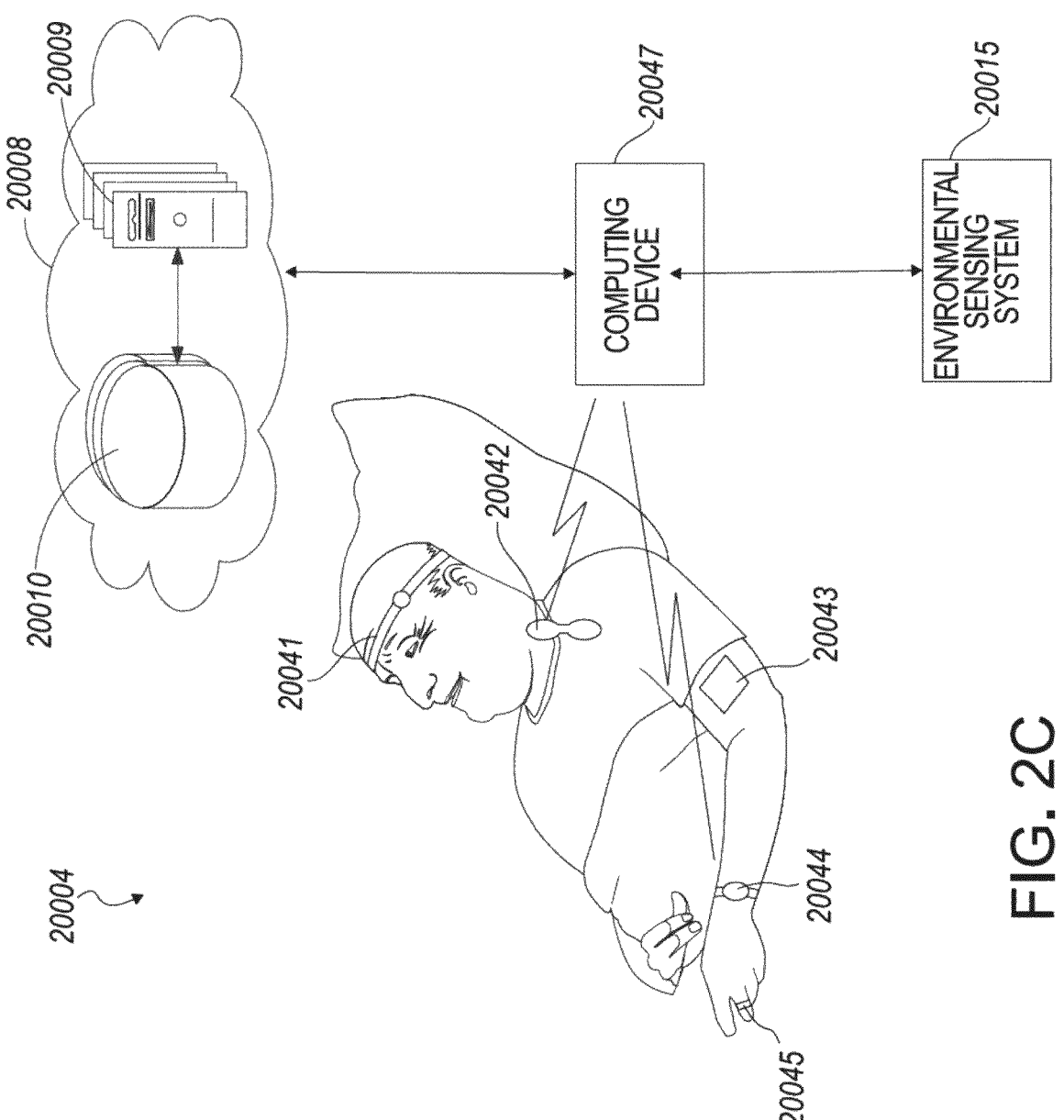
FIG. 2C shows an example of a patient monitoring system (e.g., an uncontrolled patient monitoring system).

FIG. 2C shows an example of a patient monitoring system (e.g., an uncontrolled patient monitoring system 20004). As illustrated in FIG. 2C, a patient in an uncontrolled environment (e.g., a patient's residence) is being monitored by a plurality of patient sensing systems 20041-20045. The patient sensing systems 20041-20045 may measure and/or monitor measurement data associated with one or more patient biomarkers. For example, a patient sensing system 20041, a head band, may be used to measure an electroencephalogram (EEG). Other patient sensing systems 20042, 20043, 20044, and 20045 are examples where various patient biomarkers are monitored, measured, and/or reported, as described in FIG. 2B. One or more of the patient sensing systems 20041-20045 may be send the measured data associated with the patient biomarkers being monitored to the computing device 20047, which in turn may be in communication with a remote server 20009 of the remote cloud computing system 20008. The patient sensing systems 20041-20045 may use a radio frequency (RF) link to be in communication with a computing device 20047 (e.g., a smart phone, a tablet, etc.). The patient sensing systems 20041-20045 may use one or more of the following RF protocols for communication with the computing device 20047: Bluetooth, Bluetooth Low-Energy (BLE), Bluetooth Smart, Zigbee, Z-wave, IPv6 Low-power wireless Personal Area Network (6LoWPAN), Thread, Wi-Fi, etc. In an example, the patient sensing systems 20041-20045 may be connected to the computing device 20047 via a wireless router, a wireless hub, or a wireless bridge.

The computing device 20047 may be in communication with a remote server 20009 that is part of a cloud computing system 20008. In an example, the computing device 20047 may be in communication with a remote server 20009 via an internet service provider's cable/FIOS networking node. In an example, a patient sensing system may be in direct communication with a remote server 20009. The computing device 20047 or the sensing system may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, a computing device 20047 may display information associated with a patient biomarker. For example, a computing device 20047 may display blood pressure, Oxygen saturation level, respiratory rate, etc. A computing device 20047 may display notifications for the patient or an HCP providing information about the patient, for example, information about a recovery milestone or a complication.

In an example, the computing device 20047 and/or the patient sensing system 20044 may receive a notification information from the surgical hub 20006 for displaying on a display unit of the computing device 20047 and/or the patient sensing system 20044. The notification information may include a notification about a recovery milestone or a notification about a complication, for example, in case of post-surgical recovery. The notification information may also include an actionable severity level associated with the notification. The computing device 20047 and/or the sensing system 20044 may display the notification and the actionable severity level to the patient. The patient sensing system may also alert the patient using a haptic feedback. The visual notification and/or the haptic notification may be accompanied by an audible notification prompting the patient to pay attention to the visual notification provided on the display unit of the sensing system.

Figure 3:
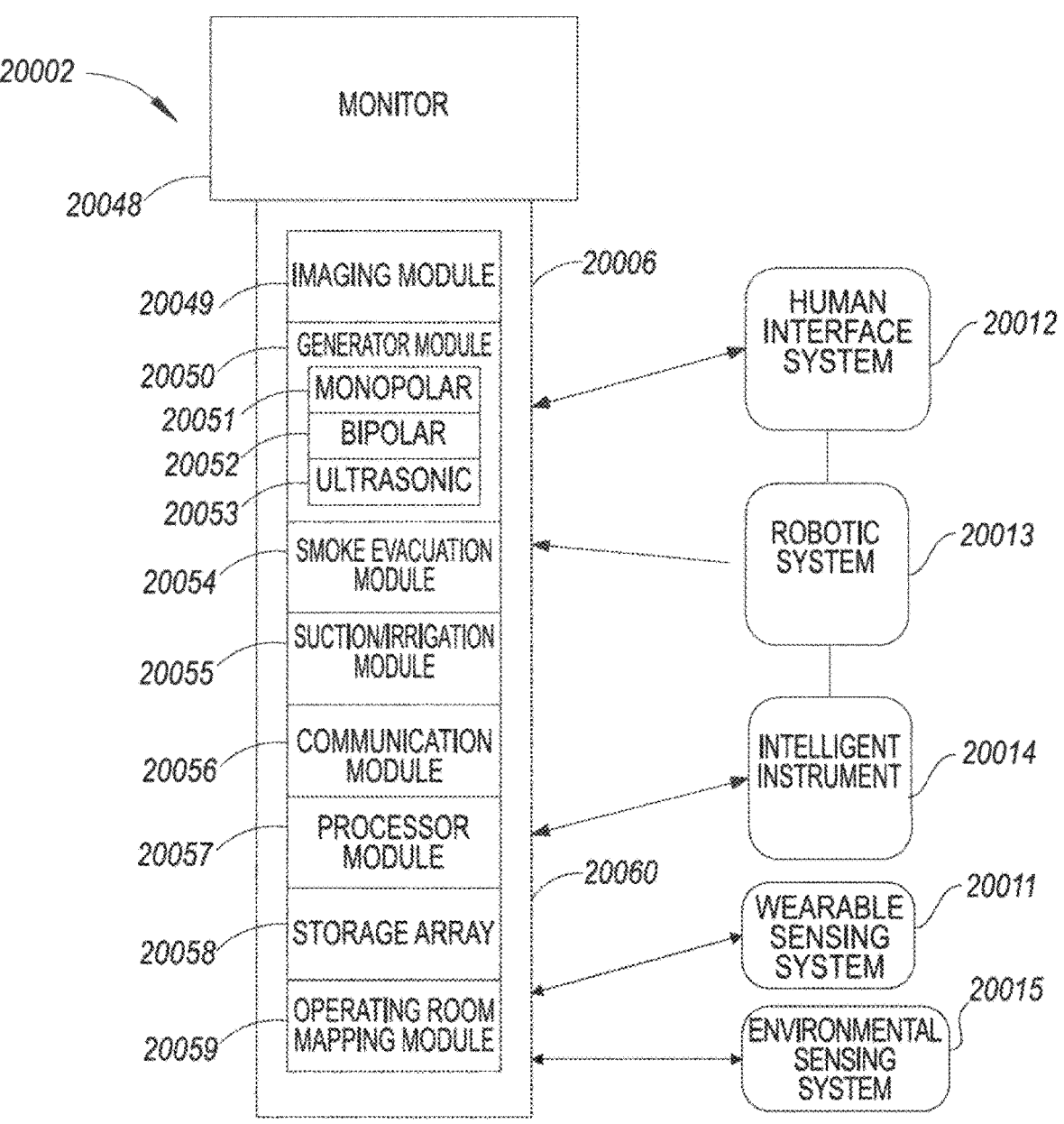
FIG. 3 illustrates an example surgical hub paired with various systems.

FIG. 3 shows an example surgeon monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and inter-active communication between the generators docked into the hub modular enclosure 20060 so that the generators would act as a single generator.

Figure 4:
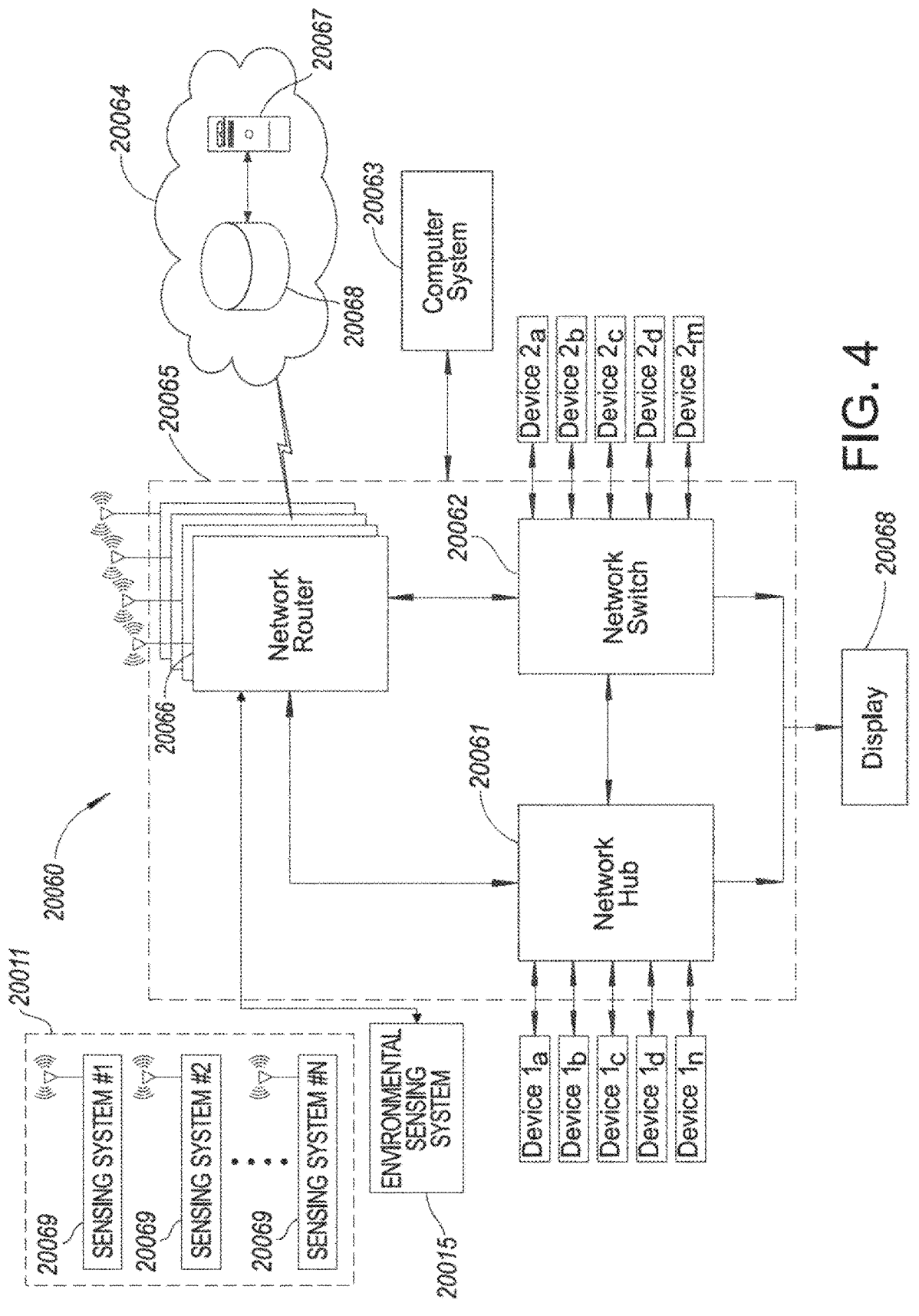
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, an environment sensing system, and a set of other modular devices located in one or more operating theaters of a healthcare facility, a patient recovery room, or a room in a healthcare facility specially equipped for surgical opera-tions, to the cloud, in accordance with at least one aspect of the present disclosure.

As illustrated in FIG. 4, a surgical hub system 20060 may include a modular communication hub 20065 that is con-figured to connect modular devices located in a healthcare facility to a cloud-based system (e.g., a cloud computing system 20064 that may include a remote server 20067 coupled to a remote storage 20068). The modular commu-nication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation. Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be trans-ferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include a surgeon sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the net-work router 20066 to connect to the sensing systems 20069 to the local computer system 20063 and/or the cloud com-puting system 20064. Data associated with the sensing systems 20069 may be transferred to the cloud computing system 20064 via the network router 20066 for data pro-cessing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with mul-tiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endo-scope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different ser-vices—such as servers, storage, and applications—are deliv-ered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
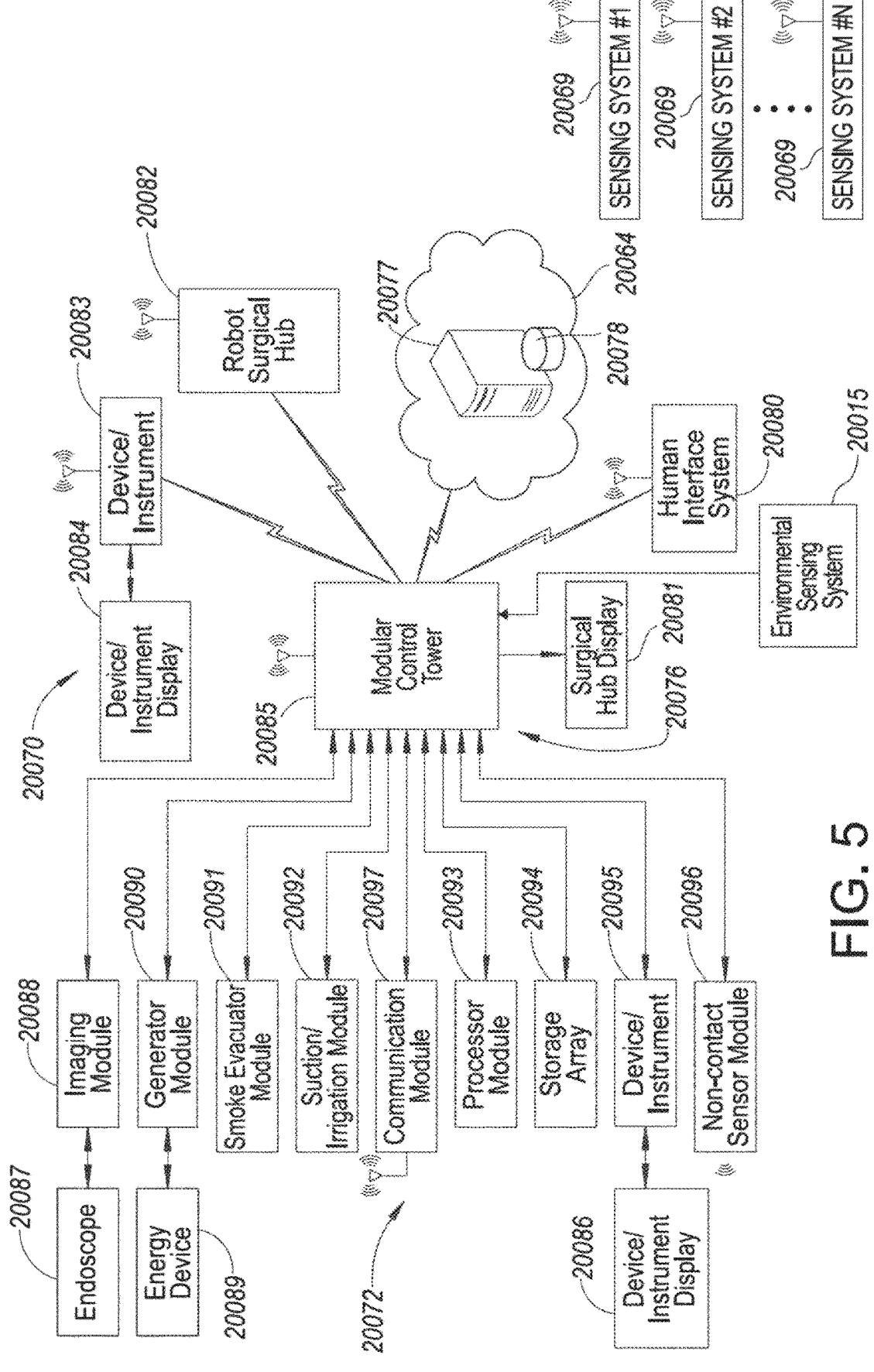
FIG. 5 illustrates an example computer-implemented interactive surgical system that may be part of a surgeon monitoring system.
Figure 6A:
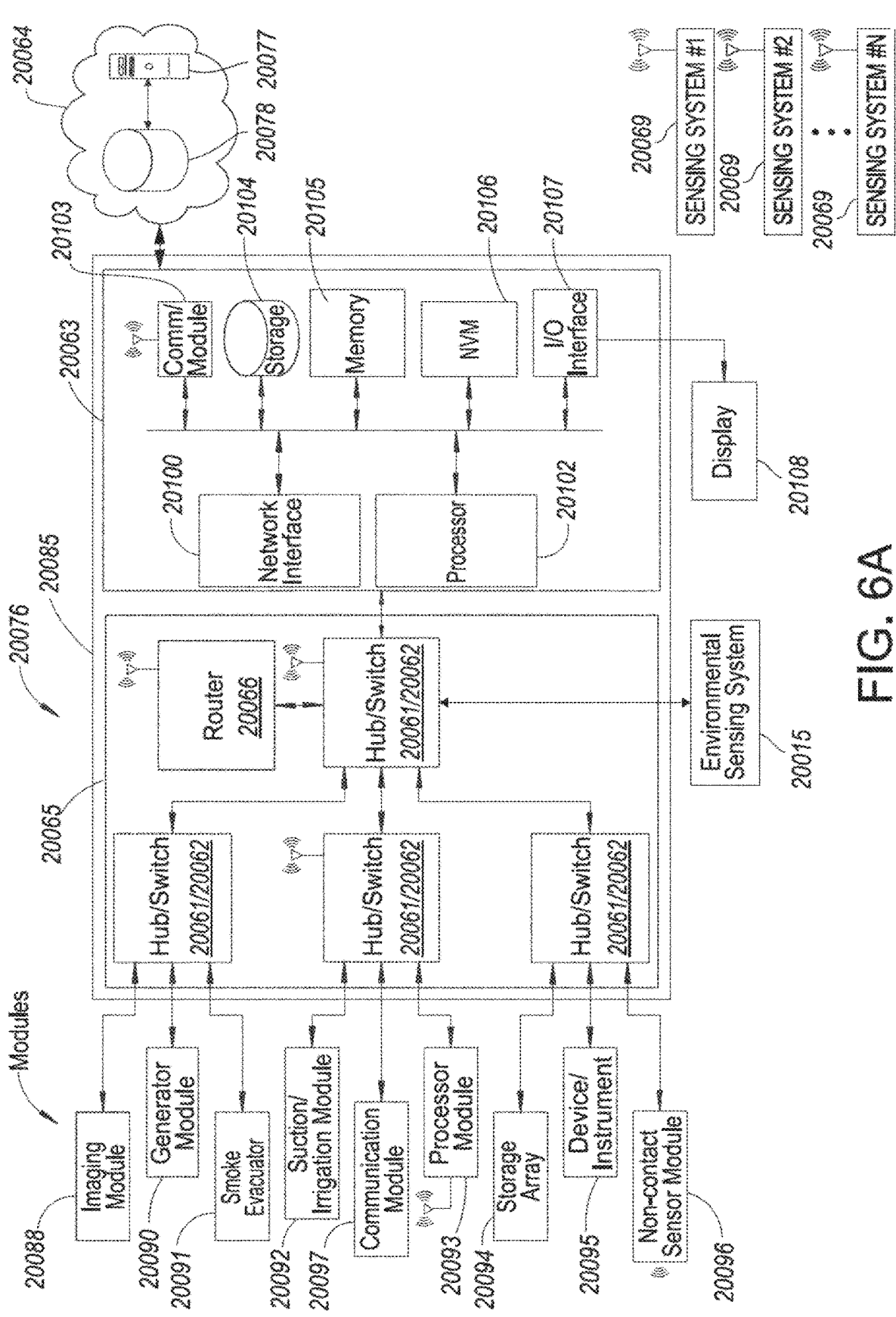
FIG. 6A illustrates a surgical hub comprising a plurality of modules coupled to a modular control tower.

FIG. 5 illustrates a computer-implemented interactive surgical system 20070 that may be a part of the surgeon monitoring system 20002. The computer-implemented interactive surgical system 20070 is similar in many respects to the surgeon sensing system 20002. For example, the computer-implemented interactive surgical system 20070 may include one or more surgical sub-systems 20072, which are similar in many respects to the surgeon monitoring systems 20002. Each sub-surgical system 20072 includes at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems (e.g., surgeon sensing systems 20002 and/or patient sensing system 20003), intelligent surgical instruments, robots, and other computerized devices located in the operating theater. As shown in FIG. 6A, the modular control tower 20085 may include a modular communication hub 20065 coupled to a local computing system 20063.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control tower 20085 in conjunction with images and overlaid images.

FIG. 6A illustrates a surgical hub 20076 comprising a plurality of modules coupled to the modular control tower 20085. As shown in FIG. 6A, the surgical hub 20076 may be connected to a generator module 20090, the smoke evacuator module 20091, suction/irrigation module 20092, and the communication module 20097. The modular control tower 20085 may comprise a modular communication hub 20065, e.g., a network connectivity device, and a computer system 20063 to provide local wireless connectivity with the sensing systems, local processing, complication monitoring, visualization, and imaging, for example. As shown in FIG. 6A, the modular communication hub 20065 may be connected in a configuration (e.g., a tiered configuration) to expand a number of modules (e.g., devices) and a number of sensing systems 20069 that may be connected to the modular communication hub 20065 and transfer data associated with the modules and/or measurement data associated with the sensing systems 20069 to the computer system 20063, cloud computing resources, or both. As shown in FIG. 6A, each of the network hubs/switches 20061/20062 in the modular communication hub 20065 may include three downstream ports and one upstream port. The upstream network hub/switch may be connected to a processor 20102 to provide a communication connection to the cloud computing resources and a local display 20108. At least one of the network/hub switches 20061/20062 in the modular communication hub 20065 may have at least one wireless interface to provided communication connection between the sensing systems 20069 and/or the devices 20095 and the cloud computing system 20064. Communication to the cloud computing system 20064 may be made either through a wired or a wireless communication channel.

The surgical hub 20076 may employ a non-contact sensor module 20096 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 20063 may comprise a processor 20102 and a network interface 20100. The processor 20102 may be coupled to a communication module 20103, storage 20104, memory 20105, non-volatile memory 20106, and input/output (I/O) interface 20107 via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 20102 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor 20102 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 20063 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface 20107. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

Figure 6B:
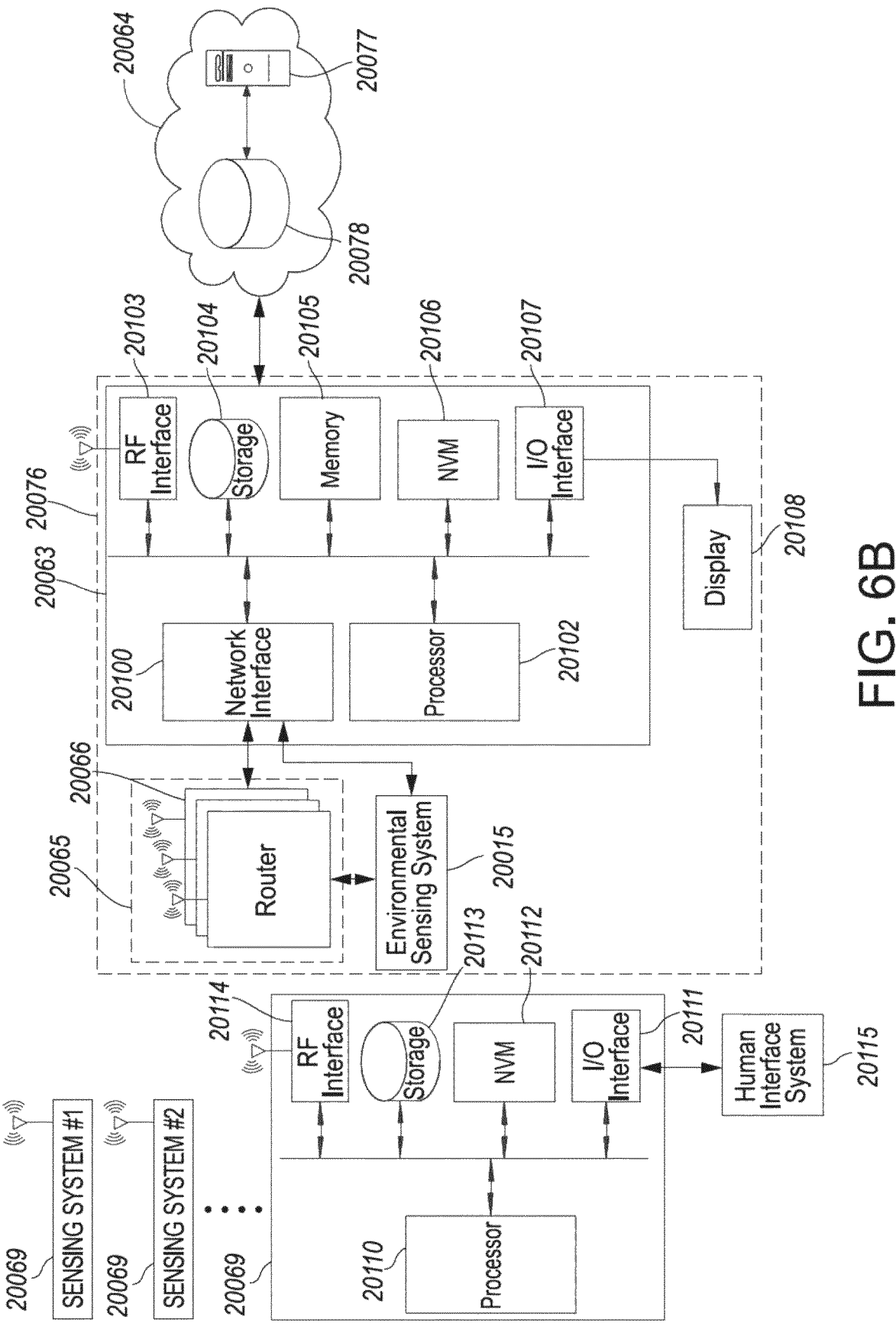
FIG. 6B illustrates an example of a controlled patient monitoring system.

In various examples, the computer system 20063 of FIG. 4, FIG. 6A and FIG. 6B, the imaging module 20088 and/or human interface system 20080, and/or the processor module 20093 of FIG. 5 and FIG. 6A may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

FIG. 6B illustrates an example of a wearable monitoring system, e.g., a controlled patient monitoring system. A controlled patient monitoring system may be the sensing system used to monitor a set of patient biomarkers when the patient is at a healthcare facility. The controlled patient monitoring system may be deployed for pre-surgical patient monitoring when a patient is being prepared for a surgical procedure, in-surgical monitoring when a patient is being operated on, or in post-surgical monitoring, for example, when a patient is recovering, etc. As illustrated in FIG. 6B, a controlled patient monitoring system may include a surgical hub system 20076, which may include one or more routers 20066 of the modular communication hub 20065 and a computer system 20063. The routers 20065 may include wireless routers, wired switches, wired routers, wired or wireless networking hubs, etc. In an example, the routers 20065 may be part of the infrastructure. The computing system 20063 may provide local processing for monitoring various biomarkers associated with a patient or a surgeon, and a notification mechanism to indicate to the patient and/or a healthcare provided (HCP) that a milestone (e.g., a recovery milestone) is met or a complication is detected. The computing system 20063 of the surgical hub system 20076 may also be used to generate a severity level associated with the notification, for example, a notification that a complication has been detected.

Figure 6C:
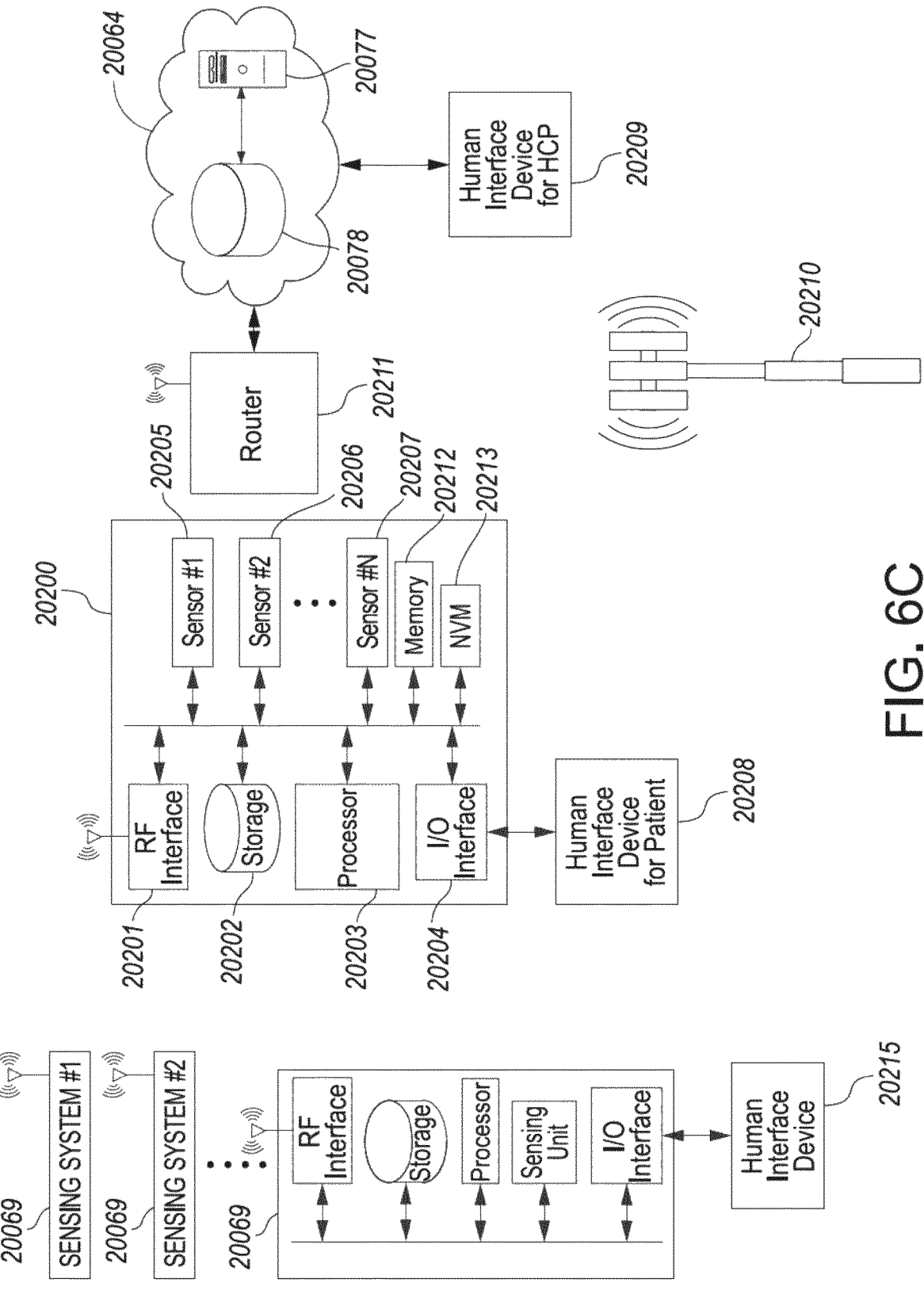
FIG. 6C illustrates an example of an uncontrolled patient monitoring system.
Figure 7A:
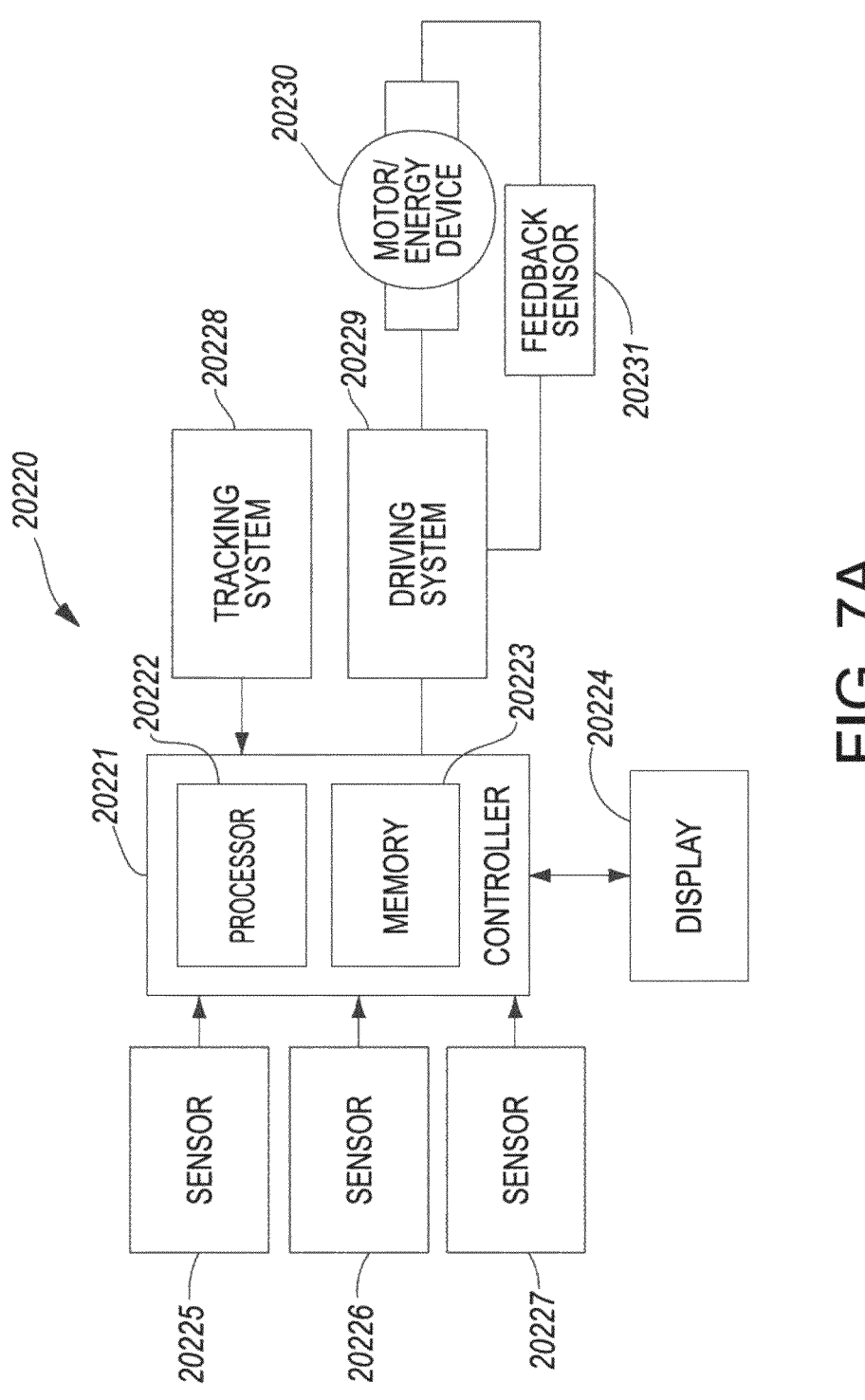
FIG. 7A illustrates a logic diagram of a control system of a surgical instrument or a tool.
Figure 7B:
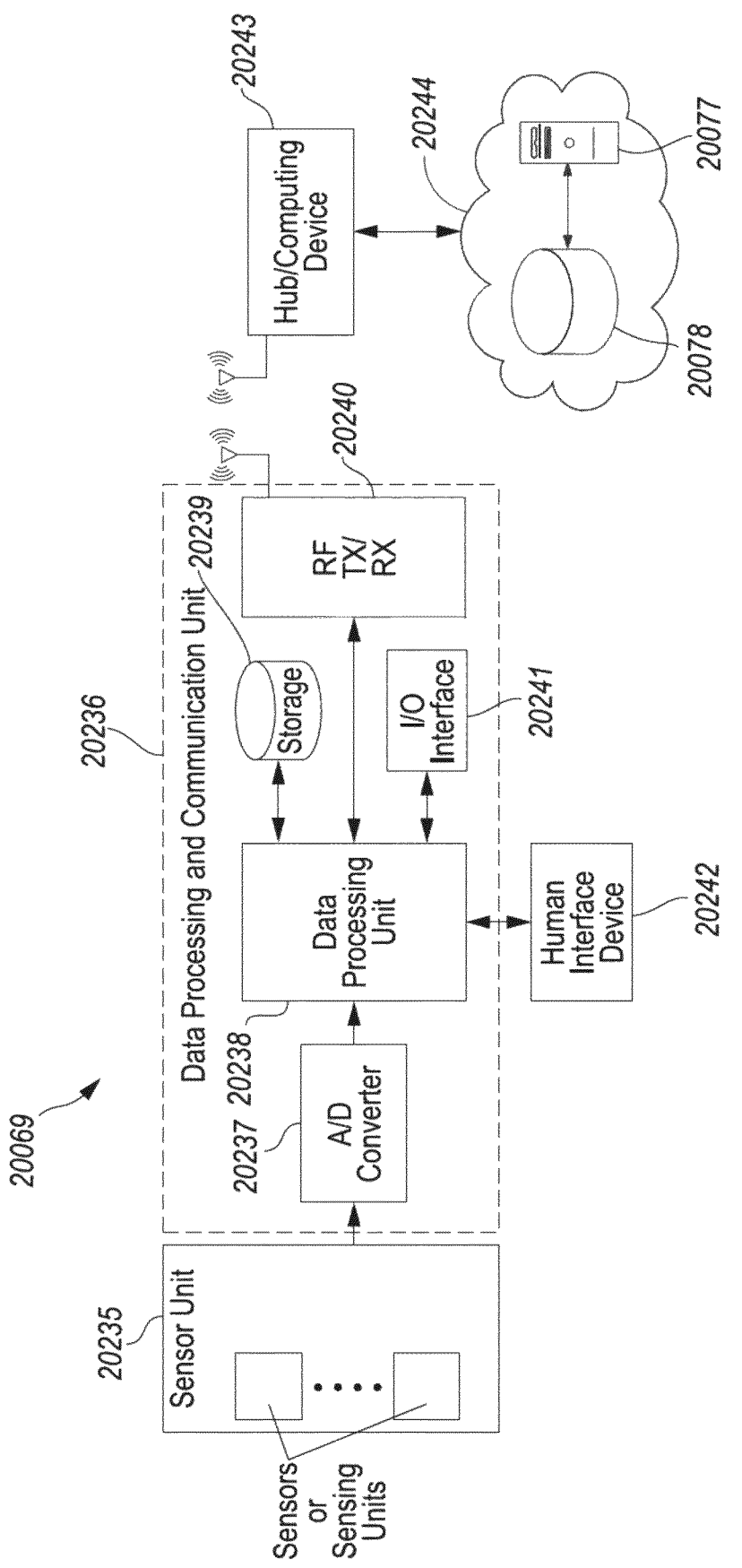
FIG. 7B shows an exemplary sensing system with a sensor unit and a data processing and communication unit.
Figure 7C:
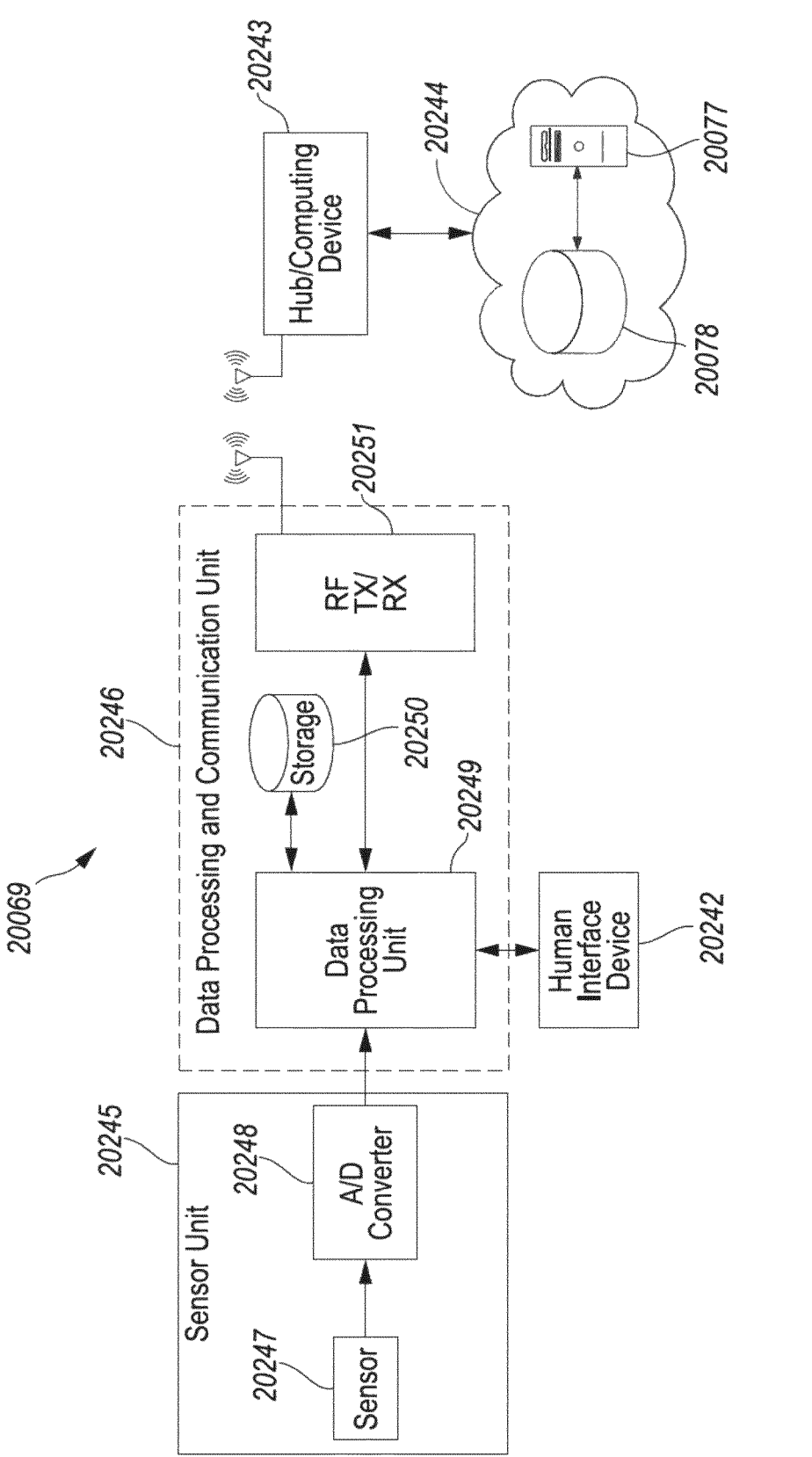
FIG. 7C shows an exemplary sensing system with a sensor unit and a data processing and communication unit.
Figure 7D:
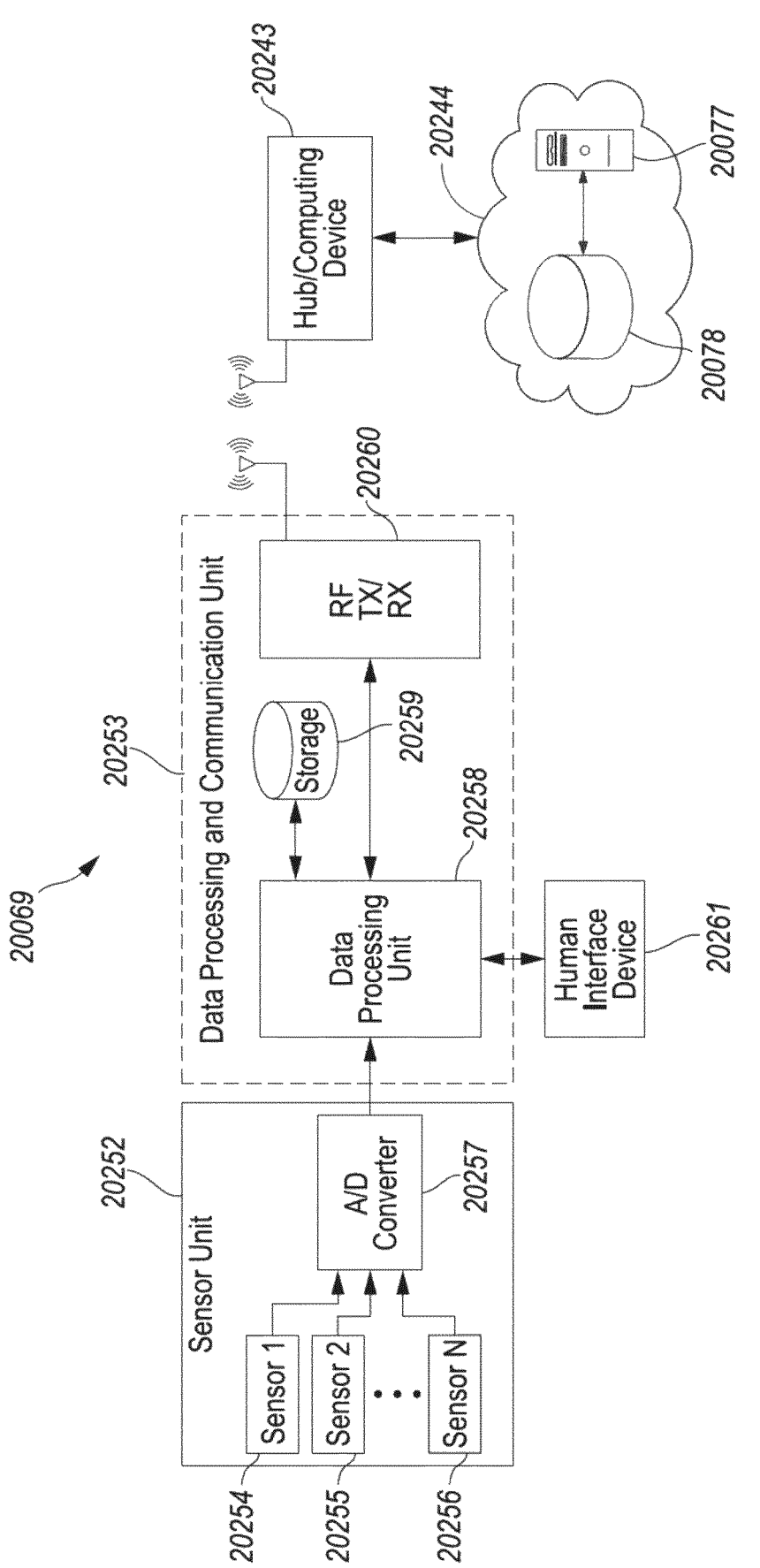
FIG. 7D shows an exemplary sensing system with a sensor unit and a data processing and communication unit.

The computing system 20063 of FIG. 4, FIG. 6B, the computing device 20200 of FIG. 6C, the hub/computing device 20243 of FIG. 7B, FIG. 7C, or FIG. 7D may be a surgical computing system or a hub device, a laptop, a tablet, a smart phone, etc.

As shown in FIG. 6B, a set of sensing systems 20069 and/or an environmental sensing system 20015 (as described in FIG. 2A) may be connected to the surgical hub system 20076 via the routers 20065. The routers 20065 may also provide a direct communication connection between the sensing systems 20069 and the cloud computing system 20064, for example, without involving the local computer system 20063 of the surgical hub system 20076. Communication from the surgical hub system 20076 to the cloud 20064 may be made either through a wired or a wireless communication channel.

As shown in FIG. 6B, the computer system 20063 may include a processor 20102 and a network interface 20100. The processor 20102 may be coupled to a radio frequency (RF) interface or a communication module 20103, storage 20104, memory 20105, non-volatile memory 20106, and input/output interface 20107 via a system bus, as described in FIG. 6A. The computer system 20063 may be connected with a local display unit 20108. In some examples, the display unit 20108 may be replaced by a HID. Details about the hardware and software components of the computer system are provided in FIG. 6A.

As shown in FIG. 6B, a sensing system 20069 may include a processor 20110. The processor 20110 may be coupled to a radio frequency (RF) interface 20114, storage 20113, memory (e.g., a non-volatile memory) 20112, and I/O interface 20111 via a system bus. The system bus can be any of several types of bus structure(s) including the memory bus or memory controller, a peripheral bus or external bus, and/or a local bus, as described herein. The processor 20110 may be any single-core or multicore processor as described herein.

It is to be appreciated that the sensing system 20069 may include software that acts as an intermediary between sensing system users and the computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

The sensing system 20069 may be connected to a human interface system 20115. The human interface system 20115 may be a touch screen display. The human interface system 20115 may include a human interface display for displaying information associated with a surgeon biomarker and/or a patient biomarker, display a prompt for a user action by a patient or a surgeon, or display a notification to a patient or a surgeon indicating information about a recovery millstone or a complication. The human interface system 20115 may be used to receive input from a patient or a surgeon. Other human interface systems may be connected to the sensing system 20069 via the I/O interface 20111. For example, the human interface device 20115 may include devices for providing a haptic feedback as a mechanism for prompting a user to pay attention to a notification that may be displayed on a display unit.

The sensing system 20069 may operate in a networked environment using logical connections to one or more remote computers, such as cloud computer(s), or local computers. The remote cloud computer(s) can be a personal computer, server, router, network PC, workstation, micro-processor-based appliance, peer device, or other common network node, and the like, and typically includes many or all of the elements described relative to the computer system. The remote computer(s) may be logically connected to the computer system through a network interface. The network interface may encompass communication networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

FIG. 6C illustrates an exemplary uncontrolled patient monitoring system, for example, when the patient is away from a healthcare facility. The uncontrolled patient monitoring system may be used for pre-surgical patient monitoring when a patient is being prepared for a surgical procedure but is away from a healthcare facility, or in post-surgical monitoring, for example, when a patient is recovering away from a healthcare facility.

As illustrated in FIG. 6C, one or more sensing systems 20069 are in communication with a computing device 20200, for example, a personal computer, a laptop, a tablet, or a smart phone. The computing system 20200 may provide processing for monitoring of various biomarkers associated with a patient, a notification mechanism to indicate that a milestone (e.g., a recovery milestone) is met or a complication is detected. The computing system 20200 may also provide instructions for the user of the sensing system to follow. The communication between the sensing systems 20069 and the computing device 20200 may be established directly using a wireless protocol as described herein or via the wireless router/hub 20211.

As shown in FIG. 6C, the sensing systems 20069 may be connected to the computing device 20200 via router 20211. The router 20211 may include wireless routers, wired switches, wired routers, wired or wireless networking hubs, etc. The router 20211 may provide a direct communication connection between the sensing systems 20069 and the cloud servers 20064, for example, without involving the local computing device 20200. The computing device 20200 may be in communication with the cloud server 20064. For example, the computing device 20200 may be in communication with the cloud 20064 through a wired or a wireless communication channel. In an example, a sensing system 20069 may be in communication with the cloud directly over a cellular network, for example, via a cellular base station 20210.

As shown in FIG. 6C, the computing device 20200 may include a processor 20203 and a network or an RF interface 20201. The processor 20203 may be coupled to a storage 20202, memory 20212, non-volatile memory 20213, and input/output interface 20204 via a system bus, as described in FIG. 6A and FIG. 6B. Details about the hardware and software components of the computer system are provided in FIG. 6A. The computing device 20200 may include a set of sensors, for example, sensor #1 20205, sensor #2 20206 up to sensor #n 20207. These sensors may be a part of the computing device 20200 and may be used to measure one or more attributes associated with the patient. The attributes may provide a context about a biomarker measurement performed by one of the sensing systems 20069. For example, sensor #1 may be an accelerometer that may be used to measure acceleration forces in order to sense movement or vibrations associated with the patient. In an example, the sensors 20205 to 20207 may include one or more of: a pressure sensor, an altimeter, a thermometer, a lidar, or the like.

As shown in FIG. 6B, a sensing system 20069 may include a processor, a radio frequency interface, a storage, a memory or non-volatile memory, and input/output interface via a system bus, as described in FIG. 6A. The sensing system may include a sensor unit and a processing and communication unit, as described in FIG. 7B through 7D. The system bus can be any of several types of bus structure(s) including the memory bus or memory controller, a peripheral bus or external bus, and/or a local bus, as described herein. The processor may be any single-core or multicore processor, as described herein.

The sensing system 20069 may be in communication with a human interface system 20215. The human interface system 20215 may be a touch screen display. The human interface system 20215 may be used to display information associated with a patient biomarker, display a prompt for a user action by a patient, or display a notification to a patient indicating information about a recovery millstone or a complication. The human interface system 20215 may be used to receive input from a patient. Other human interface systems may be connected to the sensing system 20069 via the I/O interface. For example, the human interface system may include devices for providing a haptic feedback as a mechanism for prompting a user to pay attention to a notification that may be displayed on a display unit. The sensing system 20069 may operate in a networked environment using logical connections to one or more remote computers, such as cloud computer(s), or local computers, as described in FIG. 6B.

FIG. 7A illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

In one aspect, the microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systems-based magnetic sensors, among others.

In one aspect, the position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

In one form, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5 and FIG. 6A.

FIG. 7B shows an example sensing system 20069. The sensing system may be a surgeon sensing system or a patient sensing system. The sensing system 20069 may include a sensor unit 20235 and a human interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, electroencephalography, colorimetry, impedimentary, potentiometry, amperometry, etc.

As illustrated in FIG. 7B, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RF transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC low-pass filter) before being sent to the ADC. The ADC may convert the measured physiological signal into measurement data associated with the biomarker. The ADC may pass measurement data to the data processing unit 20238 for processing. In an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), Wi-Fi. The data processing unit 20238 may send a notification (e.g., a notification for an HCP) directly to a cloud server via a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G. In an example, the sensing unit may be in communication with the hub/computing device via a router, as described in FIG. 6A through FIG. 6C.

FIG. 7C shows an example sensing system 20069 (e.g., a surgeon sensing system or a patient sensing system). The sensing system 20069 may include a sensor unit 20245, a data processing and communication unit 20246, and a human interface device 20242. The sensor unit 20245 may include a sensor 20247 and an analog-to-digital converted (ADC) 20248. The ADC 20248 in the sensor unit 20245 may convert a physiological signal measured by the sensor 20247 into measurement data associated with a biomarker. The sensor unit 20245 may send the measurement data to the data processing and communication unit 20246 for further processing. In an example, the sensor unit 20245 may send the measurement data to the data processing and communication unit 20246 using an inter-integrated circuit (I2C) interface.

The data processing and communication unit 20246 includes a data processing unit 20249, a storage unit 20250, and an RF transceiver 20251. The sensing system may be in communication with a surgical hub or a computing device 20243, which in turn may be in communication with a cloud computing system 20244. The cloud computing system 20244 may include a remote server 20077 and an associated remote storage 20078. The sensor unit 20245 may include one or more ex vivo or in vivo sensors for measuring one or more biomarkers, as described herein.

The data processing and communication unit 20246 after processing the measurement data received from the sensor unit 20245 may further process the measurement data and/or send the measurement data to the smart hub or the computing device 20243, as described in FIG. 7B. In an example, the data processing and communication unit 20246 may send the measurement data received from the sensor unit 20245 to the remote server 20077 of the cloud computing system 20244 for further processing and/or monitoring.

FIG. 7D shows an example sensing system 20069 (e.g., a surgeon sensing system or a patient sensing system). The sensing system 20069 may include a sensor unit 20252, a data processing and communication unit 20253, and a human interface system 20261. The sensor unit 20252 may include a plurality of sensors 20254, 20255 up to 20256 to measure one or more physiological signals associated with a patient or surgeon's biomarkers and/or one or more physical state signals associated with physical state of a patient or a surgeon. The sensor unit 20252 may also include one or more analog-to-digital converter(s) (ADCs) 20257. A list of biomarkers may include biomarkers such as those biomarkers disclosed herein. The ADC(s) 20257 in the sensor unit 20252 may convert each of the physiological signals and/or physical state signals measured by the sensors 20254-20256 into respective measurement data. The sensor unit 20252 may send the measurement data associated with one or more biomarkers as well as with the physical state of a patient or a surgeon to the data processing and communication unit 20253 for further processing. The sensor unit 20252 may send the measurement data to the data processing and communication unit 20253 individually for each of the sensors Sensor 1 20254 to Sensor N 20256 or combined for all the sensors. In an example, the sensor unit 20252 may send the measurement data to the data processing and communication unit 20253 via an I2C interface.

The data processing and communication unit 20253 may include a data processing unit 20258, a storage unit 20259, and an RF transceiver 20260. The sensing system 20069 may be in communication with a surgical hub or a computing device 20243, which in turn is in communication with a cloud computing system 20244 comprising at least one remote server 20077 and at least one storage unit 20078. The sensor units 20252 may include one or more ex vivo or in vivo sensors for measuring one or more biomarkers, as described herein.

Figure 8:
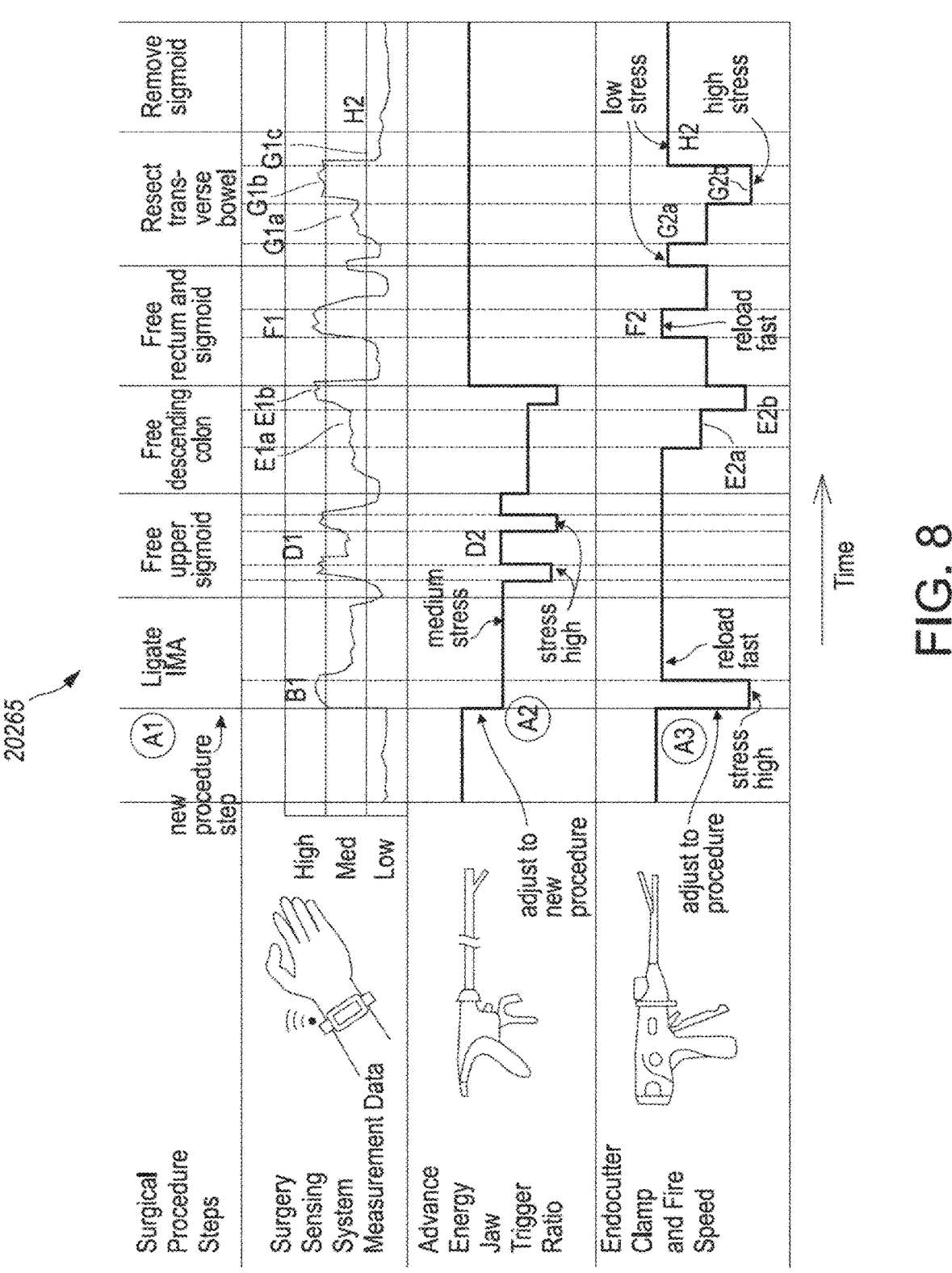
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more surgeon sensing systems to adjust surgical instrument controls. FIG. 8 illustrates a timeline 20265 of an illustrative surgical procedure and the contextual information that a surgical hub can derive from data received from one or more surgical devices, one or more surgeon sensing systems, and/or one or more environmental sensing systems at each step in the surgical procedure. The devices that could be controlled by a surgical hub may include advanced energy devices, endocutter clamps, etc. The surgeon sensing systems may include sensing systems for measuring one or more biomarkers associated with the surgeon, for example, heart rate, sweat composition, respiratory rate, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time a healthcare provider (HCP) utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems 20069 to continually derive inferences (i.e., contextual information) about an HCP's stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 worn by different HCPs.

Once each of the devices is ready and pre-surgical preparation is complete, the surgical team may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1*a*, E1*b*, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the HCP is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, during time period G1*b*, a control signal G2*b* may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
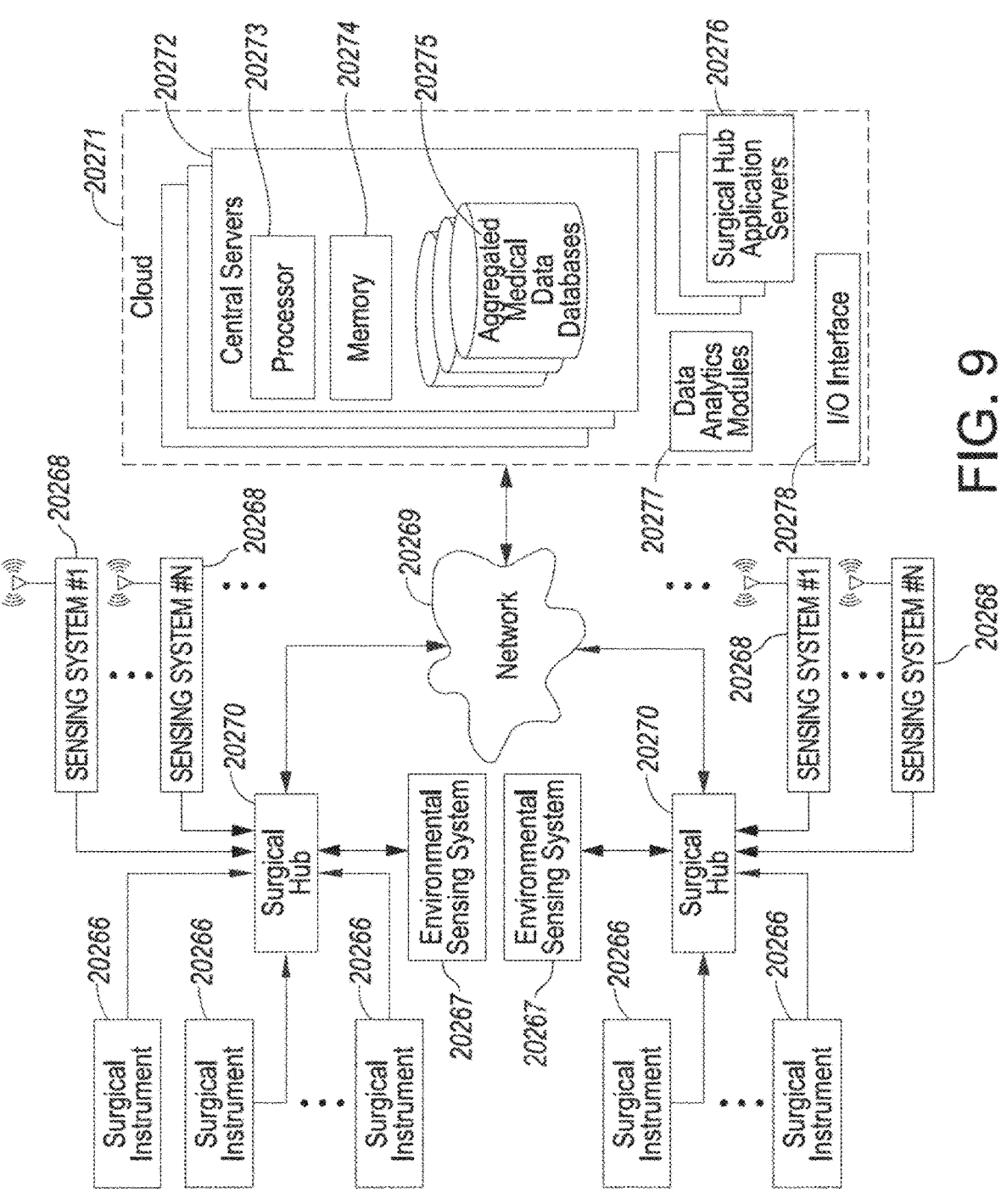
FIG. 9 is a block diagram of the computer-implemented interactive surgeon/patient monitoring system.

FIG. 9 is a block diagram of the computer-implemented interactive surgical system with surgeon/patient monitoring, in accordance with at least one aspect of the present disclosure. In one aspect, the computer-implemented interactive surgical system may be configured to monitor surgeon biomarkers and/or patient biomarkers using one or more sensing systems 20069. The surgeon biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The cloud-based analytics system may include one or more analytics servers.

As illustrated in FIG. 9, the cloud-based monitoring and analytics system may comprise a plurality of sensing systems 20268 (may be the same or similar to the sensing systems 20069), surgical instruments 20266 (may be the same or similar to instruments 20031), a plurality of surgical hubs 20270 (may be the same or similar to hubs 20006), and a surgical data network 20269 (may be the same or similar to the surgical data network described in FIG. 4) to couple the surgical hubs 20270 to the cloud 20271 (may be the same or similar to cloud computing system 20064). Each of the plurality of surgical hubs 20270 may be communicatively coupled to one or more surgical instruments 20266. Each of the plurality of surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The cloud system 20271 may be a remote centralized source of hardware and software for storing, processing, manipulating, and communicating measurement data from the sensing systems 20268 and data generated based on the operation of various surgical systems 20268.

As shown in FIG. 9, access to the cloud system 20271 may be achieved via the network 20269, which may be the Internet or some other suitable computer network. Surgical hubs 20270 that may be coupled to the cloud system 20271 can be considered the client side of the cloud computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical surgeon monitoring of surgeon related biomarkers, pre-surgical patient monitoring, in-surgical patient monitoring, or post-surgical monitoring of patient biomarkers to track and/or measure various milestones and/or detect various complications. Environmental sensing systems 20267 may be paired with surgical hubs 20270 measuring environmental attributes associated with a surgeon or a patient for surgeon monitoring, pre-surgical patient monitoring, in-surgical patient monitoring, or post-surgical monitoring of patient.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the cloud system 20271 may include one or more central servers 20272 (may be same or similar to remote server 20067), surgical hub application servers 20276, data analytics modules 20277, and an input/output ("I/O") interface 20278. The central servers 20272 of the cloud system 20271 may collectively administer the cloud computing system, which includes monitoring requests by client surgical hubs 20270 and managing the processing capacity of the cloud system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may comprise aggregated medical data databases 20275, which can reside in the memory 20274.

Based on connections to various surgical hubs 20270 via the network 20269, the cloud 20271 can aggregate data from specific data generated by various surgical instruments 20266 and/or monitor real-time data from sensing systems 20268 and the surgical hubs 20270 associated with the surgical instruments 20266 and/or the sensing systems 20268. Such aggregated data from the surgical instruments 20266 and/or measurement data from the sensing systems 20268 may be stored within the aggregated medical databases 20275 of the cloud 20271. In particular, the cloud 20271 may advantageously track real-time measurement data from the sensing systems 20268 and/or perform data analysis and operations on the measurement data and/or the aggregated data to yield insights and/or perform functions that individual hubs 20270 could not achieve on their own. To this end, as shown in FIG. 9, the cloud 20271 and the surgical hubs 20270 are communicatively coupled to transmit and receive information. The I/O interface 20278 is connected to the plurality of surgical hubs 20270 via the network 20269. In this way, the I/O interface 20278 can be configured to transfer information between the surgical hubs 20270 and the aggregated medical data databases 20275. Accordingly, the I/O interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the cloud 20271 to surgical hubs 20270. The hub application servers 20276 of the cloud 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The cloud computing system configuration described in the present disclosure may be designed to address various issues arising in the context of medical operations (e.g., pre-surgical monitoring, in-surgical monitoring, and post-surgical monitoring) and procedures performed using medical devices, such as the surgical instruments 20266, 20031. In particular, the surgical instruments 20266 may be digital surgical devices configured to interact with the cloud 20271 for implementing techniques to improve the performance of surgical operations. The sensing systems 20268 may be systems with one or more sensors that are configured to measure one or more biomarkers associated with a surgeon perfuming a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that clinicians and/or patients may control aspects of interaction between the surgical instruments 20266 or the sensing system 20268 and the cloud 20271. Other suitable user interfaces for control such as auditory controlled user interfaces may also be used.

The cloud computing system configuration described in the present disclosure may be designed to address various issues arising in the context of monitoring one or more biomarkers associated with a healthcare professional (HCP) or a patient in pre-surgical, in-surgical, and post-surgical procedures using sensing systems 20268. Sensing systems 20268 may be surgeon sensing systems or patient sensing systems configured to interact with the surgical hub 20270 and/or with the cloud system 20271 for implementing techniques to monitor surgeon biomarkers and/or patient biomarkers. Various sensing systems 20268 and/or surgical hubs 20270 may comprise touch-controlled human interface systems such that the HCPs or the patients may control aspects of interaction between the sensing systems 20268 and the surgical hub 20270 and/or the cloud systems 20271. Other suitable user interfaces for control such as auditory controlled user interfaces may also be used.

Figure 10:
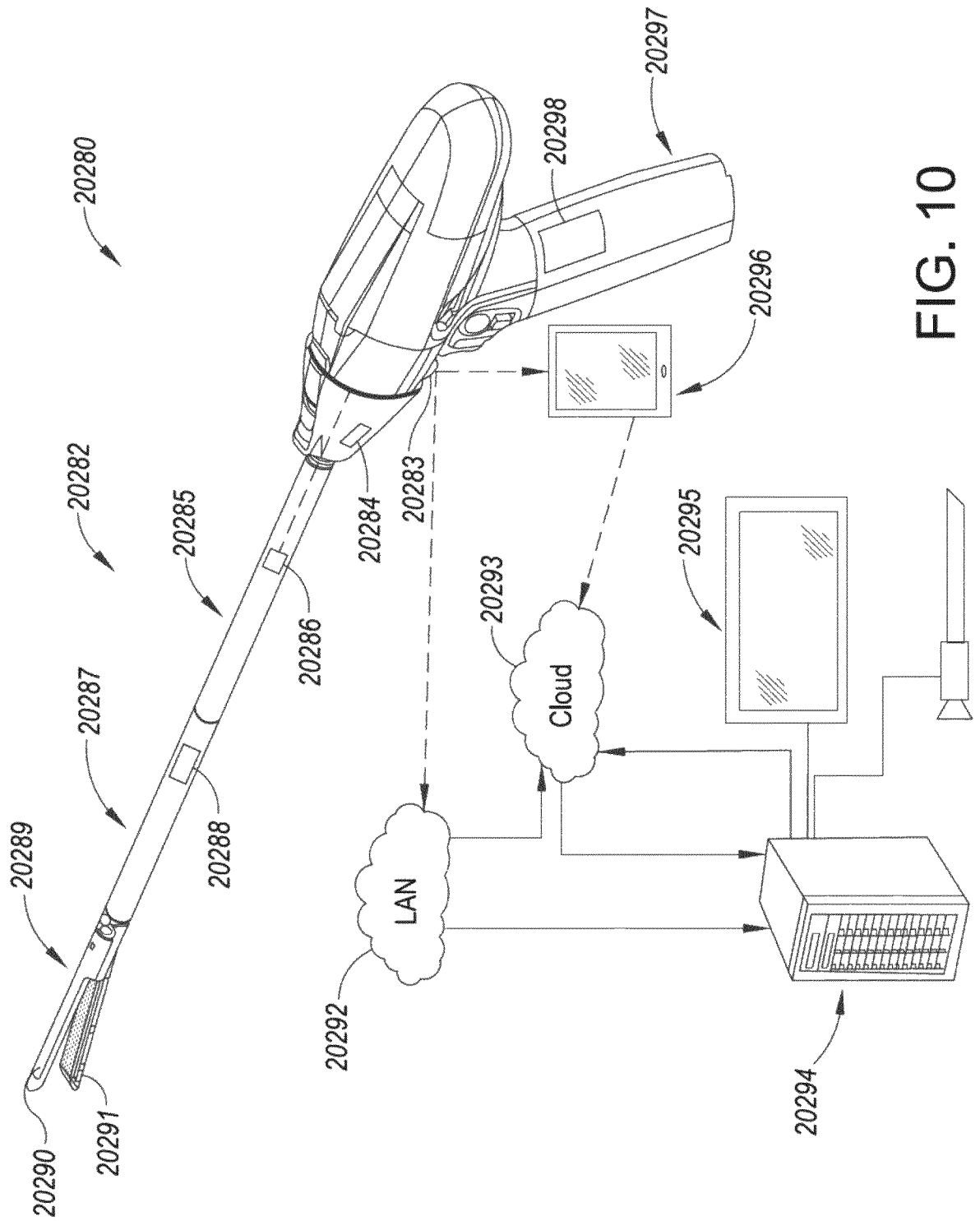
FIG. 10 shows an example surgical system that includes a handle having a controller and a motor, an adapter releasably coupled to the handle, and a loading unit releasably coupled to the adapter.

FIG. 10 illustrates an example surgical system 20280 in accordance with the present disclosure and may include a surgical instrument 20282 that can be in communication with a console 20294 or a portable device 20296 through a local area network 20292 or a cloud network 20293 via a wired or wireless connection. In various aspects, the console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figures 11A, 11B, 11C, 11D:
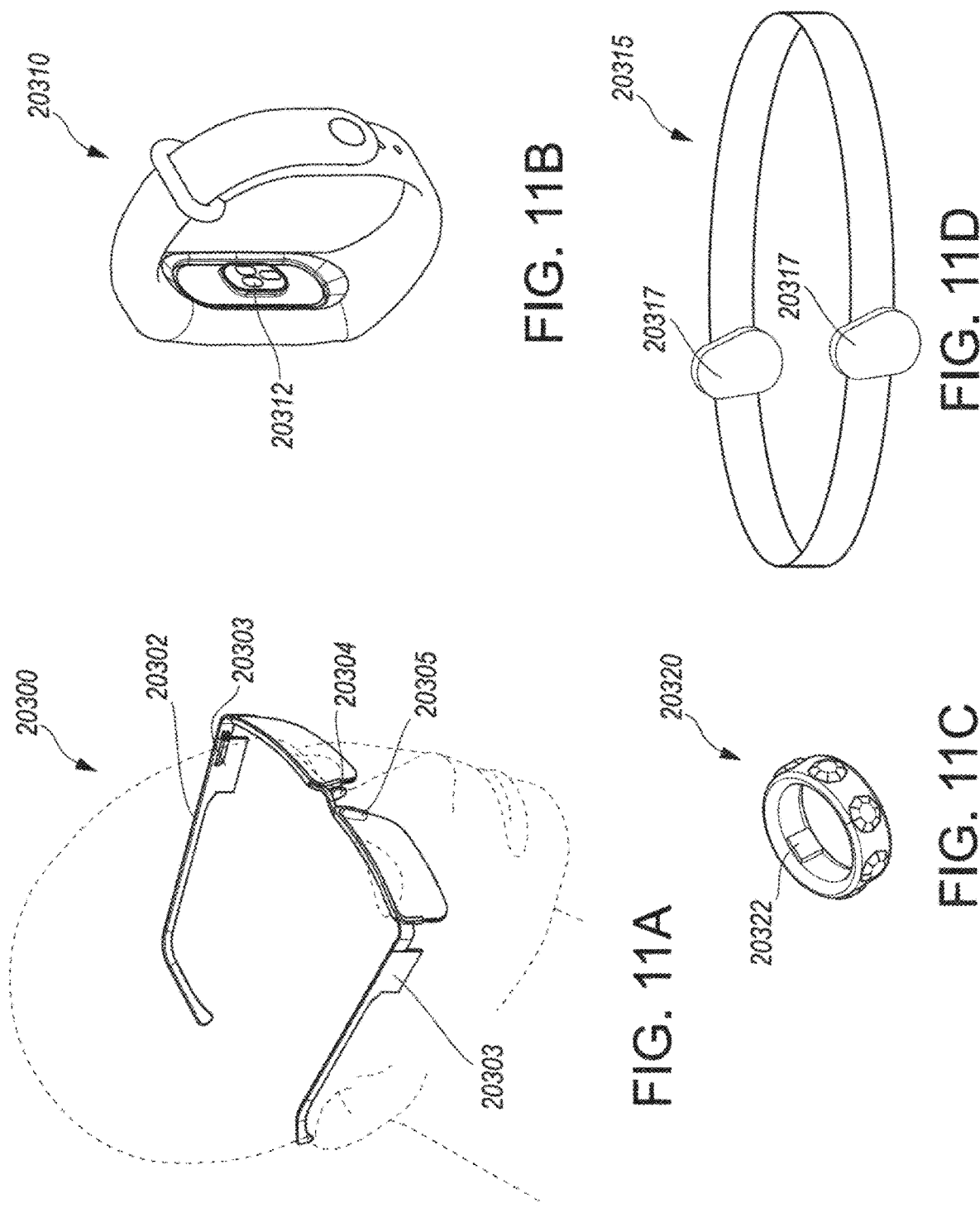
FIGS. 11A-11D illustrate examples of sensing systems that may be used for monitoring surgeon biomarkers or patient biomarkers.

FIG. 11A to FIG. 11D illustrates examples of wearable sensing systems, e.g., surgeon sensing systems or patient sensing systems. FIG. 11A is an example of eyeglasses-based sensing system 20300 that may be based on an electrochemical sensing platform. The sensing system 20300 may be capable of monitoring (e.g., real-time monitoring) of sweat electrolytes and/or metabolites using multiple sensors 20304 and 20305 that are in contact with the surgeon's or patient's skin. For example, the sensing system 20300 may use an amperometry based biosensor 20304 and/or a potentiometry based biosensor 20305 integrated with the nose bridge pads of the eyeglasses 20302 to measure current and/or the voltage.

The amperometric biosensor 20304 may be used to measure sweat lactate levels (e.g., in mmol/L). Lactate that is a product of lactic acidosis that may occur due to decreased tissue oxygenation, which may be caused by sepsis or hemorrhage. A patient's lactate levels (e.g., >2 mmol/L) may be used to monitor the onset of sepsis, for example, during post-surgical monitoring. The potentiometric biosensor 20305 may be used to measure potassium levels in the patient's sweat. A voltage follower circuit with an operational amplifier may be used for measuring the potential signal between the reference and the working electrodes. The output of the voltage follower circuit may be filtered and converted into a digital value using an ADC.

The amperometric sensor 20304 and the potentiometric sensor 20305 may be connected to circuitries 20303 placed on each of the arms of the eyeglasses. The electrochemical sensors may be used for simultaneous real-time monitoring of sweat lactate and potassium levels. The electrochemical sensors may be screen printed on stickers and placed on each side of the glasses nose pads to monitor sweat metabolites and electrolytes. The electronic circuitries 20303 placed on the arms of the glasses frame may include a wireless data transceiver (e.g., a low energy Bluetooth transceiver) that may be used to transmit the lactate and/or potassium measurement data to a surgical hub or an intermediary device that may then forward the measurement data to the surgical hub. The eyeglasses-based sensing system 20300 may use signal conditioning unit to filter and amplify the electrical signal generated from the electrochemical sensors 20305 or 20304, a microcontroller to digitize the analog signal, and a wireless (e.g., a low energy Bluetooth) module to transfer the data to a surgical hub or a computing device, for example, as described in FIGS. 7B through 7D.

FIG. 11B is an example of a wristband-type sensing system 20310 comprising a sensor assembly 20312 (e.g., Photoplethysmography (PPG)-based sensor assembly or Electrocardiogram (ECG) based-sensor assembly). For example, in the sensing system 20310, the sensor assembly 20312 may collect and analyze arterial pulse in the wrist. The sensor assembly 20312 may be used to measure one or more biomarkers (e.g., heart rate, heart rate variability (HRV), etc.). In case of a sensing system with a PPG-based sensor assembly 20312, light (e.g., green light) may be passed through the skin. A percentage of the green light may be absorbed by the blood vessels and some of the green light may be reflected and detected by a photodetector. These differences or reflections are associated with the variations in the blood perfusion of the tissue and the variations may be used in detecting the heart-related information of the cardiovascular system (e.g., heart rate). For example, the amount of absorption may vary depending on the blood volume. The sensing system 20310 may determine the heart rate by measuring light reflectance as a function of time. HRV may be determined as the time period variation (e.g., standard deviation) between the steepest signal gradient prior to a peak, known as inter-beat intervals (IBIs).

In the case of a sensing system with an ECG-based sensor assembly 20312, a set of electrodes may be placed in contact with skin. The sensing system 20310 may measure voltages across the set of electrodes placed on the skin to determine heart rate. HRV in this case may be measured as the time period variation (e.g., standard deviation) between R peaks in the QRS complex, known as R-R intervals.

The sensing system 20310 may use a signal conditioning unit to filter and amplify the analog PPG signal, a microcontroller to digitize the analog PPG signal, and a wireless (e.g., a Bluetooth) module to transfer the data to a surgical hub or a computing device, for example, as described in FIGS. 7B through 7D.

FIG. 11C is an example ring sensing system 20320. The ring sensing system 20320 may include a sensor assembly (e.g., a heart rate sensor assembly) 20322. The sensor assembly 20322 may include a light source (e.g., red or green light emitting diodes (LEDs)), and photodiodes to detect reflected and/or absorbed light. The LEDs in the sensor assembly 20322 may shine light through a finger and the photodiode in the sensor assembly 20322 may measure heart rate and/or oxygen level in the blood by detecting blood volume change. The ring sensing system 20320 may include other sensor assemblies to measure other biomarkers, for example, a thermistor or an infrared thermometer to measure the surface body temperature. The ring sensing system 20320 may use a signal conditioning unit to filter and amplify the analog PPG signal, a microcontroller to digitize the analog PPG signal, and a wireless (e.g., a low energy Bluetooth) module to transfer the data to a surgical hub or a computing device, for example, as described in FIGS. 7B through 7D.

FIG. 11D is an example of an electroencephalogram (EEG) sensing system 20315. As illustrated in FIG. 11D, the sensing system 20315 may include one or more EEG sensor units 20317. The EEG sensor units 20317 may include a plurality of conductive electrodes placed in contact with the scalp. The conductive electrodes may be used to measure small electrical potentials that may arise outside of the head due to neuronal action within the brain. The EEG sensing system 20315 may measure a biomarker, for example, delirium by identifying certain brain patterns, for example, a slowing or dropout of the posterior dominant rhythm and loss of reactivity to eyes opening and closing. The ring sensing system 20315 may have a signal conditioning unit for filtering and amplifying the electrical potentials, a microcontroller to digitize the electrical signals, and a wireless (e.g., a low energy Bluetooth) module to transfer the data to a smart device, for example, as described in FIGS. 7B through 7D.

Figure 12:
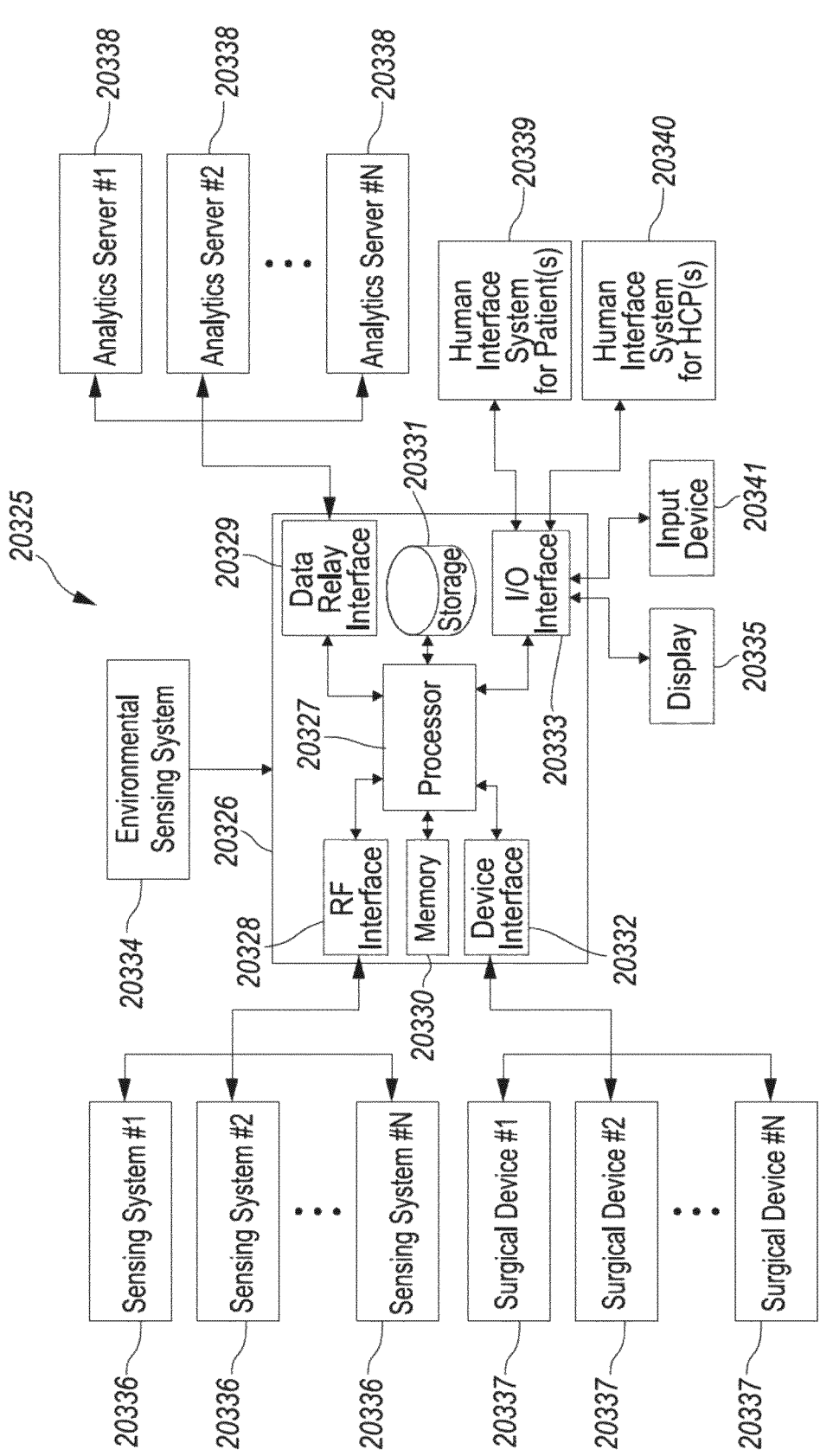
FIG. 12 is a block diagram of a patient monitoring system or a surgeon monitoring system.

FIG. 12 illustrates a block diagram of a computer-implemented patient/surgeon monitoring system 20325 for monitoring one or more patient or surgeon biomarkers prior to, during, and/or after a surgical procedure. As illustrated in FIG. 12, one or more sensing systems 20336 may be used to measure and monitor the patient biomarkers, for example, to facilitate patient preparedness before a surgical procedure, and recovery after a surgical procedure. Sensing systems 20336 may be used to measure and monitor the surgeon biomarkers in real-time, for example, to assist surgical tasks by communicating relevant biomarkers (e.g., surgeon biomarkers) to a surgical hub 20326 and/or the surgical devices 20337 to adjust their function. The surgical device functions that may be adjusted may include power levels, advancement speeds, closure speed, loads, wait times, or other tissue dependent operational parameters. The sensing systems 20336 may also measure one or more physical attributes associated with a surgeon or a patient. The patient biomarkers and/or the physical attributes may be measured in real time.

The computer-implemented wearable patient/surgeon wearable sensing system 20325 may include a surgical hub 20326, one or more sensing systems 20336, and one or more surgical devices 20337. The sensing systems and the surgical devices may be communicably coupled to the surgical hub 20326. One or more analytics servers 20338, for example part of an analytics system, may also be communicably coupled to the surgical hub 20326. Although a single surgical hub 20326 is depicted, it should be noted that the wearable patient/surgeon wearable sensing system 20325 may include any number of surgical hubs 20326, which can be connected to form a network of surgical hubs 20326 that are communicably coupled to one or more analytics servers 20338, as described herein.

In an example, the surgical hub 20326 may be a computing device. The computing device may be a personal computer, a laptop, a tablet, a smart mobile device, etc. In an example, the computing device may be a client computing device of a cloud-based computing system. The client computing device may be a thin client.

In an example, the surgical hub 20326 may include a processor 20327 coupled to a memory 20330 for executing instructions stored thereon, a storage 20331 to store one or more databases such as an EMR database, and a data relay interface 20329 through which data is transmitted to the analytics servers 20338. In an example, the surgical hub 20326 further may include an I/O interface 20333 having an input device 20341 (e.g., a capacitive touchscreen or a keyboard) for receiving inputs from a user and an output device 20335 (e.g., a display screen) for providing outputs to a user. In an example, the input device and the output device may be a single device. Outputs may include data from a query input by the user, suggestions for products or a combination of products to use in a given procedure, and/or instructions for actions to be carried out before, during, and/or after a surgical procedure. The surgical hub 20326 may include a device interface 20332 for communicably coupling the surgical devices 20337 to the surgical hub 20326. In one aspect, the device interface 20332 may include a transceiver that may enable one or more surgical devices 20337 to connect with the surgical hub 20326 via a wired interface or a wireless interface using one of the wired or wireless communication protocols described herein. The surgical devices 20337 may include, for example, powered staplers, energy devices or their generators, imaging systems, or other linked systems, for example, smoke evacuators, suction-irrigation devices, insufflation systems, etc.

In an example, the surgical hub 20326 may be communicably coupled to one or more surgeon and/or patient sensing systems 20336. The sensing systems 20336 may be used to measure and/or monitor, in real-time, various biomarkers associated with a surgeon performing a surgical procedure or a patient on whom a surgical procedure is being performed. A list of the patient/surgeon biomarkers measured by the sensing systems 20336 is provided herein. In an example, the surgical hub 20326 may be communicably coupled to an environmental sensing system 20334. The environmental sensing systems 20334 may be used to measure and/or monitor, in real-time, environmental attributes, for example, temperature/humidity in the surgical theater, surgeon movements, ambient noise in the surgical theater caused by the surgeon's and/or the patient's breathing pattern, etc.

When sensing systems 20336 and the surgical devices 20337 are connected to the surgical hub 20326, the surgical hub 20326 may receive measurement data associated with one or more patient biomarkers, physical state associated with a patient, measurement data associated with surgeon biomarkers, and/or physical state associated with the surgeon from the sensing systems 20336, for example, as illustrated in FIG. 7B through 7D. The surgical hub 20326 may associate the measurement data, e.g., related to a surgeon, with other relevant pre-surgical data and/or data from situational awareness system to generate control signals for controlling the surgical devices 20337, for example, as illustrated in FIG. 8.

In an example, the surgical hub 20326 may compare the measurement data from the sensing systems 20336 with one or more thresholds defined based on baseline values, pre-surgical measurement data, and/or in surgical measurement data. The surgical hub 20326 may compare the measurement data from the sensing systems 20336 with one or more thresholds in real-time. The surgical hub 20326 may generate a notification for displaying. The surgical hub 20326 may send the notification for delivery to a human interface system for patient 20339 and/or the human interface system for a surgeon or an HCP 20340, for example, if the measurement data crosses (e.g., is greater than or lower than) the defined threshold value. The determination whether the notification would be sent to one or more of the to the human interface system for patient 20339 and/or the human interface system for an HCP 2340 may be based on a severity level associated with the notification. The surgical hub 20326 may also generate a severity level associated with the notification for displaying. The severity level generated may be displayed to the patient and/or the surgeon or the HCP. In an example, the patient biomarkers to be measured and/or monitored (e.g., measured and/or monitored in real-time) may be associated with a surgical procedural step. For example, the biomarkers to be measured and monitored for transection of veins and arteries step of a thoracic surgical procedure may include blood pressure, tissue perfusion pressure, edema, arterial stiffness, collagen content, thickness of connective tissue, etc., whereas the biomarkers to be measured and monitored for lymph node dissection step of the surgical procedure may include monitoring blood pressure of the patient. In an example, data regarding postoperative complications could be retrieved from an EMR database in the storage 20331 and data regarding staple or incision line leakages could be directly detected or inferred by a situational awareness system. The surgical procedural outcome data can be inferred by a situational awareness system from data received from a variety of data sources, including the surgical devices 20337, the sensing systems 20336, and the databases in the storage 20331 to which the surgical hub 20326 is connected.

The surgical hub 20326 may transmit the measurement data and physical state data it received from the sensing systems 20336 and/or data associated with the surgical devices 20337 to analytics servers 20338 for processing thereon. Each of the analytics servers 20338 may include a memory and a processor coupled to the memory that may execute instructions stored thereon to analyze the received data. The analytics servers 20338 may be connected in a distributed computing architecture and/or utilize a cloud computing architecture. Based on this paired data, the analytics system 20338 may determine optimal and/or preferred operating parameters for the various types of modular devices, generate adjustments to the control programs for the surgical devices 20337, and transmit (or "push") the updates or control programs to the one or more surgical devices 20337. For example, an analytics system 20338 may correlate the perioperative data it received from the surgical hub 20236 with the measurement data associated with a physiological state of a surgeon or an HCP and/or a physiological state of the patient. The analytics system 20338 may determine when the surgical devices 20337 should be controlled and send an update to the surgical hub 20326. The surgical hub 20326 may then forward the control program to the relevant surgical device 20337.

Additional detail regarding the computer-implemented wearable patient/surgeon wearable sensing system 20325, including the surgical hub 30326, one or more sensing systems 20336 and various surgical devices 20337 connectable thereto, are described in connection with FIG. 5 through FIG. 7D.

Thoracic surgery may refer to operations on organs in the chest, such as the heart, lungs, and esophagus, etc. Thoracic surgery may include, for example, coronary artery bypass surgery, heart transplant, lung transplant, and removal of parts of the lung (e.g., affected by cancer). Thoracic surgery may include procedural steps, such as dissect parenchyma, transect arteries and veins, transect parenchyma, and dissect lymph nodes. Patients may be monitored before, during, and/or after surgery. Pre-surgery and/or in-surgery monitoring may impact, for example, a surgical procedure and/or post-surgical monitoring. Post-surgery patient monitoring for recovery milestones and/or complications may be based on (e.g., adapted to), for example, a type of surgery, a surgical procedure, information derived from pre-surgery monitoring, and/or information derived from in-surgery monitoring.

Patient monitoring (e.g., post-surgical or recovery monitoring), such as thoracic surgery post-surgical monitoring, may (e.g., be used to) track recovery milestones, predict complications, and/or make recommendations (e.g., to reduce the severity of complications and/or to avoid complications). For example, an occurrence of a thoracic post-surgical complication may be predicted or detected by one or more computing systems (e.g., a surgical hub, a (wearable) sensing system, and/or the like). Monitoring (e.g., using one or more sensors) may be based on one or more (e.g., potential and/or actual) complications and/or recovery milestones (e.g., healing cascade milestones). Complications may include, for example, prolonged air leaks (PALs), infection, pulmonary insufficiency, arrhythmias, residual intrapleural air spaces, postpneumonectomy empyema, bronchopleural fistula, cardiac herniation, lobar gangrene, esophagopleural fistula, etc. For example, monitoring may (e.g., based on potential and/or actual complication and/or recovery milestones for a type of surgery) monitor for air leak incidence or progression, lung collapse, limited lung volume, irregular respiration, etc.

Monitoring (e.g., pre-, in- and/or post-surgical monitoring) may monitor one or more patient biomarkers. For example, post-surgical (e.g., recovery) monitoring may monitor patient biomarkers to track recovery metrics and/or complications for a surgery, such as lung surgery. Post-surgery monitoring of patient biomarkers may (e.g., be used to) track healing stage progress or recovery milestones and/or determine a probability of complications, which may, for example, result in PALs (e.g., after thoracic resection of a lung). Healing progress and/or development of one or more complications, for example, based on (e.g., using) one or more of baseline records (e.g., developed as described herein), monitored patient biomarkers (e.g., VO2 max, respiration rate, heart rate variability, physical reaction(s) such as coughing and/or sneezing, oxygen saturation), surgical results or modifications (e.g., lung volume reduction), and/or recovery milestones. Recovery milestones and/or complications may be based on (e.g., indicated by) one or more thresholds (e.g., threshold values associated with a patient biomarker), for example, relative to one or more time limits (e.g., predetermined amount(s) of time). For example, failure to achieve a recovery milestone (e.g., within a timeframe, such as a time relative to surgery) alone and/or in combination with patient biomarker values may indicate that one or more complications may be developing or have developed in the patient. Complication mitigation may be supported, for example, by reporting (e.g., of one or more patient biomarker values and/or results of one or more analyses), for example, to a health care provider (HCP). For example, one or more recommendations (e.g., behavioral, medication, bandaging) may be developed based on reporting of monitored patient biomarker values (e.g., measurements) and/or analyses.

Predictions of complications and/or recovery milestones may be generated, for example, by one or more machine learning (ML) models, such as predictive models, trained to make predictions after being trained on training data. For example, one or more ML classification algorithms may predict one or more types/classes of complications and/or recovery milestones by inference from input data. A model trained on vectorized training data may process vectorized input data. For example, a model may receive vectorized patient-specific data as input and classify the data as being indicative of one or more complications and/or one or more recovery milestones (e.g., each associated with a probability, likelihood, or confidence level). The model may receive updated patient-specific data to update predicted complications and probabilities and/or recovery milestones and probabilities. Complication mitigation (e.g., recommended actions or recommendations) may be based, at least in part, on one or more complications (e.g., and probabilities) generated by one or more models. A trained model may be any type of processing logic that performs an analysis and generates a prediction or determination derived from or generated based on empirical data, which may be referred to interchangeably as logic, an algorithm, a model, an ML algorithm or model, a neural network (NN), deep learning, artificial intelligence (AI), and so on.

Figure 13:
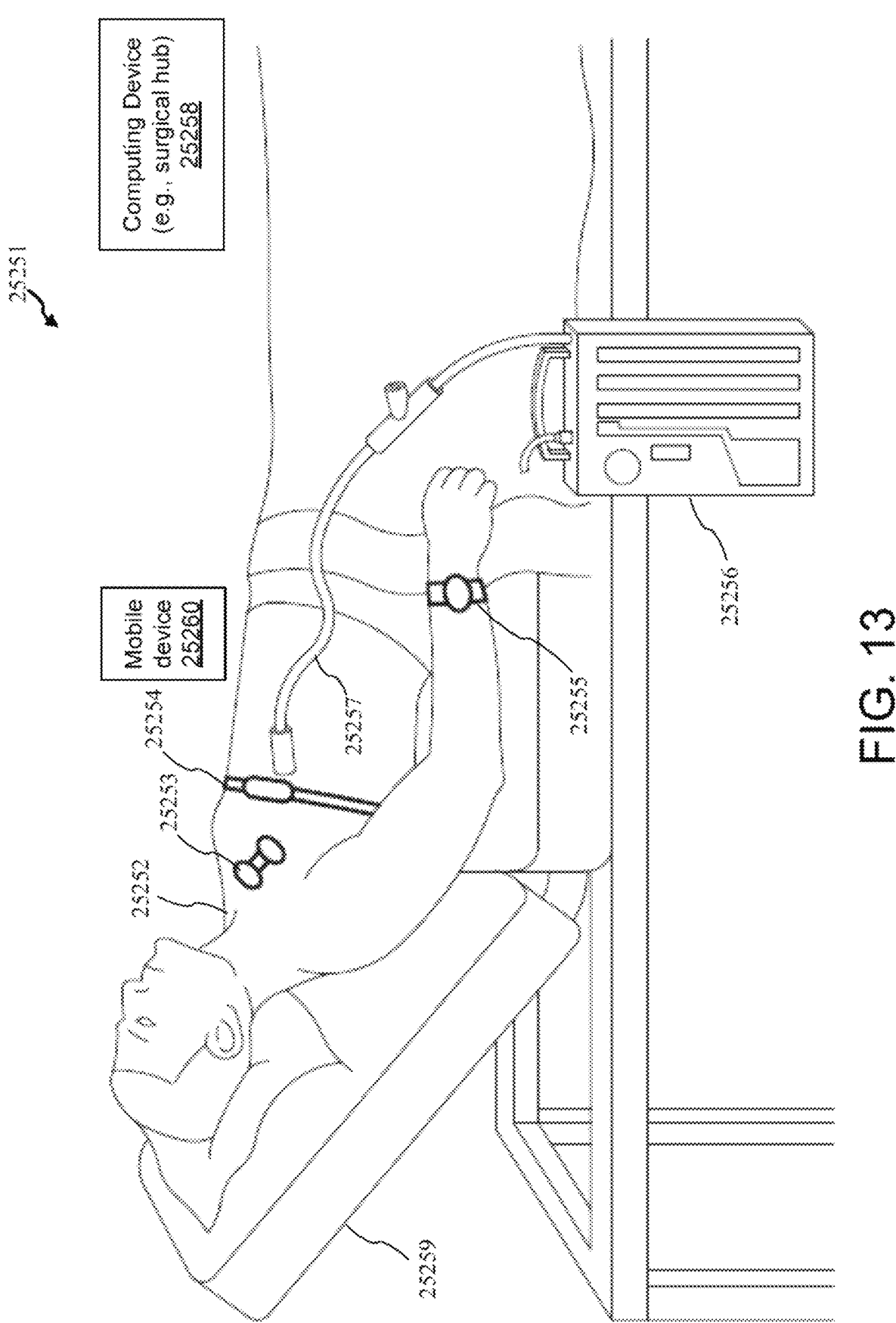
FIG. 13 shows an example of a patient monitoring system, in accordance with at least one aspect of the present disclosure.

FIG. 13 shows an example of a patient monitoring system, including patient wearable sensing systems, a controllable device, and a computing system or a computing device (e.g., a surgical hub), in accordance with at least one aspect of the present disclosure. Patient monitoring system 25251 may include (e.g., as shown by example in FIG. 13) first wearable sensing system 25253, second wearable sensing system 25254, third wearable sensing system 25255, controllable device 25256, and computing system or computing device (e.g., a surgical hub) 25258.

As discussed in various examples herein, a patient (e.g., patient 25252) may wear one or more devices with one or more sensors (e.g., first wearable sensing system 25253, second wearable sensing system 25254, and/or third wearable sensing system 25255) pre-, in-, and/or post-surgery to measure one or more patient biomarkers (e.g., VO2 max, respiration rate, heart rate variability (HRV), physical reaction(s) such as coughing and/or sneezing, oxygen saturation, respiratory rate, respiratory phase, diaphragmatic muscle tone, temperature, sweat, ECG, hydration state, tissue perfusion). Wearable sensing systems may include sensors that may be used to sense, monitor, or measure one or more patient biomarkers on and/or in any portion of a human body (e.g., wrist, arm, chest, waist, leg, foot, head, mouth) as discussed in FIGS. 11A-11D and FIGS. 7B-7D. For example, wearable sensor 25253 may be worn on the chest (e.g., near the clavicle), for example, to monitor one or more patient biomarkers (e.g., patient temperature, heart rate, HRV, coughing, sneezing, etc.). Second wearable sensor 25254 may be worn as a chest strap, for example, to monitor one or more of respiration information (e.g., respiratory rate, respiratory phase, such as inhale or exhale), diaphragmatic muscle tone (e.g., to provide a predictive value, such as ahead of a cough), temperature, heart rate, HRV, coughing, sweat, electrocardiogram (ECG), electromyography (EMG), mechanomyogram (MMG), hydration state, tissue perfusion, and/or other patient biomarkers. Third wearable sensing system 25255 is shown as a wrist strap (e.g., a watch or bracelet), which may be used to monitor, one or more patient biomarkers (e.g., heart rate, HRV, coughing, sweat, ECG, hydration state, tissue perfusion, and/or other patient biomarkers).

As discussed in various examples herein, one or more controllable devices (e.g., controllable device 25256) may be automatically and/or manually controlled by one or more recommendations generated based (e.g., at least in part) on one or more patient biomarkers monitored pre-, in- and/or post-surgery. The controllable device may also act as a sensing device that is communicatively coupled with the computing system or the surgical hub. In the example shown in FIG. 13, controllable device 25256 may be a portable pump controlled by a control program. Controllable device 25256 may control pressure or airflow (e.g., suction) in chest tube 25257 inserted into the chest of patient 25252 (e.g., to reduce pressure on an organ such as a lung and drain air, blood, or fluid from the pleural space around a lung). Controllable device 25256 and/or chest tube 25257 may incorporate one or more sensors and/or sensing systems (e.g., not shown). For example, one or more (e.g., in line sensors) in controllable device 25256 and/or chest tube 25257 may measure air flow or air volume in chest tube 25257 overtime. One or more patient biomarkers may be measured and analyzed (e.g., to determine a phase of respiration) for use in regulating airflow in chest tube 25257. A control program in controllable device 25256 may be configured to modulate a suction level in chest tube 25257 connected to patient 25252, for example, based on the detected phase of respiration.

As discussed in various examples herein, one or more hubs (e.g., hub 25258) may be in communication with one or more of sensing systems (e.g., first, second and third sensing systems 25253, 25254, 25255) and one or more controllable devices (e.g., controllable device 25256), mobile device 25260, etc. In an example, the mobile device 25260 may perform all the functions of a sensing system and/or act as human interface device (HID) as described herein. In an example, the mobile device 25260 may be a computing device that may be an equivalent of the computing device 25258, as described herein in FIG. 2B. Hub 25258 may be configured to perform one or more of the following: receive and process patient biomarker measurements from one or more sensing systems, determine patient biomarker measurement thresholds, generate (e.g., patient-specific) predictions regarding potential complications, generate and transmit notifications and/or recommendations (e.g., to a patient sensing system 25255 or a mobile device 25260) for displaying to a patient and/or to controllable device 25256 to operate controllable device(s), and/or the like. For example, hub 25258 may receive measurement data associated with patient biomarker(s) from first, second and third sensing systems 25253, 25254, 25255, generate predicted complications to monitor patient for, determine patient monitoring thresholds for recovery milestones and/or complications, analyze patient biomarker measurements relative to the thresholds for the predicted complications and/or recovery milestones, generate and send (e.g., wirelessly transmit) recommendations, such as instructions to display to a patient or HCP and/or a control program or adjustments thereto for (e.g., patient specific) operation of controllable device 25256, etc.

Sensing system(s), hub(s), and/or controllable device(s) may be wired or wireless. Wireless sensing systems may communicate wirelessly with one or more other devices, such as one or more other sensing systems, controllable devices, and/or hubs.

As discussed in various examples herein, sensing system (s), hub(s), and/or controllable device(s) may perform one or more of the following operations in one or more procedures/methods that may be executed by one or more processors: take samples/measurements of patient biomarkers, process samples, generate information, transmit information, receive information, analyze information, generate thresholds, execute a patient model to generate predictions, generate recommendations, transmit recommendations, receive recommendations, display recommendations (e.g., to an HCP), select or control pre-, in-, and/or post-surgery device settings, etc.

The example scenario shown in FIG. 13 is one of many possible examples. In various implementations, there may be more or fewer sensing systems, controllable devices, and/or controllers. Although patient 25252 is shown in bed 25259, patient may be in other positions and environments (e.g., seated, standing, walking or otherwise mobile at home, in vehicle) at various times relative to surgery (e.g., pre-, in-and/or post-surgery). For example, patient 25252 may be immobile or mobile in a healthcare facility (e.g., near hub 25258) or away from a healthcare facility (e.g., away from hub 25258), as described in FIGS. 2B and 2C herein. A mobile patient may have one or more mobile devices (e.g., mobile device 25260), one of more sensing systems (e.g., as shown in FIG. 13 as 25253, 25254, 25255) each configured to communicate with the computing device (e.g., a hub or a surgical hub) 25258 (e.g., if hub 25258 is located remote from a mobile patient). For example, a mobile patient may have/carry a mobile device, such as a mobile phone, a wearable sensing system, a controllable device (e.g., controllable device 25256) and/or other device that may be configured with a patient monitoring application executed by a processor in the mobile device. In some examples, mobile device 25260 and a sensing system (e.g., third sensing system 25255) may be incorporated into a device, such as a watch with cellular phone capabilities and sensing system capabilities. The mobile device (e.g., running the patient monitoring application) may be configured to perform one or more of the following: receive and process patient biomarker measurements, determine patient biomarker measurement thresholds, generate and/or receive predictions regarding potential complications, generate, receive, display and/or apply notifications and/or recommendations to a patient and/or controllable device(s), and/or the like. For example, patient 25252 may carry a mobile phone configured (e.g., by executing a patient monitoring application) to receive patient biomarker measurements from first, second and third sensing systems 25253, 25254, 25255, receive predicted complications to monitor patient for, receive patient monitoring thresholds for recovery milestones and/or complications from the computing device 25258, analyze patient biomarker measurements relative to the received thresholds for received complications, send a notification with the patient biomarker measurements to the computing device 25258 if a threshold is reached (e.g., through a wireless telecommunications system and the internet), and receive from the computing device 25258 recommendations, such as instructions to display to a patient and/or a control program or adjustments thereto for operation of controllable device 25256.

In an example, a threshold associated with a patient biomarker may be determined. In some examples, a surgical hub (e.g., and/or a (wearable) sensing system) may include/comprise a processor configured to determine a first threshold associated with a first patient biomarker and/or a second threshold associated with a second patient biomarker. The first threshold and/or the second threshold may be determined, for example, based (e.g., at least) on baseline data associated with a patient. In an example, measurement data associated with a patient biomarker may be received or obtained. For example, the surgical hub (e.g., and/or a (wearable) sensing system) may receive, obtain, or utilize (e.g., from at least one sensing system) a first measurement data associated with the first patient biomarker and a second measurement data associated with the second patient biomarker. In an example, an occurrence of a thoracic post-surgical complication may be detected or predicted. For example, the surgical hub (e.g., and/or a (wearable) sensing system) may detect an occurrence of a thoracic post-surgical complication, for example, by comparing the first measurement data with the first threshold and the second measurement data with the second threshold. A notification (e.g., a real-time notification) may be generated and/or sent to a patient and/or an HCP. For example, the surgical hub (e.g., and/or a (wearable) sensing system) may generate a notification (e.g., a real-time notification) indicating the occurrence of the thoracic post-surgical complication if/when at least one of the first measurement data crosses the first threshold (e.g., for a predetermined amount of time) or the second measurement data crosses the second threshold (e.g., for a predetermined amount of time). The surgical hub (e.g. and/or a (wearable) sensing system) may generate an actionable notification associated with the occurrence of the thoracic post-surgical complication. The surgical hub (e.g., and/or a (wearable) sensing system) may send the notification (e.g., a real-time notification) and/or the actionable notification associated with the occurrence of the thoracic post-surgical complication to the patient or an HCP.

In some examples, a third threshold associated with a third patient biomarker may be determined or obtained. For example, a surgical hub (e.g., and/or a (wearable) sensing system) may be configured to receive or obtain a third measurement data associated with the third patient biomarker. The occurrence of the thoracic post-surgical complication may be (e.g., further) detected or predicted, for example, by comparing the third measurement data with the third threshold. The notification (e.g., a real-time notification) may be generated, for example, if/when at least one of the first measurement data crosses the first threshold (e.g., for a predetermined amount of time), the second measurement data crosses the second threshold (e.g., for a predetermined amount of time), or the third measurement data crosses the third threshold (e.g., for a predetermined amount of time).

In some examples, a patient biomarker (e.g., the first patient biomarker, the second patient biomarker, or the third patient biomarker) may be, for example, VO2 Max, a respiration rate, a heart rate variability, a physical reaction, a diaphragmatic muscle tone, or an oxygen saturation, as described herein. In some examples, a threshold (e.g., to generate a notification, perform an analysis, make a determination, identify a complication, and/or the like) for a patient biomarker (e.g., the first patient biomarker, the second patient biomarker, or the third patient biomarker)

may be determined based on, for example, one or more of VO2 Max, a respiration rate, a heart rate variability, a physical reaction, a diaphragmatic muscle tone, or oxygen saturation.

Monitoring (e.g., post thoracic surgery monitoring) of patient biomarkers may indicate (e.g., potential or actual thoracic post-surgical) complications, such as, for example, one or more of the following: PAL, a lung collapse (e.g., pneumothorax), pulmonary insufficiency (e.g., limited lung volume), irregular respiration, infection, arrhythmias, residual intrapleural air spaces, postpneumonectomy empyema, bronchopleural fistula, cardiac herniation, lobar gangrene, esophagopleural fistula and/or healing cascade milestones.

A PAL may be monitored and detected, for example, by measuring at least one of the following: an air volume, a respiratory rate, a phase of respiration, and/or the like. In some examples, an analysis of patient biomarker measurement values to one or more thresholds (e.g., via an algorithm, comparison and/or the like) and/or a determination relating thereto may be based on (e.g., may account for) patient-specific data/information, such as a surgical procedure (e.g., lung volume reduction), medication, time period after surgery, etc. For example, one or more thresholds involved in an analysis and/or determination may be adjusted based on patient-specific information, such as pre-surgery, in-surgery, and/or post-surgery generated data/information.

A lung collapse or pneumothorax may be monitored and detected, for example, if/when air leaks into space (e.g., pleural space) between a lung and a chest wall. The air may push on the outside of the lung, which may result in a lung collapse. A pneumothorax may be a complete lung collapse or a partial collapse of a portion of a lung. Pneumothorax may be indicated or detected, for example, by (e.g., common) signs of chest pain, and/or by monitoring one or more patient biomarkers, such as oxygen saturation, blood pressure reduction, and/or heart rate increase. For example, a thoracic post-surgical complication such as a lung collapse or pneumothorax may be predicted or detected based on one or more patient biomarkers reaching one or more (e.g., patient specific) threshold values. A patient biomarker (e.g., first, second and third patient biomarkers) may be, for example, a rate of change in a patient's Oxygen saturation, a rate of change in patient's blood pressure, or a rate of change in patient's heart rate.

Avoidance of a PAL complication may be balanced with avoidance a pneumothorax complication. An increase in suction may (e.g., be used to) remove a building pneumothorax. A leak (e.g., a PAL) may be worsened, for example, by an increase in suction in the pleural space (e.g., to prevent pneumothorax). Reduced suction may reduce stress on a lung (e.g., reduce inducement of a leak), but may allow air buildup (e.g., increasing the likelihood of pneumothorax), where severity may depend on a leak volume or rate.

Referring to the example shown in FIG. 13, a balance between avoiding a PAL and pneumothorax may be implemented, for example, by controlling suction in chest tube 25257. Flow or air volume (e.g., over a time period) in chest tube 25257 may be measured, for example, to determine negative pressure being applied to chest tube 25257. For example, a digital system (e.g., controllable device 25256) may (e.g., be used to) measure the air flow or air volume over a time period. Chest tube flow or air volume may be provided, for example, by a flow meter in line with chest tube 25257 (e.g., inside controllable device 25256). A balance may be achieved between suction of air and a leak rate or leak volume. Leak severity may be assessed (e.g., analyzed, detected), for example, by monitoring (e.g., analyzing or coupling) air flow or air volume (e.g., over a time period) in chest tube 25257 with one or more patient biomarkers, such as respiratory rate and a phase of respiration. Suction may be modulated, for example, based on a detected respiratory phase. Respiration phases may include inhaling and exhaling. Respiratory phases may be determined, for example, by monitoring diaphragmatic muscle tone. Diaphragmatic muscle tone may be monitored, for example, by a respiratory muscle mechanomyogram (MMG) generated by mechanomyography, e.g., to non-invasively assess mechanical activation of inspiratory muscles of a lower chest wall, and/or by electromyographic (EMG) monitoring. MMG and EMG may be measured, for example, using skin patches or a tocodynamometer-like belt (e.g., 25254 of FIG. 13).

An infection may be monitored and detected, for example, by monitoring at least one of the following patient biomarkers: core body temperature, heart rate, heart rate variability, sweat rate, coughing, bacteria in respiratory tract, peripheral temperature, circadian rhythm, and/or bacterial load in the lungs, as described herein. An arrhythmia is a problem with the rate or rhythm of heartbeat (e.g., heart beats too quickly, too slowly, and/or with an irregular pattern). In an example of heart rate and variability, an irregular heart function may indicate a reduced blood supply to the body, which may slow recovery.

A baseline may be established for each of one or more patient biomarkers. For example, a patient may wear one or more sensing devices with one or more sensors (e.g., first, second and/or third sensing systems 25253, 25254, 25255 shown in FIG. 13) pre-, in-, and/or post-surgery to measure one or more patient biomarkers (e.g., VO2 max, respiration rate, heart rate variability, physical reaction(s) such as coughing and/or sneezing, oxygen saturation). In some examples, pre-surgery patient biomarker monitoring may (e.g., be used to) establish a baseline for one or more patient biomarkers (e.g., for VO2 max, respiration rate, heart rate variability, physical reaction(s) such as coughing and/or sneezing, oxygen saturation). A baseline for one or more patient biomarker values may be compared to (e.g., real time) measured values (e.g., for VO2 max, respiration rate, heart rate variability, physical reaction(s) such as coughing and/or sneezing, oxygen saturation), for example, to monitor patient biomarkers in-surgery and post-surgery (e.g., during recovery). A threshold value may be obtained based on a baseline value associated with a patient biomarker. Comparison of measured patient biomarker values to baseline values and/or to threshold values (e.g., absolute value of measured value exceeds a threshold value) and/or comparison of derived metrics (e.g., difference/change between measured value and baseline value, normalized value, etc.) to a threshold value may (e.g., be used to) monitor a patient (e.g., detect one or more patient states), such as, for example, whether the patient reached one or more recovery milestones, whether the patient may be developing or has developed one or more complications, and/or other states (e.g., anxiety, physical activity, and/or other physiologic actions). One or more alarms and/or notifications may be based on (e.g., triggered by) one or more detected patient states.

Measurement data/information may be obtained or collected from one or more sensing systems. A sensing system may include, for example, an environmental sensing system (e.g., a surgical sensing system with surgical sensors that generate sensor data during surgery on a patient), a patient sensing system, a personal sensing system, etc. For example, a surgical device/instrument (e.g., a surgical stapler, energy device) may have one or more environmental and/or personal/patient sensing systems with one or more sensors and/or one or more surgical device settings, which may be (e.g., automatically and/or manually) selected, for example, based on sensed data, processed data, feedback, recommendations, etc. A surgical device/instrument may be utilized in one or more surgical tasks, surgical procedures, and/or impending surgical actions. A surgical device/instrument may contextualize data associated with a surgical event, for example, to receive or generate a context action. A (e.g., personal) sensing system may include one or more wearable sensing systems (e.g., patient wearable sensing systems or patient sensing systems). A wearable sensing system may include, for example, a patient wearable sensing system, a health care professional (HCP) wearable sensing system, etc. A wearable sensing system may include one or more wearable devices. A wearable device may include one or more sensors and/or one or more sensing systems. A (e.g., patient) wearable sensing system may include one or more sensors. A patient wearable sensing system or one or more sensors (e.g., embedded) in a patient wearable sensing system may be used to measure one or more parameters (e.g., vital signs). Measured/measurement data may include, for example, pre-surgical measurement data, in-surgical measurement data, and/or post-surgical measurement data. Measured/measurement data may be, for example, raw data.

Measured/measurement data may be processed and/or transformed, for example, into (e.g., to determine) one or more patient biomarkers. An analysis may be performed, for example, using one or more patient biomarkers and/or measured/measurement data. Measurement data/information and/or patient biomarkers (e.g., detected or determined before, during, and/or after a surgical procedure) may be used to establish one or more thresholds for one or more patient biomarkers (e.g., to perform one or more analyses, make one or more determinations and/or recommendations). A patient biomarker is a measurable biological characteristic. A patient biomarker may be indicative of a physiologic property or a biologic state. A patient biomarker may be determined based on one or more other patient biomarkers. A biomarker may include, for example, a patient biomarker, a health care professional (HCP) biomarker, etc. A biomarker may include, for example, one or more values with or without metadata. Patient biomarker values may vary (e.g., over time, such as before, during, and/or after a surgical procedure). Patient biomarkers may include, for example, one or more of the following: a maximum amount of oxygen a person can utilize or consume (e.g., during exercise) (VO2 Max), respiration rate, heart rate variability, physical reaction (coughing and sneezing), and oxygen saturation, electroencephalogram (EEG), electrocardiogram (ECG or EKG), rapid eye movement sleep (REM sleep or REMS), gastrointestinal (GI) motility, etc.

A threshold value associated with a patient biomarker may be based on (e.g., established and/or adjusted), for example, one or more of the following: patient characteristics, a time of day, a time relative to surgery, an environment, biomarker measurements before, during, and/or after surgery, surgical details, baseline values etc. A device or sensing system may determine or receive one or more thresholds (e.g., from a hub). A hub may be used interchangeably with a computing system as described herein. A hub may include a surgical-related computing system. A hub or a surgical hub may include, for example, one or more of the following: a computing device, a server (e.g., a cloud server), a tablet, a smartphone, etc. A sensing system or a wearable sensing system may (e.g., selectively or routinely, such as periodically) process sensed/measured data (e.g., to generate one or more biomarkers), perform an analysis of sensed data and/or one or more biomarkers (e.g., based on one or more thresholds), and/or send/transmit (e.g., to a hub) sensed data, one or more biomarkers, and/or information (e.g., results, determinations) based on one or more analyses.

One or more thresholds may be processed, for example, based on (e.g., created relative to and/or used against) one or more baseline records. For example, threshold processing (e.g., creation and/or use) may account for surgical information (e.g., the amount of lung volume reduction in surgery) that may result in an adjustment to a pre-surgical baseline. A measured biomarker value may be compared with a threshold value associated with a patient biomarker (e.g., based on an adjusted baseline) to determine recovery milestones, for example, to track healing progress and/or indication(s) of one or more complications. A baseline value for a biomarker may be created (e.g., and/or adjusted), for example, before, during and/or after surgery.

Figure 14:
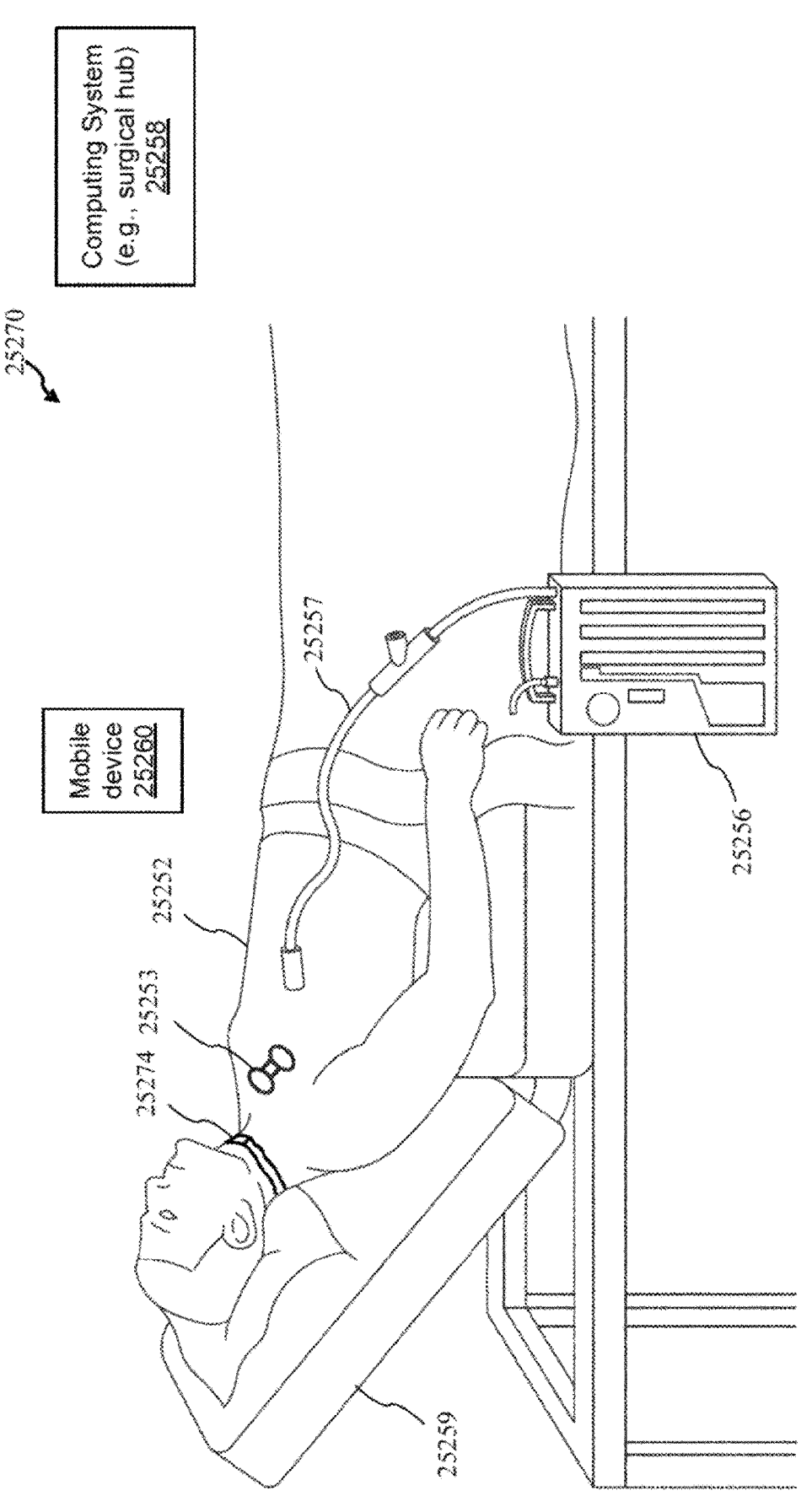
FIG. 14 shows an example of a patient wearing a patient wearable sensing system for detecting esophageal motion, in accordance with at least one aspect of the present disclosure.

A patient biomarker may be monitored by a sensing system. The sensing system may be a patient wearable sensing system. The sensing system may be communicatively coupled with a computing device or a hub or a surgical hub. In an example, a sensing system (e.g., as shown in FIGS. 13 and 14) may comprise one or more processors configured (e.g., by executing instructions in an executable program) to (e.g., at least) perform a method to receive (e.g., from a hub or a surgical hub), a first threshold associated with a first patient biomarker and/or a second threshold associated with a second patient biomarker. In an example, a post-surgical complication may be detected or predicted based on measurement data associated with the one or more of a set of patient biomarkers crossing respective threshold value(s). For example, a sensing system (e.g., via the one or more processors executing instructions) may be configured to receive a request for detecting a post-surgical complication based on at least one of a first measurement data associated with the first patient biomarker crossing a first threshold and/or a second measurement data associated with the second patient biomarker crossing a second threshold (e.g., for a predetermined amount of time). The sensing system (e.g., via the one or more processors executing instructions) may be configured to measure the first measurement data associated with the first patient biomarker and the second measurement data associated with the second patient biomarker. The sensing system (e.g., via the one or more processors executing instructions) may be configured to monitor the first measurement data and the second measurement data (e.g., in real-time), for example, by comparing each of the first measurement data and the second measurement data with the first threshold and the second threshold, respectively. The sensing system (e.g., via the one or more processors executing instructions) may be configured to generate a notification (e.g., real-time notification) indicating an occurrence of the post-surgical complication, for example, if/when the first measurement data crosses the first threshold, and/or if/when the second measurement data crosses the second threshold (e.g., for a predetermined amount of time). The sensing system (e.g., via the one or more processors executing instructions) may be configured to send the notification (e.g., to the surgical hub) indicating the occurrence of the post-surgical complication.

In some examples, the sensing system (e.g., via the one or more processors executing instructions) may be configured to determine a severity level associated with the thoracic post-surgical complication. In an example, the severity level may be determined based on a measurement data. A notification type associated with a notification (e.g., a real-time notification) may be determined based on the severity level. The sensing system (e.g., via the one or more processors executing instructions) may send the real-time notification and/or the severity level, for example, to a display unit for displaying to a patient, an HCP, etc. In an example, in some examples, the sensing system (e.g., via the one or more processors executing instructions) may be configured to send the notification and the severity level to a display unit for displaying to a patient if the severity level is low, and a display unit for displaying to an HCP if the severity level is high.

In various examples, the post-surgical complication may be any type of complication, such as a PAL. The first patient biomarker or the second patient biomarker may be any biomarker, such as one of the following: a blood lactate, a sweat lactate, an indication of GI motility, a heart rate variability, a blood pH value, a sweat pH value, etc.

A threshold (e.g., the first threshold or the second threshold) may be adjusted based on a context. For example, the sensing system (e.g., via the one or more processors executing instructions) may be configured to determine a context based at least on: a surgery recovery timeline, a set of situational attributes, or a set of environmental attributes or environmental aspects as described herein. An environment may be, for example, a controlled environment or an uncontrolled environment. The set of situational attributes may comprise, for example, a physical mobility state, a sleeping state, etc.

Patient biomarkers may be monitored pre-, in- and/or post-surgery. Post-surgery patient biomarker values may be monitored, for example, based on post-surgery data/information obtained/received from one or more sensors (e.g., in one or more sensing systems). Post-surgery measurement data/information (e.g., from sensors embedded in wearable sensing systems) may be collected (e.g., received, processed, and/or analyzed) to monitor or track one or more patient biomarkers. Data/information from one or more sensors may be measured, for example, instantaneously and/or tracked over a period of time. Post-surgery measurement data/information from the sensors may be measured or tracked in a controlled environment, for example, under supervision and/or at a location of an HCP, for example, as described in FIG. 2B herein. Post-surgery measurement data/information (e.g., from sensors) may be measured or tracked, for example, in an uncontrolled environment, such as a patient's (e.g., fixed or variable) location (e.g., house, vehicle, store) and/or while performing one or more (e.g., daily routine) tasks, such as eating, sleeping, walking, exercising, etc. as described in FIG. 2C herein.

Post-surgery measurement data/information from one or more sensors associated with a patient biomarker may be compared with respective threshold values associated with the patient biomarker. Post-surgery measurement data/information values achieving (e.g., equaling or exceeding) the (e.g., minimum) one or more thresholds within a time period (e.g., a predetermined time period) may indicate a progression to recovery. A failure to achieve one or more (e.g., established or defined) thresholds within a time period may indicate a slower recovery and/or one or more complications. One or more (e.g., relevant) healthcare providers (HCPs) may be notified about a failure to achieve one or more thresholds. Information and/or data provided (e.g., using one or more notifications) may enable (e.g., treatment) planning (e.g., by an HCP). For example, an HCP may plan alternative exploration and/or mitigation of a situation indicated by measurement data/information.

One or more recovery metrics may be tracked, for example, based on monitored post-surgical patient biomarkers. Complication development or progression (e.g., an advancing, stagnant or receding complication) may be tracked. For example, an esophageal stricture and/or other complications (e.g., non-lung complication(s)) may be tracked (e.g., after an esophageal surgical procedure). Post-surgical monitoring may be performed (e.g., implemented) using one or more sensing systems (e.g., each with one or more sensors) to track various recovery milestones and/or complications. In some examples, recovery milestones may be used to detect the possibility (e.g., likelihood) of complications arising, developing, progressing, receding, and/or the like. Complications may include, for example, esophageal leakage or esophageal stricture.

FIG. 14 shows an example of a sensing system 25270 to predict or detect complications, such as esophageal leakage or esophageal stricture. FIG. 14 shows an example of a patient wearable sensing system for detecting esophageal motion, in accordance with at least one aspect of the present disclosure. Patient monitoring system 25271 may include (e.g., as shown by example in FIG. 14) first wearable sensing system 25253, fourth wearable sensing system 25274, controllable device 25256, and hub 25258.

FIG. 14, compared to FIG. 13, shows an additional and/or alternative sensing system, monitored patient biomarkers, and complication prediction or detection. To avoid repetition, discussion of FIG. 13 may be incorporated into discussion of FIG. 14 and vice versa. Post-surgery data/information may be collected by monitoring one or more (e.g., wearable) sensors for one or more patient biomarkers. Fourth wearable sensing system 25274 may monitor one or more patient biomarkers, whose measurements may be used to determine esophageal motion, which may (e.g., in turn) be used to detect one or more complications, such as esophageal leakage and/or an esophageal stricture. Muscle function and mechanics may be monitored/tracked (e.g., non-invasively), for example, by measuring vibrations produced in skeletal muscles, which may be referred to as mechanomyography. Mechanomyography may be implemented in one or more (e.g., wearable) sensors (e.g., a sensor array). Esophageal motion may be monitored, for example, by one or more sensors (e.g., in one or more devices) worn by a patient (e.g., on or near a patient's neck).

Fourth wearable sensing system 25274 may be worn, for example, around a patient's neck. Fourth wearable sensing system 25274 may monitor esophageal motion, for example, by performing mechanomyography on patient 25252. In some examples, first wearable sensing system 25253 may monitor one or more patient biomarkers that support detection of one or more complications, such as esophageal leakage or an esophageal stricture.

Data/information sensed and generated by first and/or fourth sensing systems 25253, 25274 may be tracked over a period of time, e.g., for hours or days during a post-surgical period of time. Data/information may (e.g., be used to) track esophageal stricture and/or other non-lung complications (e.g., infection, esophagopleural fistula). Abnormal waveforms of muscle motion (e.g., esophageal motion), which may be determined during analysis of one or more measured patient biomarkers, may indicate, for example, development of a stricture (e.g., during a healing process following surgery). Information/measurement data (e.g., collected from one or more wearable sensors, such as first and/or fourth sensing systems 25253, 25274) may be used (e.g., analyzed) to determine, for example, whether additional surgery may be required, whether to change the viscosity of food, whether to change or add to physical therapy and/or occupational therapy, etc. No action or one or more actions may be recommended (e.g., and taken automatically and/or manually), for example, based on one or more determinations resulting from one or more analyses of patient monitoring data/information provided by, for example, first and/or fourth sensing systems 25253, 25274. One or more notifications (e.g., real-time notifications) may be generated and/or sent (e.g., to an HCP, patient, and/or controllable device(s)), for example, based on one or more recommendations.

In some examples, hub 25258 may be configured to perform one or more of the following: receive and process patient biomarker measurement data from one or more sensing systems (e.g., first and/or fourth sensing systems 25253, 25274), determine patient biomarker measurement thresholds, generate (e.g., patient-specific) predictions regarding potential complications, generate and/or transmit notifications and/or recommendations for displaying to a patient and/or to controllable device 25256 to operate controllable device(s), and/or the like. For example, hub 25258 may receive patient biomarker measurement data from first and/or fourth sensing systems 25253, 25274, generate predicted complications to monitor patient for, determine patient monitoring thresholds for recovery milestones and/or complications, analyze patient biomarker measurements relative to the thresholds for the predicted complications and/or recovery milestones, generate and send (e.g., wirelessly transmit) recommendations, such as instructions to display to a patient or HCP and/or a control program or adjustments thereto for (e.g., patient specific) operation of a controllable device, etc.

In some examples, a patient biomarker monitoring/analysis system may be configured to communicably couple to a surgical hub. The surgical hub may be configured to communicably couple to one or more in-surgery and/or post-surgery (e.g., recovery) devices that may provide (e.g., display) one or more actionable notifications (e.g., to a patient and/or HCP). A patient biomarker monitoring/analysis system may comprise, for example: a processor and a memory coupled to the processor. The memory may store instructions that, when executed by the processor, cause the patient biomarker monitoring/analysis system to perform a method or procedure (e.g., as follows). A patient biomarker monitoring/analysis system may receive data/information indicative of one or more actions (e.g., recommendable actions). For example, the data/information may include one or more actions that may be taken after a surgical procedure (e.g., available actions may be based on general and/or specific details of one or more surgical procedures implemented on a patient). The patient biomarker monitoring/analysis system may receive patient biomarker data/information associated with the patient. The patient biomarker monitoring/analysis system may analyze the available or known actions and the patient's biomarker monitoring data/information to determine which action(s) may be optimal or suboptimal for the patient (e.g., to reduce the likelihood or impact of and/or avoid one or more potential complications). The patient biomarker monitoring/analysis system may generate an actionable notification indicating one or more selected actions (e.g., procedural steps, such as one or more exercises). The patient biomarker monitoring/analysis system may transmit the one or more selected actions, for example, to one or more devices that may provide to a patient and/or HCP (e.g., display at text, play as audio and/or video instruction).

A notification (e.g., an actionable notification) may be reported, for example, in real-time (e.g., real-time reporting). A notification (e.g., an actionable notification) may indicate, for example, a thoracic post-surgery complication or the achievement of a thoracic post-surgery milestone. Reports may be generated, provided, and/or received (e.g., by an HCP) periodically (e.g., hourly, daily, weekly) and/or aperiodically (e.g., ad hoc, on demand by sender and/or recipient, based on emergency or threshold detection, and/or the like). A report may include, for example, one or more values for one or more patient biomarkers, one or more results of one or more analyses performed based on one or more patient biomarker values, thresholds, baselines, etc., one or more threshold values, one or more baseline values, etc. A report may include, for example, data associated with an indication, such as data indicating that a thoracic post-surgery complication has been detected. A report may include, for example, data associated with therapy tracking, e.g., indicating patient therapy, whether a patient is performing therapy, the frequency of performance, whether the therapy is being performed correctly, etc.

An actionable notification may be selected or changed, modified or updated from a default or existing action (e.g., based on monitoring and/or analyses of one or more patient biomarkers), for example, to enable a patient or an HCP to perform at least one recommended action. The type of actionable notification may depend on the patient biomarker measurement(s) and/or processing (e.g., based on baseline value(s), types of notifications available). An actionable notification may include, for example, patient exercises.

An actionable severity level associated with the detected post-surgical thoracic complication may be determined. For example, the hub or the computing device or system may determine an actionable severity level associated with a detected or predicted PAL. A notification may be sent to the patient and/or the HCP indicating a potential thoracic post-surgical complication and the associated actionable severity level. The type and/or content of a notification may be determined based on the actionable severity level. For example, when the detected complication is determined to be associated with low-risk actionable severity level, the computing device or system or the hub may generate a real-time notification to a device associated with the patient. When the detected complication is determined to be associated with high-risk actionable severity level, the computing device or system may generate a real-time notification to a device associated with the patient and a device associated with an HCP. In an example, when the detected complication is determined to be associated with low-risk actionable severity level, the computing system may generate a real-time notification indicating the medical name of the complication and of the patient biomarker that crossed the corresponding threshold(s). When the predicted or detected complication is determined to be associated with high-risk actionable severity level, the computing system may generate a real-time notification indicating a recommended course of action.

In some examples, an actionable notification may be associated with the occurrence of a thoracic post-surgical complication. An actionable notification may be selected or otherwise determined, for example, to assist a patient and/or an HCP with efforts to reduce or avoid one or more post-surgical complications. An actionable notification may, for example, support (e.g., enable) a patient and/or an HCP to perform at least one recommended action. For example, a recommended action may include (e.g., provide, such as for display) steps for performing one or more deep breathing exercises.

In some examples, a patent's inhale and exhale patterns may be monitored, for example, while performing a deep breathing exercise following a lung procedure. The deep breathing exercise may reduce the risk of pneumonia. A patient may be guided to perform a deep breathing exercise, for example, by monitoring chest wall motion. For example, a patient may perform a breathing exercise by inhaling and holding his/her breath for 3-5 seconds, repeating the exercise multiple times (e.g., 10-15 repetitions). A patient may be prompted to perform an exercise (e.g., periodically, at set intervals, such as once per hour. Patient compliance may be tracked, for example, by monitoring patient biomarkers.

Patient progress and compliance with post-operative protocols may be indicated to hospital caretakers, for example, by tracking the number, frequency, and duration of walks (e.g., and associated cardio and/or respiratory metrics).

Patient biomarkers may correlate to physiological states of a patient. Patient biomarkers may correlate to complications. Patient biomarkers may correlate to recovery milestones. Patient biomarkers may correlate to (e.g., map to) other patient biomarkers. For example, a first patient biomarker may predict or indicate the existence or value of a second patient biomarker (e.g., and/vice versa). Patient biomarkers may correlate to surgical procedures on one or more organs or tissues. For example, relevant patient biomarkers may be different in various portions of a surgical procedure.

Figure 15:
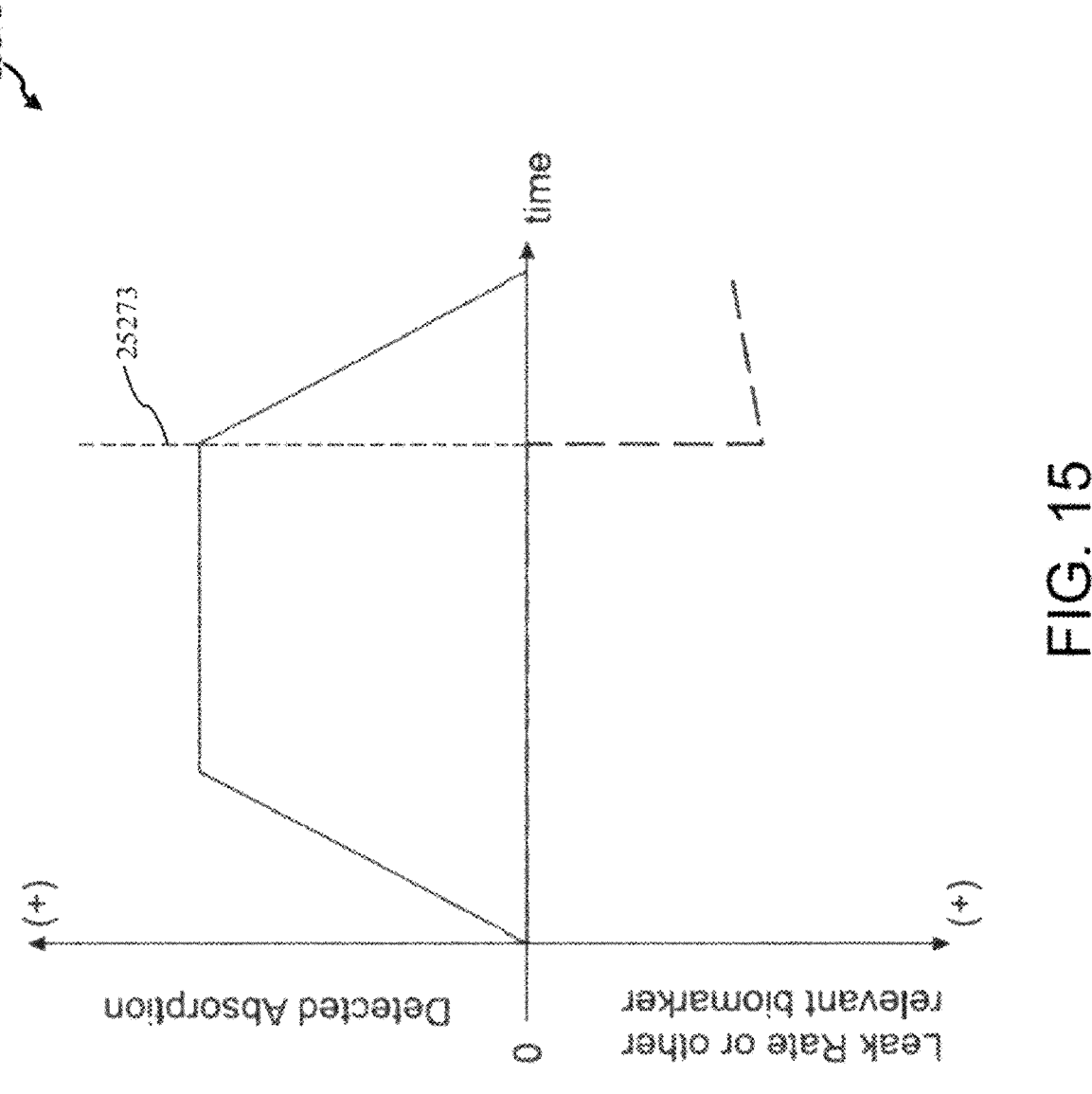
FIG. 15 shows an example relationship between a patient biomarker for bioabsorbable material with a patient biomarker indicative of healing.

FIG. 15 illustrates an example of a link between a patient biomarker for a bioabsorbable material and a patient biomarker indicative of healing. FIG. 15 shows an example of tracking changes in one or more patient biomarkers and identifying a link, e.g., by comparing tracked changes. A prediction may be based on a link or relationship (e.g., a link may support a prediction). For example (e.g., with respect to a prediction of recovery and/or complication), detection of a first patient biomarker may indicate the presence of a second patient biomarker and/or vice versa. In some examples, one or more patient biomarkers for bioabsorbable material may be linked with one or more patient biomarkers indicative of healing. The rate of detected absorption of a bioabsorbable material may provide an indication of an air leak rate or other relevant patient biomarker. For example, the rate of absorption of a bioabsorbable material (e.g., tracked by one or more patient biomarkers) may increase, remain the same and/or decrease or degrade (e.g., slow down). Comparative graph 25272 shows a relationship between multiple patient biomarkers as an example of determining (e.g., by measuring) a first patient biomarker (e.g., a detected absorption or resorbing rate) and determining (e.g., by a link or relationship) a second patient biomarker (e.g., a leak rate or other relevant patient biomarker) and/or vice versa. In some examples, a sealant (e.g., to avoid a leak) may degrade before the occurrence of full or complete healing, which may impact a relationship. As shown by example in FIG. 15, a decreasing absorption rate of a bioabsorbable material may be an indication of slow healing and/or a complication (e.g., an increasing leak rate with a potential for a PAL). For example, as shown in FIG. 15 beginning at time 25273, the leak rate or other patient biomarker value may increase if/when the detected absorption rate decreases, or vice versa.

Surgical procedural operations (e.g., steps) may correlate to one or more (e.g., relevant) patient biomarkers (e.g., post-surgery patient biomarkers). For example, measurement data and/or information generated (e.g., received, collected, processed, and so on) from monitoring one or more (e.g., post-surgical) patient biomarkers may be correlated with one or more surgical procedural operations (e.g., thoracic surgical procedure steps). In an example, a (e.g., thoracic) surgical procedure may include a dissection of parenchyma, a transection of arteries and/or veins, a transection of parenchyma, and a dissection of lymph node. A correlation (e.g., a relationship mapping) may be established between each portion (e.g., each operation) of a (e.g., thoracic) surgical procedure (e.g., dissection of parenchyma, transection of arteries and/or veins, transection of parenchyma, and dissection of lymph node) with one or more corresponding (e.g., post-surgical) patient biomarkers.

Figure 16:
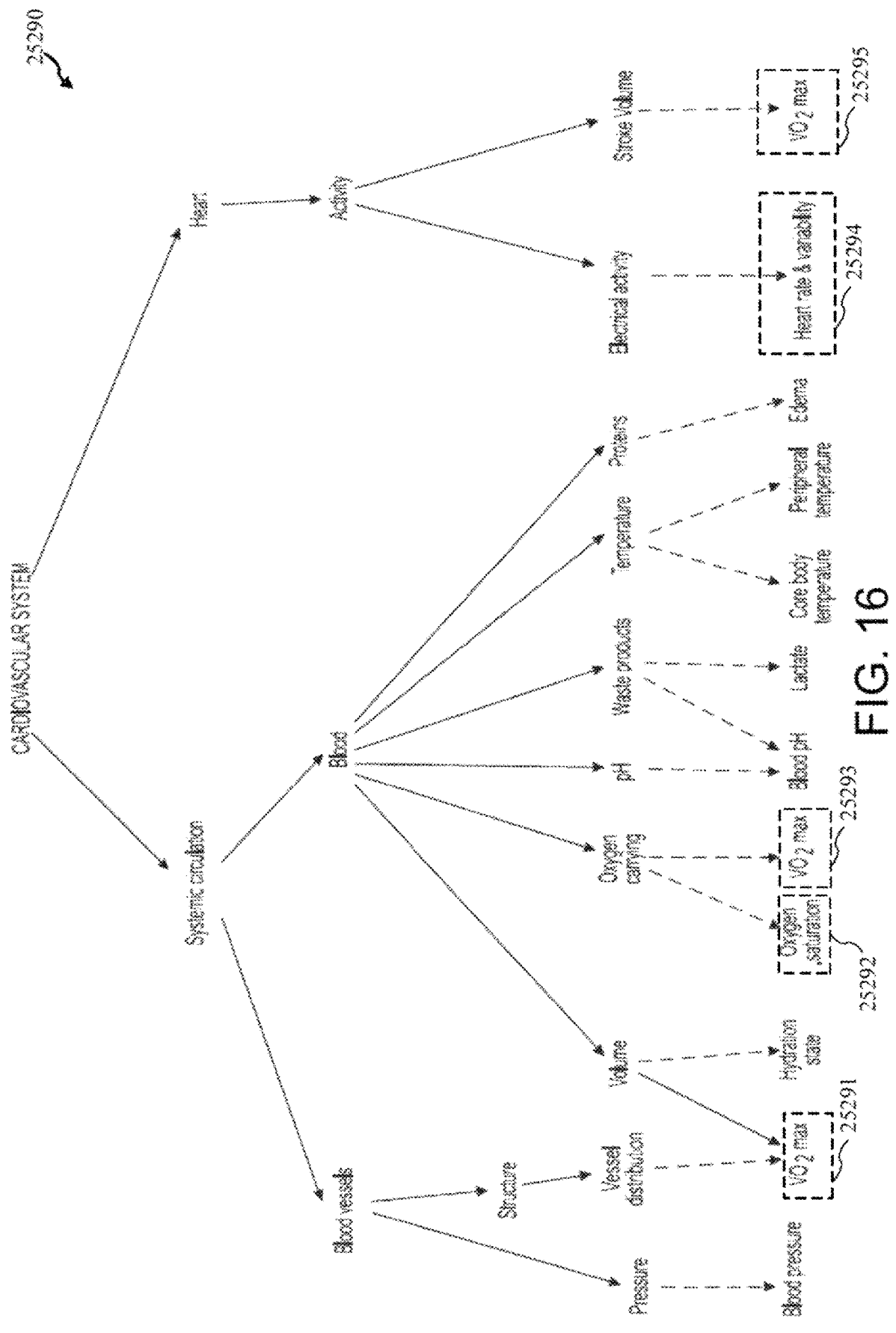
FIG. 16 illustrates example relationships between patient biomarkers relevant to the cardiovascular system that may be used to detect post-thoracic complications or milestones.
Figure 17:
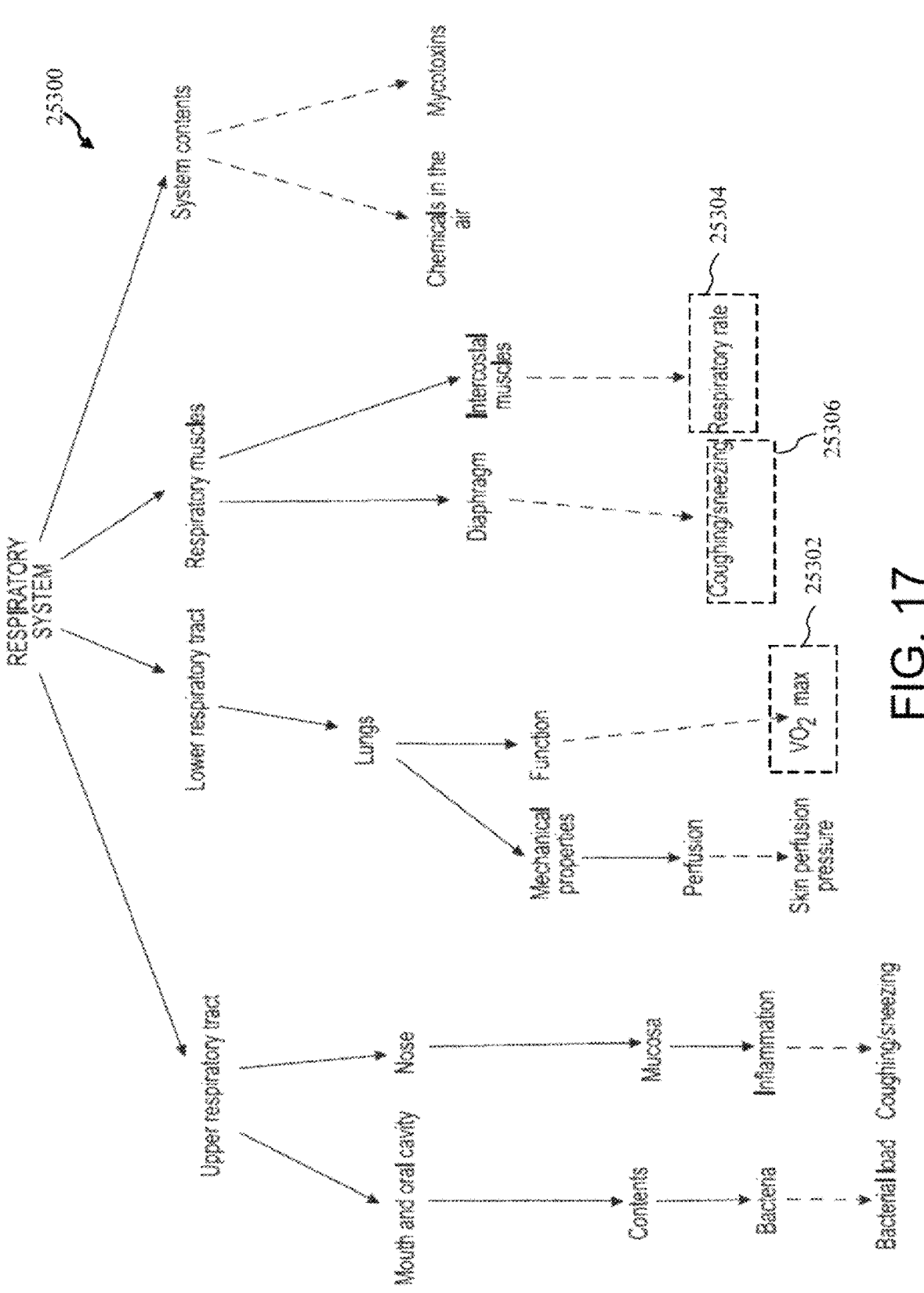
FIG. 17 illustrates example relationships between patient biomarkers relevant to the respiratory system that may be used to detect post-thoracic complications or milestones.

FIGS. 16 and 17 illustrate examples of relationships between patient biomarkers in the respiratory system and the cardiovascular system, respectively. FIG. 16 illustrates example relationships between patient biomarkers relevant to the cardiovascular system that may be used for detecting and/or predicting post-thoracic complications (e.g., prolonged air leaks) or milestones. In an example, one of more of the following patient biomarkers associated with the cardiovascular system 25290 may be measured. VO2 Max 25291, 25293, and 25295, heart rate variability (HRV) 25294, Oxygen saturation 25292 could be measured for detecting or predicting a complication (e.g., a prolonged air leak). As illustrated in FIG. 16, the VO2 Max 25295 may provide an indication of heart activity (e.g., stroke volume). VO2 Max 25291 may provide an indication of systemic circulation (e.g., blood volume and/or blood vessel distribution). VO2 Max 25293 may provide an indication of Oxygen carrying capacity of blood, HRV 25294 may provide an indication of heart activity (e.g., electrical heart activity). Oxygen saturation 25292 may provide an indication of Oxygen being carried in blood. As described herein, a combination of measurement data associated with these patient biomarkers may be used for detecting and/or predicting thoracic post-surgical complications (e.g., prolonged air leaks) and/or milestones by comparing the measurement data against the baseline records while accounting for the amount of lung volume reduction and compared against key recovery milestones to track healing progress or arising of complications.

FIG. 17 illustrates example relationships between patient biomarkers relevant to the respiratory system 25300. One or more patient biomarkers shown in FIG. 17 may be used to detect post-thoracic complications (e.g., prolonged air leaks) or recovery milestones, as described herein. In an example, one of more of the following patient biomarkers associated with the respiratory system 25300 may be measured. VO2 Max 25302, respiration rate 25304, physical reaction (coughing and sneezing) 25306 could be measured for detecting or predicting a complication (e.g., a prolonged air leak). As illustrated in FIG. 17, the VO2 Max 25302 may provide an indication of lung function related to the lower respiratory tract of the respiratory physiological system. Coughing/sneezing 25306 may indicate the state of respiratory muscles (e.g., the diaphragm). Respiratory rate 25304 may indicate the state of intercostal respiratory muscles of the respiratory physiological system. A combination of measurement data associated with these patient biomarkers may be used for detecting and/or predicting thoracic post-surgical complications (e.g., prolonged air leaks) and/or milestones by comparing the measurement data against the baseline records while accounting for the amount of lung volume reduction and compared against key recovery milestones to track healing progress or arising of complications.

In an example, thoracic post-surgical complications and/or milestones may be detected and/or predicted using measurement data associated with the patient biomarkers relevant to cardiovascular physiological system as shown in FIG. 16 and the patient biomarkers relevant to the respiratory physiological system as shown in FIG. 17.

FIG. 18 shows example correlation between relevant patient biomarkers and thoracic surgical procedural steps 25309. As illustrated in FIG. 18, a set of patient biomarkers may correlate to surgical procedures and/or a step thereof. For example, a parenchyma dissection step of a thoracic surgical procedure may be correlated with one or more (e.g., post-surgery) patient biomarkers, such as blood pressure. Surgical instruments associated with a parenchyma dissection step of a thoracic surgical procedure may include, for example, one or more of the following: a monopolar bovie, a harmonic scalpel, and/or an advanced bipolar radio frequency (RF) energy instrument. A step of a procedure may be associated with one or more outcomes (e.g., physiological states). An outcome related to a parenchyma dissection step of a thoracic surgical procedure may include, for example, hemostasis. The occurrence of hemostasis (e.g., due to dissection of parenchyma during a thoracic surgical procedure) may be monitored (e.g., and determined), for example, by measuring and/or monitoring a patient's blood pressure (e.g., in-surgery, during a post-surgical procedure, and/or during post-surgery monitoring).

A transection of arteries and/or veins step of a thoracic surgical procedure may be correlated with one or more (e.g., post-surgery) patient biomarkers, such as blood pressure, tissue perfusion pressure, edema, arterial stiffness, collagen content and/or thickness of connecting tissue. Surgical instruments associated with an artery and/or vein transection step of a thoracic surgical procedure may include, for example, one or more of the following: a harmonic scalpel, an advanced bipolar RF energy instrument, and/or a stapler. A thoracic surgical procedure step may be associated with one or more outcomes (e.g., physiological states). An outcome related to an artery and/or vein transection step of a thoracic surgical procedure may include, for example, hemostasis. The occurrence of hemostasis (e.g., due to transection of an artery and/or vein during a thoracic surgical procedure) may be monitored (e.g., and determined), for example, by measuring and/or monitoring blood pressure, tissue perfusion pressure, edema, arterial stiffness, collagen content, and/or thickness of connecting tissue (e.g., in-surgery, during a post-surgical procedure, and/or during post-surgery monitoring).

A parenchyma transection step of a thoracic surgical procedure may be correlated with one or more (e.g., post-surgery) patient biomarkers, such as pneumostasis, edema, lung tissue thickness, lung tissue viscoelastic properties, and/or lung tissue scarring and/or fibrous characterization. Surgical instruments associated with a parenchyma transection step of a thoracic surgical procedure may include, for example, a surgical stapler. A step of a thoracic surgical procedure may be associated with one or more outcomes (e.g., physiological states). An outcome related to a parenchyma transection step of a thoracic surgical procedure may include, for example, pneumostasis. The occurrence of pneumostasis (e.g., due to transection of parenchyma during a thoracic surgical procedure) may be monitored (e.g., and determined), for example, by measuring and/or monitoring edema, lung tissue thickness, lung tissue viscoelastic properties, and/or lung tissue scarring and/or fibrous characterization (e.g., in-surgery, during a post-surgical procedure, and/or during post-surgery monitoring).

A lymph node dissection step of a thoracic surgical procedure may be correlated with one or more (e.g., post-surgery) patient biomarkers, such as hemostasis and/or blood pressure. Surgical instruments associated with a lymph node dissection step of a thoracic surgical procedure may include, for example, one or more of the following: a monopolar bovie, a harmonic scalpel, and/or an advanced bipolar RF energy instrument. A step of a thoracic surgical procedure may be associated with one or more outcomes (e.g., physiological states). An outcome related to a lymph node dissection step of a thoracic surgical procedure may include, for example, hemostasis. The occurrence of hemostasis (e.g., due to dissection of a lymph node during a thoracic surgical procedure) may be monitored (e.g., and determined), for example, by measuring and/or monitoring blood pressure (e.g., in-surgery, during a post-surgical procedure, and/or during post-surgery monitoring).

One or more complications may develop from one or more portions of a surgical procedure, such as an issue with hemostasis or bleeding. For example, bronchial artery bleeding may occur. Bleeding may be reduced, for example, by pre-emptive clipping of a bronchial artery before bronchial dissection or lymph node dissection. Bronchial artery bleeding may be stopped, for example, by compression with a suction tip and/or by handling the vascular stump with energy devices or clips.

Bleeding may occur from large vessel stumps and bronchial stumps. Bronchial stump bleeding may occur from an accompanying bronchial artery, which may be clipped for hemostasis. Bleeding at a vascular stump may be reduced, for example, by compression for hemostasis, by using hemostatic materials, by stapling, by re-stapling, and/or by a suture.

Bleeding may occur from a lung parenchyma. Bleeding from a lung parenchyma may be reduced, for example, by coagulation hemostasis and/or suturing, e.g., for wounds with visible air leakage or an insufficient hemostatic effect of coagulation.

Bleeding may occur during (e.g., at the site of) lymph node dissection. Non-grasping en-bloc lymph node dissection may nourish vessels of a lymph node. Energy devices may be used for hemostasis (e.g., in combination with hemostatic materials), for example, if bleeding occurs at the site of lymph node dissection.

Bleeding may occur from chest wall incisions. One or more chest wall incisions may be made along the upper edge of one or more ribs. Hemostasis may be applied layer by layer. An incision may be re-checked for hemostasis before closing the chest.

Bleeding may occur at an internal chest wall. Bleeding at an internal chest wall may be managed, for example, with electrocoagulation. Diffuse capillary bleeding with an undefined bleeding site may be reduced, for example, by compression of the wound with gauze.

Pre-surgery monitoring, in-surgery monitoring, and/or post-surgery monitoring of patient biomarkers may (e.g., be used to) influence (e.g., select, adjust or change) surgical procedures, device settings, post-surgery procedures, exercises, medications, and/or the like. One or more (e.g., patient-specific or customized) recommendations may be based on (e.g., patient-specific) patient biomarker monitoring. For example, pre-surgery and/or in-surgery patient biomarker monitoring may influence surgery preparation/planning and/or operations implemented during a surgical procedure, such as surgical plans, what patient biomarkers to monitor, baselines, thresholds, device settings, choice of tools, post-surgical care, etc. Pre-surgery, in-surgery, and/or post-surgery patient biomarker monitoring may influence post-surgery. Measurement data and/or information gathered during pre-surgery, in-surgery and/or post-surgical monitoring of one or more patient biomarkers (e.g., hemostasis) may be used to determine or select what patient biomarkers to monitor, baselines, thresholds, device settings, post-surgical care, etc. For example, hemostasis issues may be predicted (e.g., based on pre-surgery and/or in-surgery patient biomarker monitoring) and/or hemostasis may not be achieved (e.g., in-surgery and/or during post-surgery).

A prediction of a complication, such as a hemostasis issue, based on pre-surgery monitoring and/or in-surgery monitoring of patient biomarkers, may lead to a determination pertaining to surgery planning and/or implementation. A determination may be based on monitored patient biomarkers and/or a prediction. A determination may provide a patient-specific or customized improvement, such as a determination to implement a tighter staple form, add reinforcement, and/or adjust an energy device algorithm, e.g., to improve the probability of reducing (e.g., post-transection) bleeding. For example, an analysis of data/information received from patient sensors for monitoring pre-surgical patient biomarkers may result in a prediction of a surgical complication, e.g., a complication resulting from hemostasis or bleeding. In some examples, the one or more patient biomarkers may be one or more (e.g., any combination) of blood pressure, blood pH, edema, heart rate, etc. An indication (e.g., a notification) of the prediction (e.g., with a probability of the likelihood of complication), such as for potential bleeding, oozing, or weeping from mobilization or transection may be provided (e.g., for automated and/or manual analysis and/or determination. In some examples (e.g., based on automated analysis and/or determination), a recommendation (e.g., compensation) may be indicated (e.g., displayed) for automated and/or manual implementation. For example, a recommendation or compensation may indicate one or more operations (e.g., operational changes) for device operation to compensate for a predicted complication based on one or more monitored patient biomarkers. In some examples, one or more adaptive energy devices may be automatically and/or manually adjusted for one or more recommended power levels, clamp pressures, impendence thresholds, energy modality, and/or termination conditions. For example, an adaptive stapler may be set (e.g., adjust or change) to one or more wait times, clamp pressures, creep thresholds, advancement rates, etc., to compensate for one or more predicted possibilities for one or more complications. In some examples, an indication (e.g., recommendation) may (e.g., also) be provided for one or more post-surgery (e.g., adjunct) therapies (e.g., to compensate for the likelihood of a predicted complication).

One or more (e.g., a set of) thresholds for patient biomarker monitoring (e.g., post-surgery monitoring thresholds) may be set, for example, based (e.g., at least) on (e.g., pre-surgery) patient biomarkers that may pertain to one or more complications, such as a prolonged air leak (PAL). A complication, such as a prolonged air leak (PAL), may occur, for example, after a pulmonary resection (e.g., pulmonary lobectomy). A prolonged PAL may increase the risk of one or more post-surgical complications. Patients may be monitored for a post-surgery PAL. Prediction modeling may (e.g., be utilized to) establish a post-surgery threshold setting to monitor one or more complications (e.g., a PAL). A post-surgery threshold setting may be established (e.g., selected, configured), for example, based on one or more data models and/or one or more patterns provided by the one or more data models. A post-surgery threshold setting to monitor (e.g., and detect) a PAL may be set, for example, to more than five (5) days of leakage postoperative day (POD). A post-surgery threshold setting to monitor (e.g., and detect) a PAL may be based on, for example, one or more pre-surgery patient biomarkers.

Pre-surgery patient monitoring may be used to predict (and attempt to reduce or avoid) in-surgery and/or post-surgery complications. Pre-surgical monitoring of patient physiologic parameters may support prediction (e.g., anticipation or identification) of potential tissue or physiologic issues (e.g., complications) that may be reduced or avoided, for example, by one or more surgical procedure or tool implementations (e.g., adjustments, such as modifications by changes, additions, and/or subtractions) to increase the probability of a more successful (e.g., complication-free) outcome. Pre-surgery patient biomarkers may include, for example, at least one of the following: VO2 Max, respiration rate, heart rate variability, physical reaction (coughing and sneezing), oxygen saturation, EEG, ECG or EKG, REM sleep (REMS), GI motility, blood sugar levels, hydration state, temperature, tissue perfusion pressure, etc.

VO2 Max may (e.g., be used to), for example, gauge general fitness, identify a risk of adverse cardiovascular events (e.g., complications) in-surgery and/or post-surgery, track recovery (e.g., post-surgical milestones), etc.

Respiration rate may (e.g., be used to) identify, for example, one or more complications, such as post-operative pain, an air leak (e.g., a PAL), a collapsed lung, lung inflammation, etc.

Heart rate variability (HRV) may (e.g., be used to) identify, for example, stress and/or blood supply rate (e.g., relative to a recovery rate). A wearable sensor (e.g., a watch, such as Apple Watch series 5) may monitor and report heart rate and/or heart rate variability. HRV may be determined (e.g., from an ECG), for example, as the time period variation (e.g., standard deviation) between R peaks in the QRS complex, known as R-R intervals.

A physical reaction (e.g., coughing and/or sneezing), may (e.g., be used to) identify, for example, one or more complications, such as respiratory tract infections, a collapsed lung, pulmonary edema, etc.

Oxygen saturation, may (e.g., be used to) gauge or identify, for example, lung functionality, recovery capacity, etc.

EEG, may (e.g., be used to) identify, for example, stress, anxiety, depression, sleep, confusion, delirium, and/or sepsis. An EEG headset with one or more sensors may measure electrical activity in the brain, which may be correlated with (e.g., used to infer) stress, anxiety, depression, confusion, delirium, and/or sepsis. Delirium/sepsis-associated encephalopathy (SAE) may indicate (e.g., post-surgery) sepsis. Delirium may be indicated by hyperactive brain activity and/or physical behavior (e.g., agitation, pulling out lines, hallucinating, etc.) and/or the hypoactive brain activity and/or physical behavior (e.g., sluggishness, drowsiness, inattention, etc.). Confusion and/or delirium may be measured, for example, by a frequency and/or severity of episodes. Confusion may be inferred from the location or movement of a patient, which may be tracked, for example, by a location monitor (e.g., GPS tracker). An unexpected location change or disruption to normal routine may indicate that the user is suffering from confusion or delirium. Delirium may be identified through characteristic brain patterns (e.g., slowing or dropout of the posterior dominant rhythm and loss of reactivity to eyes opening and closing).

A threshold for EEG measurements (e.g., sensed by a wearable EEG headset) may be, for example, increased triphasic waves (e.g., greater than three EEG grade using Synek 5-point scale).

ECG or EKG, may (e.g., be used to) identify, for example, heart rate, heart rate variability, stress or anxiety, sleep, etc. A wearable sensing system (e.g., a wristband, a watch, etc.) may monitor and report ECG.

Sleep (e.g., REM sleep (REMS)), may (e.g., be used to) identify, for example, the number of hours of sleep and/or the quality of sleep. Disrupted pre-op sleep may predict post-op pain, which may be used to define a tailored/customized pain management strategy. Disrupted sleep may indicate elevated inflammation and/or reduced immune function. Different sleep cycles may be identified, for example, by changes in heart rate, respiration rate, temperature, movement, brain activity, etc. Sleep cycles may be recognized/identified and quantified, for example, using one or more sensors (e.g., to monitor heart rate, breathing or respiration rate, body temperature, movement, and/or brain activity). Heart rate (e.g., measured by ECG) may, for example, drop during deep sleep, rise during REM sleep, and (e.g., gradually) rise again before waking up. Breathing or respiration rate (e.g., measured acoustically by a microphone) may, for example, drop during deep sleep. Poor sleep quality may be indicated, for example, by episodes of apnea. Body temperature (e.g., measured by a thermometer) may drop during deep sleep. Movement (e.g., measured by an accelerometer and/or microphone) may be significantly suppressed, for example, in deep sleep. Sleep time and quality may be inferred from EEG readings. Brain signals may vary depending on the nature of sleep. Deep sleep may be indicated, for example, by slow, large amplitude brain waves. REM sleep may be indicated, for example, by fast, wake-like signals. In some examples, a headband worn by a patient may track EEG, heart rate and/or movement. In some examples, movement may be detected based on audible sounds detected by a microphone and/or by an accelerometer, which may be processed by an application (e.g., a smartphone app) to determine (e.g., infer) a sleep state.

GI motility, may (e.g., be used to) identify, for example, to determine pre- or post-op intestinal obstruction (e.g., ileus). GI motility may be measured, for example, by one or more sensors in a stomach patch, a band, an electrogastroenterography (EGGG) wearable stethoscope, ultrasound, and/or an ingestible capsule, which may measure, for example, pH, temperature, pressure, etc.

Blood sugar levels, may (e.g., be used to) identify, for example, a patient's ability to heal, diabetes, etc.

Hydration state, may (e.g., be used to) identify a patient's hydration level, such as dehydration, which may have a negative impact on health and healing. Hydration state may provide a context for one or more other patient biomarkers, such as heart rate. Dehydration may reduce blood volume. Hydration state may help predict a risk of post-op acute kidney injury (AKI). Reduced blood flow to the kidneys may cause AKI. Hydration state may predict whether a patient may be at risk of hypovolemic shock during or after surgery. Hydration state may be (e.g., continuously) measured outside a healthcare environment (e.g., in a home environment). Hydration state may be influenced by various factors throughout a day (e.g., exercise, fluid intake, temperature). Hydration state may be measured, for example, by a wearable sensor (e.g., a bracelet, watch, patch). Sensing/detection may include, for example, optical spectroscopy and/or sweat-based colorimetry. Water may have characteristic absorption peaks. Peaks may be detected, e.g., by optical spectroscopy, for example, by measuring the amount of incident light that is reflected when shone onto the skin. The water content may be inferred from the differential amplitudes of different wavelengths, e.g., 1720, 1750 and 1770 nm. Hydration state may (e.g., additionally and/or alternatively) be measured similar to the way in which sweat rate may be measured, e.g., by sweat-based colorimetry. Hydration may be inferred from the amount of sweat produced. Sweat-based colorimetry may be more indirect than optical spectroscopy. Sweat-based colorimetry may utilize user information (e.g., such as a user keeping track of activity and water intake), for example, to determine hydration.

Temperature (e.g., core body temperature), may (e.g., be used to) identify, for example, infection, menstrual cycle, etc. Core body temperature in healthy individuals may vary between 36.5-37.5° C. Core body temperature may help indicate signs of post-op infection/sepsis (e.g., abnormal temperatures greater than 38.5° C. or less than 35° C. and/or characteristic fluctuations, such as 0.4° C. fluctuations). Body temperature may be measured by a (e.g., wearable) sensor. Temperature may be influenced, for example, by activities, such as exercise, climate, etc. Temperature may be analyzed alone and/or in conjunction (e.g., combination) with activities, exercise, sleep, environmental temperature, for example, to provide context to temperature measurements. Temperature may be measured, for example, by a wearable device, such as a chest strap, and/or an ingestible sensor. For example, an ingestible thermometer system may directly measure core body temperature. The system may wirelessly transmit the temperature detected by a sensor as it passes through the digestive tract (e.g., over a period of 24-36 hours). The system may use, for example, a quartz-crystal temperature sensor, which may determine temperature via the crystal's vibrational frequency. A wearable antenna may be used to detect electromagnetic radiation in the microwave region which, unlike IR radiation, can pass through the skin from tissue several centimeters below the surface. People, like all matter, emit blackbody radiation with a frequency spectrum determined by temperature. Core temperature may be inferred by measuring emission spectra of the body.

Tissue perfusion pressure may (e.g., be used to) identify, for example, surgical tool parameters, hypovolemia, internal bleeding, etc. Skin perfusion pressure may be proportional to the perfusion of other, deeper, tissue (e.g., organ tissue). Water content may contribute to mechanical properties of tissue. Tissue perfusion pressure may be monitored, for example, pre-surgery, in-surgery, and/or post-surgery. Tissue perfusion pressure before surgery may indicate mechanical properties of tissue, which may be used to set or adjust surgical procedure and/or parameters. A drop in perfusion pressure (e.g., post-surgery) may indicate hypovolemia or internal bleeding. Skin perfusion pressure may (e.g., be used to) monitor the overall adequacy of perfusion. Patients may be discharged earlier, for example, by use of home monitoring. Tissue perfusion pressure may be measured by a (e.g., wearable) sensor, such as a wrist band (e.g., bracelet or watch) or armband. Skin perfusion pressure may be measured, for example, optically. Measurement may vary, for example, depending on the applicability of controlled occlusion. Photoplethysmography may be implemented without application of pressure, for example, if occlusion is not applied. A device may illuminate skin and measure the light transmitted and reflected to detect changes in blood flow. Skin perfusion pressure may be (e.g., additionally and/or alternatively) measured as the pressure to restore blood flow after occlusion (e.g., if occlusion is applied). Pressure may be measured, for example, with a strain gauge or laser doppler flowmetry, which may measure the change in frequency of light caused by movement of blood. The magnitude and distribution of the shift may be (e.g., directly) related to the number and velocity of red blood cells, from which pressure may be calculated.

One or more (e.g., pre-surgery) patient biomarkers may be utilized in one or more analyses (e.g., algorithms) for a surgical procedure, such as a thoracic surgical procedure, for example, to provide one or more recommendations, determinations, actions, and/or implementations that may reduce or prevent one or more potential or predicted complications (e.g., PAL), whether intra-operative (in-surgery) or post-operative (post-surgery) complications. A patient sensing system may communicate one or more patient biomarker measurements to a surgical hub or system. One or more patient biomarker measurements may be processed (e.g., in whole or in part) to determine complication probability, reduction and/or avoidance measures, for example, by one or more (e.g., wearable) devices associated with a patient (e.g., a device with one or more patient biomarker sensors, a device receiving information from one or more patient biomarker sensors, a sensing system, a computing device, such as a cellular phone or tablet) and/or by a surgical hub or a computing system that may (e.g., in turn) notify an HCP of the probabilities of one or more complications and/or remedial recommendations (e.g., recommended actions) and/or actions to reduce or avoid potential complications.

Examples of notifications, recommendations, determinations, actions, and/or implementations (e.g., that may reduce or prevent one or more potential or predicted complications) may include, for example, one or more of the following: a selection or modification/change in a surgery plan, instrument choices, surgical approach, instrument configurations and/or schedule (e.g., of surgery and/or order of use of instruments during surgery). A notification may include, for example, one or more suggestions and/or determinations, such as one or more of the following: potential issue areas, procedure plan adjustments, alternative product mixes, and/or adjustment of control program parameters to interlinked smart instruments.

An example of a notification or recommendation is a control program. A control program or a portion thereof may be selected or changed, modified or updated (e.g., based on monitoring and/or analyses of one or more patient biomarkers), for example, to select or alter operation of one or more devices, such as one or more surgical devices and/or other devices used in-surgery, and/or one or more monitoring and/or other devices used post-surgery. The type of control program(s), selection(s) and/or change(s) may depend on the patient biomarker measurement(s) and/or processing (e.g., based on baseline value(s), types of control available). A control program may include, for example, control parameters that may be selected or adjusted for a control program.

In some examples, a patient biomarker monitoring/analysis system may be configured to communicably couple to a surgical hub. The surgical hub may be configured to communicably couple to one or more in-surgery and/or post-surgery (e.g., recovery) devices that may be controlled by one or more control programs. A patient biomarker monitoring/analysis system may comprise, for example: a processor and a memory coupled to the processor. The memory may store instructions that, when executed by the processor, cause the patient biomarker monitoring/analysis system to perform a method or procedure (e.g., as follows). For example, a patient biomarker monitoring/analysis system may receive data/information indicative of an operational behavior of a device. For example, the data/information may include data detected by the device during and/or after a surgical procedure. The patient biomarker monitoring/analysis system may receive patient biomarker data/information associated with the patient. The patient biomarker monitoring/analysis system may analyze the data/information indicative of an operational behavior of the device and the patient's patient biomarker monitoring data/information to determine whether the operational behavior of the device is or may be suboptimal for the patient. The patient biomarker monitoring/analysis system may generate a control program update configured to alter the manner in which the control program operates the device(s) (e.g., in-surgery and/or post-surgery) for the operational behavior. The patient biomarker monitoring/analysis system may transmit the control program update to the device, which may execute the updated control program.

A control program may be sent (e.g., by a surgical hub) to a sensing and/or control system. A processor (e.g., in a surgical hub) may be configured, for example, to send a control program (e.g., an adjustment or update to a program). The control program may be configured to modulate a suction level of a chest tube system connected to the patient. The control program may be received (e.g., and implemented) by one or more devices in (e.g., sensing systems) that may communicatively be connected with the source of the control program. In some examples, the suction level may be modulated, for example, based (e.g., at least in part) on a (e.g., sensed/measured) phase of respiration. The suction level may be modulated, for example, based (e.g., at least in part) on one or more (e.g., sensed/ measured) patient biomarkers, such as diaphragmatic muscle tone.

The type of control program update that may be generated (e.g., by a patient biomarker monitoring/analysis system) and may depend upon the one or more suboptimal behaviors exhibited by the one or more devices identified by the patient biomarker monitoring/analysis system. For example, a patient biomarker monitoring/analysis system may determine that (e.g., based on one or more analyses of patient biomarker measurement data/information) a particular (e.g., default, preexisting, or preselected) force to fire a surgical stapling instrument may result in an increased rate of leaking staple lines. The patient biomarker monitoring/analysis system may select, generate, update or otherwise indicate a control program that adjusts the force to fire from a first value to a second value that corresponds to a lower rate of leaking staple lines (e.g., a higher rate of non-leaking staple lines). As another example, a patient biomarker monitoring/ analysis system may determine (e.g., based on one or more analyses of patient biomarker measurement data/information) that a particular (e.g., default, preexisting, or preselected) energy level for an electrosurgical or ultrasonic instrument may produce a low rate of hemostasis, for example, if/when the instrument is used in a liquid-filled environment (e.g., due to the energy dissipating effects of the liquid). The patient biomarker monitoring/analysis system may select, generate, update or otherwise indicate a control program that adjusts the energy level of the instrument when it is utilized in a surgical procedure (e.g., if/when the instrument will be immersed in liquid) for a patient based on the patient's patient biomarker monitoring.

The type of control program update that is generated (e.g., by a patient biomarker monitoring/analysis system) may depend upon whether the suboptimal behavior exhibited by an in-surgery and/or post-surgery (e.g., recovery) device is a matter of manual control or automated control (e.g., by a control program of the device). A control program update may be configured (e.g., for manual control) to provide (e.g., for display and/or other indication) warnings, recommendations, or feedback to a user (e.g., a surgeon, nurse), for example, based upon the manner in which the user is operating the device. A control program update may change a manually controlled operation of a device to an (e.g., automated) operation that may be controlled by a control program of the device. The control program update may or may not permit the user to override the control program's control of the particular function. For example, patient biomarker monitoring/analysis system may determine that surgeons are manually setting an RF electrosurgical instrument to a suboptimal energy level for a particular tissue type or procedure type. The patient biomarker monitoring/analysis system may generate a control program update that provides an alert (e.g., on a surgical hub and/or on the RF electrosurgical instrument itself) recommending that the energy level be changed. In another example, the generated control program update may (e.g., automatically) set the energy level to a default or recommended level (e.g., given the particular detected circumstances), which may be changed as desired by the user (e.g., medical facility staff). In an (e.g., additional and/or alternative) example, the control program update may (e.g., automatically) set the energy level to a level determined by the patient biomarker monitoring/analysis system without permitting a user (e.g., the medical facility staff, such as an HCP) to change the energy level. The control program update may alter how the control program functions (e.g., under the particular set of circumstances), for example, if the suboptimal behavior is caused by the control program of the device.

Post-surgery monitoring of a patient may be established and/or adjusted, for example, based on a risk based predictive model of a patient, which may use one or more pre-, in- and/or post-surgery patient biomarker levels, one or more procedure impacts (e.g., removal of a portion of an organ, such as a lung), and/or (e.g., potential) complications to make patient-specific determinations. One or more criticality levels and/or responses or escalation points may be established (e.g., set or selected) and/or adjusted (e.g., increased or decreased), for example, based on a predictive model analysis of one or more pre-surgery patient biomarker levels, and/or one or more procedure impacts and/or complications. Surgical prep and/or in-surgery procedures may be established and/or adjusted, for example, based on one or more pre-, in-, and/or post-surgery patient biomarker levels, one or more procedure impacts, and/or (e.g., potential) complications.

In some examples, a surgical hub (e.g., and/or a (wearable) sensing system) may include/comprise a processor configured to perform a method. For example, one or more processors may be configured to receive measurement data from at least one sensing system. The measurement data may be associated with one or more (e.g., a set of) patient biomarkers. The surgical hub (e.g., and/or a (wearable) sensing system) may (e.g., be configured to) predict an occurrence of a complication (e.g., a prolonged air leak (PAL)), for example, based (e.g., at least) on the measurement data associated with the set of patient biomarkers. The surgical hub (e.g., and/or a (wearable) sensing system) may (e.g., be configured to) generate a set of recommendations for preventing the PAL.

In various examples, one or more (e.g., all) patient biomarkers in the set of patient biomarkers may be pre-, in- and/or post-surgery patient biomarkers. A processor may be configured to generate one or more (e.g., a set of) thresholds (e.g., for one or more patient biomarker measurements) for monitoring a potential complication (e.g., an in-surgical PAL or a post-surgical PAL), for example, if an occurrence of the complication (e.g., PAL) is predicted (e.g., by a patient prediction model). Generation of one or more thresholds may be triggered, for example, if a likelihood of a predicted complication exceeds a threshold. A processor may be configured to send the one or more generated thresholds to a patient monitoring system and/or to an HCP.

An occurrence of a complication, such as a PAL, may be (e.g., additionally and/or alternatively) predicted or determined (e.g., by a model used for predicting a complication, such as a PAL) based on a set of patient parameters, such as one or more of the following variables (e.g., predictive or determinative variables): a patient's age, a patient's body-mass index (BMI), nutritional status, forced expiratory volume (FEV) in one (1) second (FEV1) percentage, and/or presence of pleural adhesions (e.g., as may be observed during operation).

The probability of a complication, such as a PAL, may vary based on one or more patient characteristics and/or patient biomarker measurements. For example, the probability of a PAL occurring in a patient older than 65 years of age may be 0.04 or 4%. The probability of a PAL occurring in a patient with a BMI of less than 25.5 m/kg^2 may be, for example, less than 0.0001 or 0.01%. A BMI of less than 25.5 m/kg^2 may be an indication of poor nutritional status and/or chest mechanics (e.g., the ratio of the size of lung space to the size of available chest space). Nutritional status may be (e.g., additionally and/or alternatively) determined, for example, based on one or more of the following patient biomarkers: sweat, tears, urine, alcohol use, blood/serum ratio, saliva, etc.

A sweat patient biomarker may be measured, for example, as a sweat rate, e.g., with units $\mu$L/hour/cm2. A threshold may be determined, for example, over time. Sweat rate may indicate activity of a sympathetic nervous system. Sweat rate may help indicate psychological stress (e.g., preoperative anxiety), which may be associated with heightened sympathetic activity that may (e.g., in turn) be correlated with post-op pain. Sweat rate may (e.g., in part) indicate post-op infection. Infection may cause secondary hyperhidrosis. Sweat rate may be measured, for example, through a wearable sensor (e.g., in a home environment). Sweat may be affected by various factors in the day (e.g., climate, exercise). Sweat rate may be combined with other (e.g., contextual) patient biomarkers, such as heartrate, breathing rate, and/or activity/exercise, which may place sweat rate in context. Sweat and sweat rate may be sensed (e.g., by a wearable sensor, such as a patch, pad, band, bracelet, watch, etc. in contact with the skin), for example, based on sweat captured from the surface of the skin (e.g., in microfluidic channels). Sweat rate may be calculated (e.g., from microfluidic capture), for example, by a colorimetric technique and/or an impedimetric technique. In an example of a colorimetric-based determination, a water-responsive chromogenic reagent within one or more microfluidic channels may cause sweat to change color (e.g., on contact). A sweat rate may be calculated, for example, by monitoring the position of the leading edge of the color change as a function of time. In an example of an impedimetric determination, sweat may (e.g., gradually) cover multiple electrodes (e.g., two spiral electrodes), for example, as the microfluidic channel is filled. A change in impedance may be detected between the multiple electrodes, for example, as a function of time.

A tear patient biomarker may be measured by a tear sensor, which may be implemented, for example, in a wearable sensor (e.g., a patch). A urine patient biomarker may be measured by a urine sensor, which may be implemented, for example, in a wearable sensor (e.g., in a diaper). A blood/serum ratio patient biomarker may be measured by a blood/serum ratio sensor, which may be implemented, for example, in a wearable sensor. A saliva patient biomarker may be measured by a saliva sensor, which may be implemented, for example, in a wearable sensor. Wearable (e.g., on person) sensors may be attached in place for sensing or may be moved to a sensor location (e.g., periodically, such as in response to an indication to use the sensor to take a measurement). For example, a saliva sensor worn on a necklace may be moved into position temporarily for a sample.

An alcohol patient biomarker may be measured, for example, as blood alcohol concentration (BAC). A threshold may be based on one or more characteristics (e.g., sex, weight). Patients who drink alcohol (e.g., three or more alcohol units (AUs) per day) may have a reduced immune capacity. For example, a BAC threshold (e.g., an average BAC threshold) for reduced immunity may be greater than 0.04 BAC for a male weighing 80 kilograms (kg) and greater than 0.07 BAC for a female weighing greater than 60 kg. Measuring alcohol consumption may provide information to make determinations and/or take actions (e.g., precautions) to reduce or avoid potential complications, such as post-surgery infections, cardiopulmonary complications, bleeding, etc. Monitoring patient alcohol consumption in natural environments (e.g., at home) may provide a more accurate measurements (e.g., compared to hospital measurements). An alcohol use patient biomarker may be measured by an alcohol sensor, which may be implemented, for example, in a wearable sensor (e.g., a patch, band, bracelet, watch). An alcohol sensor may include, for example, transdermal and/or microfluidic monitoring. Transdermal alcohol monitoring may provide continuous monitoring of alcohol consumption. A transdermal sensor (e.g., in a device such as a bracelet) may be worn next to the skin to sample (e.g., otherwise insensible) perspiration. A pump inside a device (e.g., bracelet) may take a sample (e.g., of sweat). The presence of alcohol in the sample (e.g., sweat) may be measured, for example, based on a reaction between ethanol in the sample and a fuel cell (e.g., similar to a fuel cell used in a breath sensor). A blood alcohol level may be calculated based on the measurement.

Patient biomarker (e.g., pre-, in-, and/or post-surgery patient biomarker) monitoring may provide information to an HCP and/or a patient (e.g., prior to a surgery), for example, to avoid a complication, such as a PAL. A patient with an FEV1 of less than 80% may have a low probability of developing a PAL (e.g., a probability of 0.0001 or 0.01%). A patient with pleural adhesions (e.g., confirmed during operation) may have a relatively low probability of developing a PAL (e.g., a probability of 0.01 or 1%). A likelihood that a patient may have pleural adhesions may be indicated (e.g., anticipated or predicted), for example, by a history of unusual menstrual cycles (e.g., short menstrual cycles).

A surgical hub (e.g., and/or a (wearable) sensing system) may include a processor configured to receive measurement data from at least one sensing system. The measurement data may be associated with one or more (e.g., a set of) patient biomarkers. The surgical hub (e.g., and/or a (wearable) sensing system) may (e.g., be configured to) predict an occurrence of a complication (e.g., a prolonged air leak (PAL)), for example, based (e.g., at least) on the measurement data associated with the set of patient biomarkers. The surgical hub (e.g., and/or a (wearable) sensing system) may (e.g., be configured to) generate a set of recommendations for preventing the complication (e.g., PAL).

A recommendation may be a selection and/or adaptation (e.g., change or modification of a default or existing selection) of one or more of the following: surgical preparation, in-surgery procedures, surgical instrument selection, surgical and/or post-surgical instrument settings, post-surgery procedures, in-surgery and/or post-surgery monitoring (e.g., recovery), etc. A recommendation may be selected or adapted to reduce or avoid one or more predictable complications, for example, based on patient biomarker monitoring alone or in combination with other information before, during and/or after surgery. For example, one or more patient biomarkers may (e.g., be used to) determine one or more stapling recommendations and/or stapling settings to avoid or minimize one or more potential complications, such as a PAL. A recommendation may be based on patient biomarkers that pertain to the likelihood of a patient developing a PAL.

In some examples, a set of recommendations for preventing the PAL (e.g., predicted based on measurement data associated with one or more patient biomarkers) may include at least one of the following: one or more stapling recommendations or settings, one or more post-stapling recommendations, or one or more surgical procedural recommendations, and/or one or more post-surgical recommendations.

In some examples, the one or more stapling recommendations or settings may include at least one of: applying a buttressed staple line, avoiding overlapping parenchymal staple lines, and/or stapling using a cautious mode on a powered stapling device. For example, a recommendation may be generated and/or provided for a surgical stapling instrument used in a surgical procedure to use a buttress material to reinforce the fastening of tissue provided by staples. For example, a recommendation may be generated and/or provided to pay increased (e.g., additional or careful) attention (e.g., during a procedure) to avoid overlapping parenchymal staple lines. For example, a recommendation may be generated and/or provided to set a power stapler to operate using a Cautious Mode.

In some examples, a recommendation or setting may include a cautious mode. A recommendation and/or an implementation of the recommendation may include a modified speed setting and/or a modified force setting. A stapler may be set to operate (e.g., based on a recommendation to operate in a Cautious Mode) at a (e.g., selected or modified) speed and/or force, for example, for (e.g., critical) staple lines on (e.g., thicker) lung tissue. A Cautious Mode may be recommended/selected (e.g., for a surgical instrument, such as a power stapler), for example, for advanced hemostasis (e.g., for vessels with greater than 7 mm thickness).

In some examples, the one or more post-stapling recommendations or settings may include at least one of: using a low inspiratory pressure if/when inflating a lung and/or using a sealant. For example, a recommendation may be generated and/or provided for an HCP and/or a surgical instrument used in a surgical procedure (e.g., a post-stapling procedure) to use a low inspiratory pressure if/when inflating a lung and/or if/when using a sealant.

In some examples, the one or more surgical procedural recommendations or settings may include at least one of: controlling a number of dissections, creating an apical tent, or creating a pneumoperitoneum. For example, a recommendation may be generated and/or provided for an HCP and/or a surgical instrument used in a surgical procedure to a specified number of dissections and/or to reduce, increase, or otherwise control the number of dissections. For example, a recommendation may be generated and/or provided for an HCP and/or a surgical instrument used in a surgical procedure to create an apical tent. For example, a recommendation may be generated and/or provided for an HCP and/or a surgical instrument used in a surgical procedure to create a pneumoperitoneum.

In some examples, the one or more post-surgical procedural recommendations or settings may include at least one of: whether or not to use a water seal, or whether or not to use suction. For example, a recommendation may be generated and/or provided for an HCP and/or a post-surgical instrument (e.g., used in a post-surgical procedure) to use or to not use a water seal. For example, a recommendation may be generated and/or provided for an HCP and/or a post-surgical instrument (e.g., used in a post-surgical procedure) to use or to not use suction.

Recommendations may be based on the likelihood of a patient developing a complication. A likelihood of a complication may be patient specific, e.g., based on patient information, including patient biomarker measurements. For example, a recommendation indicating whether or not to use a water seal and/or suction may be based on a degree of likelihood of a patient experiencing pneumothorax (e.g., determined based on patient-specific information, including patient biomarker measurements).

In some examples, a patient biomarker analysis and/or patient biomarker specific adjustment process may be implemented by a surgical hub and/or a wearable sensing system, for example, to customize patient surgery and/or treatment-based patient biomarker monitoring. In some examples (e.g., as shown in FIG. 18) a patient-specific process may be implemented at or near the end of a surgery and/or a portion thereof. For example, the process may occur after (post) stapling. In an example, a pre-surgery (pre-op) patient biomarker analysis may indicate a patient is at a higher risk of developing a PAL. A surgical procedure (e.g., on the patient's lung) may be completed (e.g., at least in part, such as after stapling). A determination may be made about an inspiratory pressure to re-inflate the lung. The lung may be submerged (e.g., in sterile saline), for example, to check for air leaks. A determination may be made whether there is an air leak. A determination may be made (e.g., if an air leak is detected), about the magnitude of the detected air leak. A surgical procedure may be completed or may end, for example, if a leak is not detected. One or more procedural recommendations may be made, for example, based on a detection of a leak and/or based on an analysis of patient biomarker monitoring indicating a probability of a complication, such as a PAL. A recommendation may include, for example, suturing, using/adding a sealant, and/or the like, e.g., to seal the leak and/or to reduce or avoid a complication.

One or more (pre-surgery, in-surgery, and/or post-surgery) procedural recommendations may be generated, for example, based on one or more analyses of one or more monitored patient biomarkers. The number of cuts (e.g., dissection) may be correlated with exposed raw parenchymal surface area, for example, to determine (e.g., output) a risk of a patient developing a PAL. In some examples, the right upper lobe may anatomically abut multiple (e.g., two) fissures. A minor fissure may be nearly complete. More dissection in the fissure may expose a larger parenchymal raw surface area. In some examples, a recommendation to reduce the likelihood of developing a complication, such as a PAL, may include, for example, creating an apical pleural tent, e.g., at the time of an upper lobectomy. In some examples, a recommendation to reduce the likelihood of developing a complication, such as a PAL, may include creating a pneumoperitoneum, e.g., at the time of a lower lobe resection.

A (e.g., post-op) recommendation (e.g., based on patient biomarker monitoring) to reduce the likelihood of developing a complication, such as a PAL, may include creating a water seal and/or suction. Recommendations may be patient-specific, e.g., based on patient biomarker monitoring. For example, a water seal may not be recommended for a patient indicated to have a likelihood for pneumothorax (e.g., based on an analysis of patient biomarkers). Suction may not be recommended for patients who may be at risk for impaired healing. Suction may delay parenchymal healing, may lead to the rupture of blebs/bullae, and/or may prolong an air leak.

Post-surgical patient monitoring may track one or more complications (e.g., infection). One or more treatment plans may be generated, selected, or adapted, for example, based on one or more analyses of one or more monitored patient biomarkers. One or more (e.g., a combination of) metrics may provide insight into early infection post-surgery. For example, tracking resting heart rate, body temperature, and respiratory rate in combination may provide a picture of health progression after a surgical procedure.

An acute response to a foreign body may be indicated or detected (e.g., over one or more time periods), for example, by detecting an increase in average resting heart rate (e.g., a 5-10% increase per day), an increase in average body temperature change (e.g., a 1-2 degree f increase per day), and/or an increase in respiratory rate (e.g., a 15-30% increase per day).

An event (e.g., a complication) may be predicted with improved accuracy, for example, by determining baseline values for patient biomarkers prior to surgery. Patient-specific or tailored metric thresholds may improve predictions of the occurrence of an event.

Patient biomarker measurements may be performed with one or more devices, such as a single device (e.g., a ring) or multiple devices (e.g., a bracelet or a watch and a ring), for example, as illustrated in FIGS. 13 and 15, and also described in FIGS. 11A-11D.

Patient biomarker measurement data/information may provide an (e.g., earlier) opportunity to intervene before a patient's immune response becomes more substantial and/or an infection becomes more widespread (e.g., as may be indicated by a high body temperature).

Patient biomarker measurement data/information may reduce erroneous and/or incomplete data/information from spot measurements. A (e.g., discrete) spot measurement (e.g., once or twice per day) may be performed, for example, using a temple, no-contact thermometer, which may pick up transient aberrations and/or miss trends.

Post-surgical patient monitoring (e.g., including analyses of patient biomarker measurements) may (e.g., be used to) generate one or more pain management plans, which may include administration of analgesics/narcotics. Post-surgical patient monitoring may measure one or more parameters, such as skin conductance, hormone levels (e.g., cortisol), heart rate and heart rate variability, etc. Patient monitoring may indicate, for example, autonomic nervous system activity. Patient monitoring may provide quantitative and/or objective metrics to guide analgesic administration post-surgery.

Patient monitoring may guide duration of effect, for example, to indicate how long a given analgesic may provide a desired effect. Patient monitoring may guide dosage, for example, to provide an (e.g., optimal) effect with the lowest possible dosage. Patient logging of analgesics/narcotics taken over time may correspond to a timeline of changes in measured parameters, which may indicate or may be used to detect improvements in health.

Methods may be implemented (e.g., in whole or in part), for example, by one or more devices, apparatuses, and/or systems (e.g., a hub, a sensing system, and/or the like), which may comprise one or more processors configured to execute the methods (e.g., in whole or in part) as computer executable instructions that may be stored on a computer readable medium or a computer program product, that, when executed by the one or more processors, performs the methods. The computer readable medium or the computer program product may comprise (e.g., store) instructions that cause one or more processors to perform the methods by executing the instructions.

Figure 19:
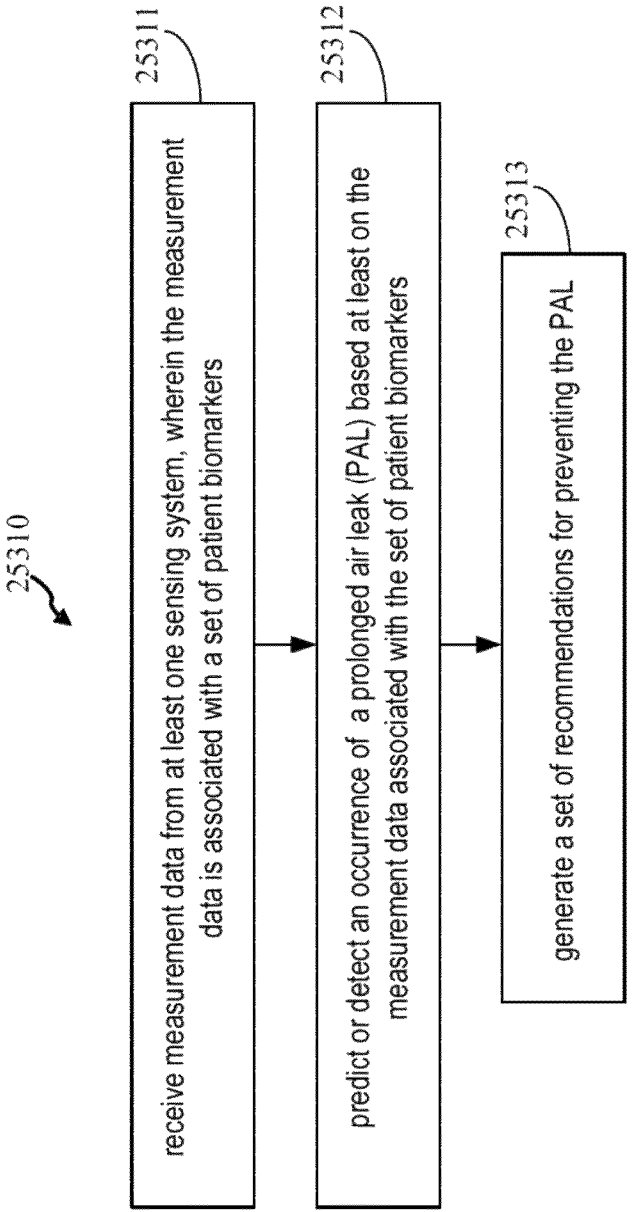
FIG. 19 illustrates an example of a logic flow diagram for predicting a PAL, in accordance with at least one aspect of the present disclosure.

FIG. 19 illustrates an example of a logic flow diagram of a process for predicting a complication (e.g., a PAL) and providing a recommendation (e.g., about use of a sealant) to attempt to avoid the complication, in accordance with at least one aspect of the present disclosure. In various examples, the process may be implemented (e.g., in whole or in part) in a surgical hub and/or a sensing system. Example process 25310 may be implemented, for example, by patient monitoring system 25251.

At 25311, measurement data may be received. For example, the measurement data may be received from at least one sensing system. The measurement data may be associated with a set of patient biomarkers. For example, hub 25258 may receive measurement data for one or more patient biomarkers shown in FIGS. 16 and 17 from first and as described herein, second or third sensing systems 25253, 25254, 25255 shown in FIG. 13 and for example in FIGS. 11A-11D. The measurement data may be pre-, in-, and/or post-surgery patient biomarker measurement data and/or one or more patient parameters. At 25312, an occurrence of a complication (e.g., a PAL) may be predicted, for example, based at least on the measurement data associated with the set of patient biomarkers. For example, a processor in hub 25258 may execute a patient prediction model that takes as input vectorized patient data generated from measurement data received at 25311 and generates an indication of one or more complications (e.g., a PAL) and associated probabilities of occurrence in the patient based on the vectorized patient data input. At 25313, a set of recommendations may be generated for preventing the complication (e.g., the PAL). For example, the probability of a complication (e.g., a PAL) predicted by hub 25258 may exceed a threshold probability and/or one or more patient biomarkers may exceed one or more thresholds. Hub 25258 may generate one or more recommendations, which may be provided, for example, to one or more of a surgical instrument, an HCP, and/or a patient to take one or more actions on (e.g., to prevent an occurrence of the complication). For example, the recommendation may be provided to a computer to display the recommendation to an HCP to use a sealant to prevent a PAL.

FIG. 20 illustrates an example of a logic flow diagram of a process for a surgical hub for detecting a post-operative complication, in accordance with at least one aspect of the present disclosure. Example process 25320 may be implemented, for example, by patient monitoring system 25251.

At 25321, a threshold associated with a patient biomarker may be determined. For example, a first threshold associated with a first patient biomarker and/or a second threshold associated with a second patient biomarker may be determined. The first threshold and/or the second threshold may be determined, for example, based (e.g., at least) on baseline data associated with a patient. For example, hub 25258 may determine thresholds associated with measurement data (e.g., baseline data) for one or more (e.g., at least two) patient biomarkers shown in FIGS. 16 and 17 received from one or more of first, second or third sensing systems 25253, 25254, 25255 shown in FIG. 13.

At 25322, measurement data associated with a patient biomarker may be obtained. For example, a first measurement data associated with the first patient biomarker and a second measurement data associated with the second patient biomarker may be obtained (e.g., received from a sensing system). For example, hub 25258 may obtain (e.g., receive) measurement data for one or more patient biomarkers shown in FIGS. 16 and 17 from first, second or third sensing systems 25253, 25254, 25255 shown in FIG. 13.

At 25323, measurement data associated with the patient biomarkers may be monitored and a thoracic post-surgical complication may be predicted or detected based at least on the monitoring. For example, a thoracic post-surgical complication may be predicted or detected based at least on monitoring, which comprises comparing (e.g., in real time) the first measurement data with the first threshold and the second measurement data with the second threshold. For example, hub 25258 may detect an occurrence of a complication (e.g., PAL) based at least on monitoring, which comprises comparing (e.g., in real time) the received measurement data (e.g., with or without processing) obtained at 25322 to the first and second thresholds determined at 25321.

At 25324, a notification (e.g., a real-time notification) may be generated. The notification may indicate the occurrence of the thoracic post-surgical complication, for example, if/when at least one of the first measurement data crosses the first threshold and/or the second measurement data crosses the second threshold (e.g., for a predetermined amount of time). In an example, hub 23258 may generate a (e.g., real-time) notification indicating the occurrence of a complication, if/when the first measurement data crosses the first threshold and/or the second measurement data crosses the second threshold (e.g., for a predetermined amount of time).

At 25325, an actionable notification associated with the occurrence of the thoracic post-surgical complication may be generated. For example, hub 25258 may (e.g., based on the detected occurrence of the complication) generate one or more recommendations to take one or more actions.

The real-time notification and the actionable notification associated with the occurrence of the thoracic post-surgical complication may be sent to the patient and/or a healthcare provider (HCP). For example, hub 25258 may send an indication of the detected complication and an indication of the recommended action(s) to counteract the complication, for example, to an HCP and/or a patient to alert them to take one or more actions on (e.g., to counteract the detected occurrence of the complication). For example, the indications may be provided to one or more devices for visual, aural, touch, and/or other indication to a patient and/or HCP. In an example, the actionable notification associated with the occurrence of the thoracic post-surgical complication may be sent to the patient and/or a healthcare provider (HCP) based on a severity level of the real-time notification.

For example, the actionable notification may be sent when the severity level of the corresponding real-time notification is high.

FIG. 21 illustrates an example of a logic flow diagram of a process for a surgical system for predicting a post-operative complication, in accordance with at least one aspect of the present disclosure. Example process 25330 may be implemented, for example, by patient monitoring system 25251.

At 25331, measurement data from at least one sensing system may be received. The measurement data may be associated with at least one patient biomarker. For example, hub 25258 may receive measurement data for one or more patient biomarkers, as shown in FIGS. 16 and 17 from first, second or third sensing systems 25253, 25254, 25255 shown in FIG. 13. At 25332, a post-operative complication may be predicted, for example, based on the measurement data associated with the at least one patient biomarker and/or based on one or more patient parameters. For example, a processor in hub 25258 may execute a patient prediction model that takes as input vectorized patient data generated from measurement data and/or patient parameters received at 25331 and generate an indication of one or more complications (e.g., a PAL) and associated probabilities of occurrence in the patient based on the vectorized patient data input. The measurement data may be pre-, in-, and/or post-surgery patient biomarker measurement data.

The one or more patient parameters may be taken before, during, and/or after surgery. At 25333, a recommendation to reduce the likelihood of the predicted occurrence of the post-operative complication may be generated. For example, the probability of a complication (e.g., a PAL) predicted by hub 25258 may exceed a threshold probability, one or more patient biomarker measurements may exceed one or more thresholds, and/or one or more patient parameters may exceed one or more thresholds. Hub 25258 may generate one or more recommendations, which may be provided, for example, to one or more of a surgical instrument, an HCP, and/or a patient, e.g., to take one or more actions to reduce the likelihood of an occurrence of the predicted complication. For example, the recommendation may be provided to a computer to display the recommendation to an HCP to use a sealant to prevent a PAL.

Figure 22:
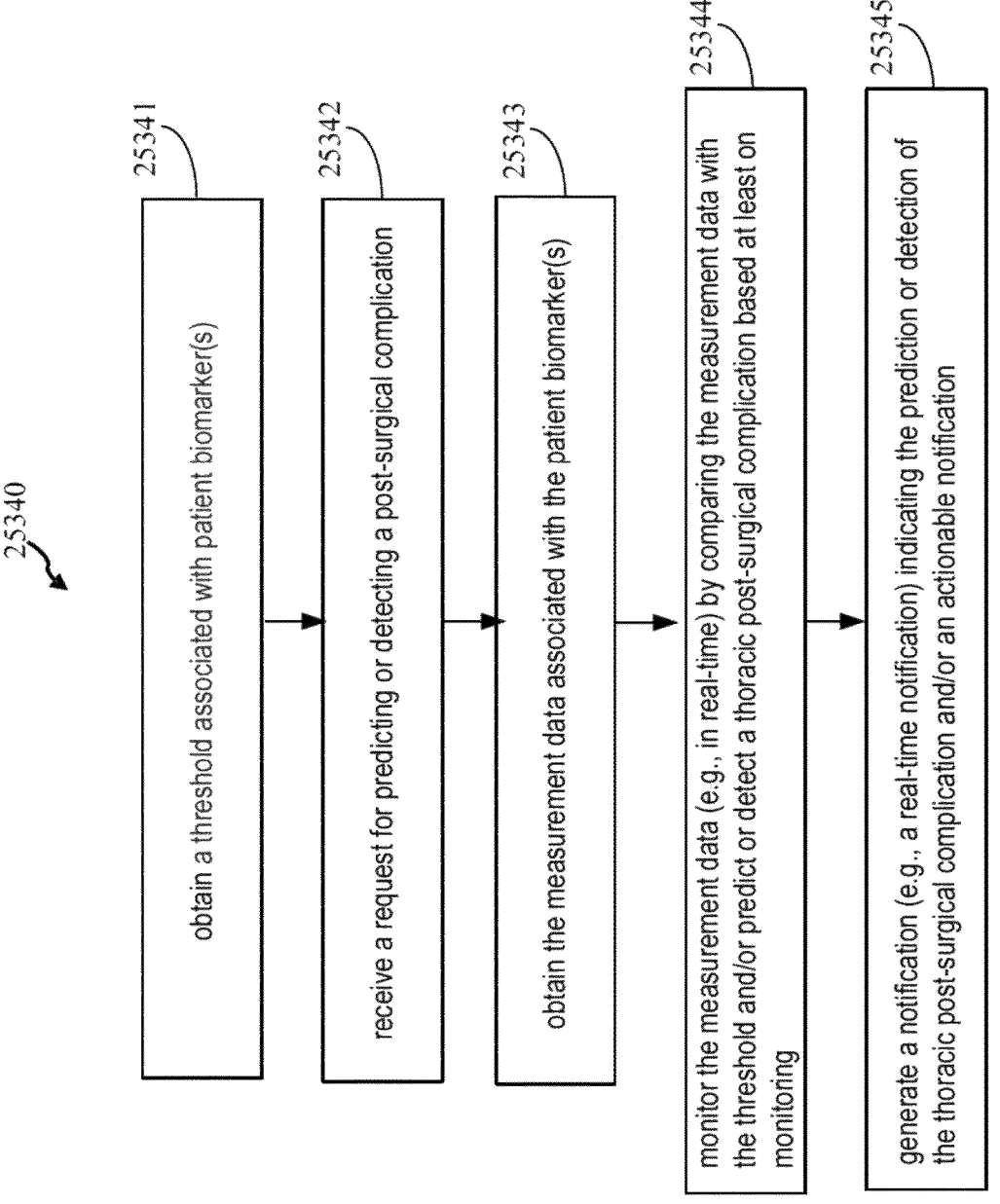
FIG. 22 illustrates an example of a logic flow diagram for detecting post-operative complication, in accordance with at least one aspect of the present disclosure.

FIG. 22 illustrates an example of a logic flow diagram of a process for a sensing system for detecting a post-operative complication, in accordance with at least one aspect of the present disclosure. Example process 25340 may be implemented, for example, by patient monitoring system 25251.

At 25341, a threshold associated with a patient biomarker may be obtained. For example, a first threshold associated with a first patient biomarker and a second threshold associated with a second patient biomarker may be received, for example, from a surgical hub. For example, hub 25258 may determine thresholds associated with at least two patient biomarkers shown in FIGS. 16 and 17. Hub 25258 may provide the thresholds to one or more sensing systems, e.g., first, second, and/or third sensing systems 25253, 25254, 25255 shown in FIG. 13.

At 25342, a request may be received for predicting or detecting a thoracic post-surgical complication. For example, a request may be received for predicting or detecting a post-surgical complication, for example, based on at least one of a first measurement data associated with the first patient biomarker crossing a first threshold or a second measurement data associated with the second patient biomarker crossing a second threshold (e.g., for a predetermined amount of time). For example, first, second, and/or third sensing systems 25253, 25254, 25255 may receive a request from hub 25258 to determine whether a patient is experiencing a complication.

At 25343, measurement data associated with a patient biomarker may be obtained. For example, the first measurement data associated with the first patient biomarker and the second measurement data associated with the second patient biomarker may be measured. For example, first, second, and/or third sensing systems 25253, 25254, 25255 may (e.g., in response to the request) measure at least two patient biomarkers shown in FIGS. 16 and 17.

At 25344, measurement data associated with a set of patient biomarkers may be monitored (e.g., monitored in real time) and/or a thoracic post-surgical complication or a milestone may be detected or predicted based at least on the monitoring. For example, the first measurement data and the second measurement data may be monitored (e.g., in real-time) by comparing each of the first measurement data and the second measurement data with the first threshold and the second threshold respectively. For example, first, second, and/or third sensing systems 25253, 25254, 25255 may (e.g., in response to the request) monitor the measurements of the at least two patient biomarkers shown in FIGS. 16 and 17 and compare the measurements to respective thresholds associated with patient biomarkers received from hub 25258.

At 25345, a notification (e.g., a real-time notification) and/or an actionable notification may be generated, as described, for example, in FIG. 20. For example, a notification indicating the post-surgical complication may be generated based at least on monitoring, which comprises determining (e.g., in real time) if/when the first measurement data crosses the first threshold, or the second measurement data crosses the second threshold (e.g., for a predetermined amount of time). In an example, first, second, and/or third sensing systems 25253, 25254, 25255 may (e.g., in response to the request) generate a notification if/when at least one of the comparisons indicate that at least one of the measured patient biomarkers crosses a respective threshold received from hub 25258.

The (e.g., real-time) notification indicating the occurrence of the post-surgical complication may be sent to the surgical hub. For example, first, second, and/or third sensing systems 25253, 25254, 25255 may (e.g., in response to detecting a post-surgical complication) send the notification of a post-surgical complication to hub 25258.

Figure 23:
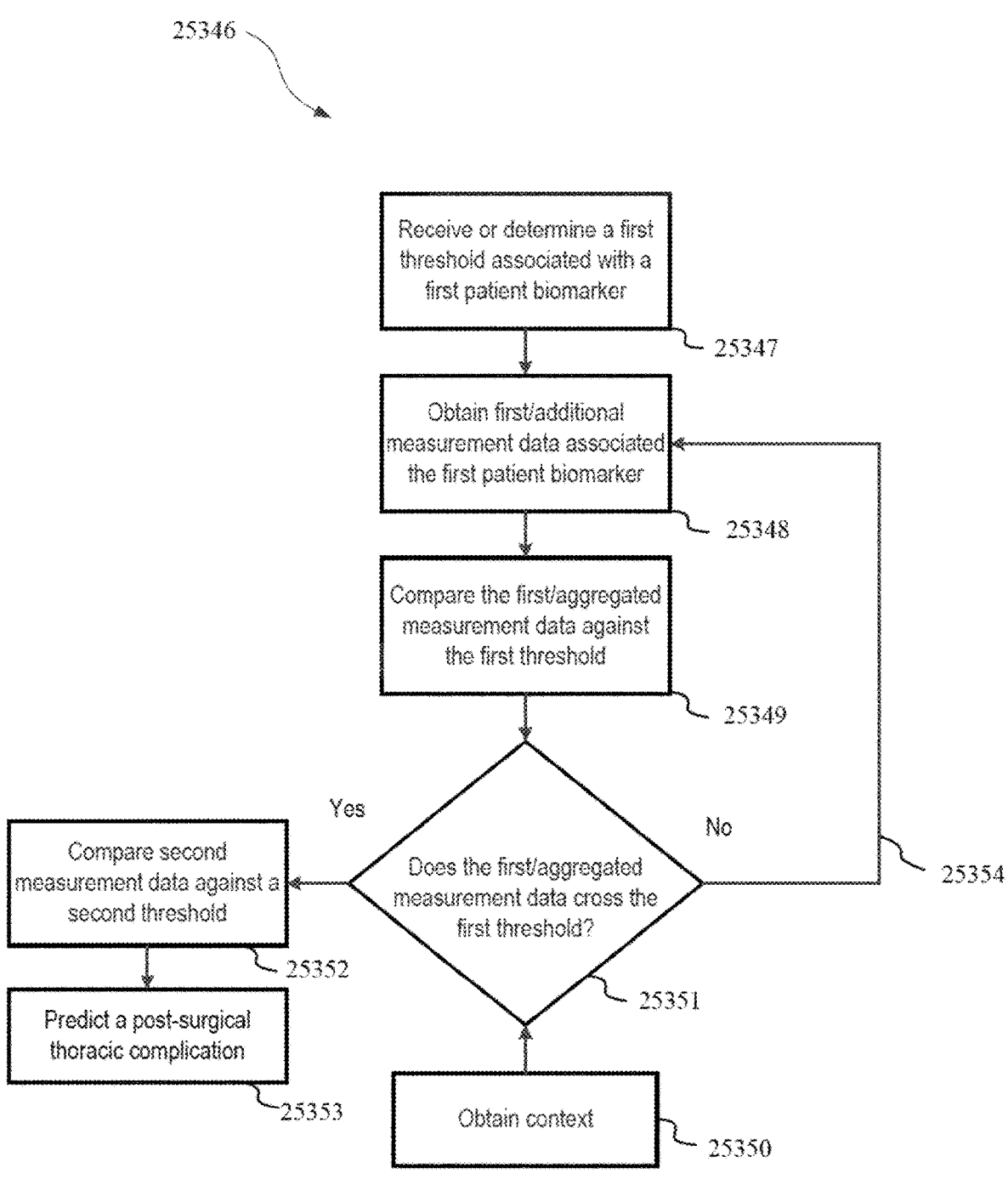
FIG. 23 shows example post-surgical thoracic complication wearable prediction or detection.
Figure 24A:
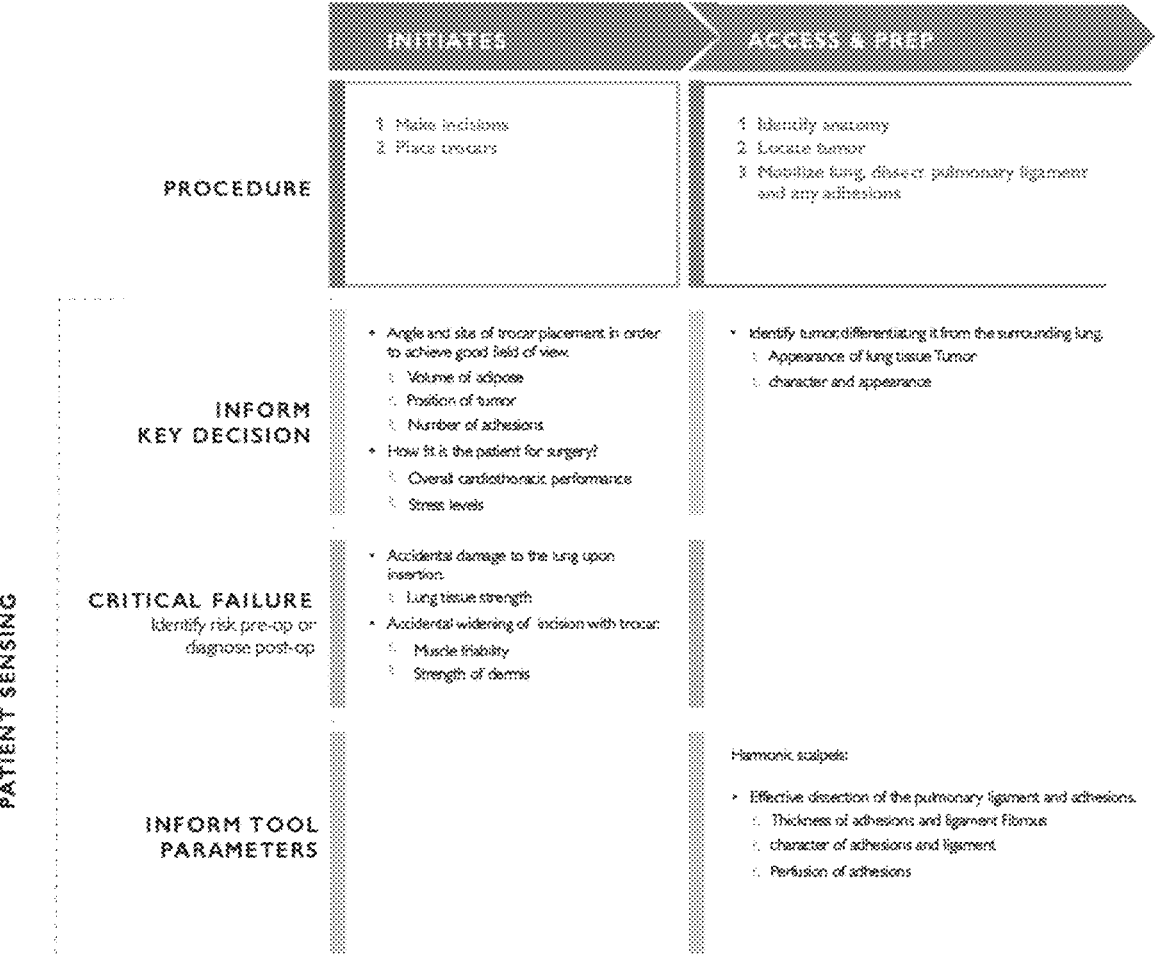

FIG. 23 shows example 25346 post-surgical thoracic complication wearable prediction or detection. One or more of 25347-25354 shown in FIG. 23 may be performed by a computing system, a sensing system, and/or another device described herein.

At 25347, a first threshold associated with a first patient biomarker may be received and/or determined described herein with reference to FIGS. 19-22. For example, a threshold associated with blood pH may be received by a sensing system and/or determined by a computing system. The threshold may be used to predict or detect a post-surgical thoracic complication, for example an air leak.

At 25348, first measurement data associated with the first patient biomarker may be obtained described herein with reference to FIGS. 19-22. For example, measurement data associated with blood pH may be obtained by a computing system and/or a sensing system for predicting or detecting post-surgical thoracic complication. The first measurement data may be obtained as a response to a request for the measurement data. For example, a computing system and/or a sensing system may request the first measurement data.

At 25349, the first measurement data may be compared against the first threshold described herein with reference to FIGS. 19-22.

At 25350, a computing system and/or a sensing system may obtain context described herein with reference to FIGS. 19-22. The computing system may consider the context when determining whether the measurement data crosses the threshold. For example, the computing system may adjust the first threshold based on the received context. The computing system may use the received context as input context data. The input context data may influence the computing system as the computing system determines whether measurement data crosses the threshold.

At 25351, a computing system and/or a sensing system may compare the first measurement data against the first threshold by determining whether the measurement data crosses the threshold (e.g., for a predetermined amount of time) as described herein with reference to FIGS. 19-22. The computing system or the sensing system may compare the first measurement against the first threshold based on a context.

Assuming that the first measurement data, for example, based on the context, crosses the first threshold, at 25352, second measurement data may be compared against a second threshold described herein with reference to FIGS. 19-22. The second threshold may be associated with a second patient biomarker. The second threshold may be received and/or determined similar to how the first threshold may be received and/or determined. The second measurement data may be compared based on a condition that the first measurement data crosses the first threshold for a predetermined amount of time. A computing and/or sensing system may determine that the first measurement data crosses the first threshold for a predetermined amount of time and may compare the second measurement data against a second threshold. In an example, second measurement data may be compared on a condition that the first measurement data crosses the first threshold by a predetermined amount, for example 10% of the first threshold value. The computing system may request the second measurement data when the first measurement data crosses the first threshold.

At 25353, a post-surgical thoracic complication may be predicted described herein with reference to FIGS. 19-22. A computing system and/or a sensing system may predict a post-surgical thoracic complication based on the first measurement data comparison and the second measurement data comparison. For example, the computing system may predict a complication when both the first measurement data and the second measurement data cross the respective first and second thresholds. The computing system may assign weight(s) to each comparison. The computing system may assign a high comparison weight to the first measurement data crossing the first measurement data and a low comparison weight to the second measurement data crossing the second threshold. Predicting a post-surgical thoracic complication may be based on the comparison weight(s). A computing system may be more likely to predict a complication when measurement data associated with a high comparison weight crosses a threshold compared to measurement data associated with low comparison weight crossing a threshold.

At 25354, a computing system and/or a sensing system may determine that the first measurement data does not cross the first threshold for a predetermined amount of time. The computing system may then continue at 25348. Additional or optionally at 25348, the computing system may obtain additional first measurement data. At 25348, the computing system may aggregate the additional first measurement data with the original first measurement data. The aggregated first measurement data may be compared against the first threshold. The computing system and/or sensing system may adjust the first threshold based on the additional first measurement data.

FIGS. 24A-24D illustrates example procedure steps of a lung segmentectomy or a thoracic surgical procedure and example use of patient biomarker measurements. As shown, various post-operative or post-surgical patient biomarker measurements may be used to detect or predict various thoracic post-surgical complications and/or milestones, as described herein. The patient biomarker measurements may also be used to inform various decisions, identify various risks pre-surgery, during surgery, post-surgery, and/or determine operational parameters for various surgical tools.

FIG. 24D illustrates example patient biomarkers that may be monitored post-op to detect or predict post-surgical thoracic complications. The patient biomarkers may be monitored by a computing system or a wearable sensing system as described herein with reference to FIGS. 19-22. For example, a patient's blood pressure may be monitored to detect or predict internal bleeding.

As shown, the patient biomarkers may be measured using one or more wearable and/or environmental sensors as described herein with reference to FIG. 1B. For example, a patient's hydration state may be measured by a wearable patch sensor. A patient's physical activity may be measured by a video camera. Measurement data associated with the wearable and/or environmental sensors may be obtained by a computing system that may compare the data against corresponding threshold(s) as described herein with reference to FIGS. 19-22. In an example, the measurement data may be obtained by a sensing system that may compare the data against corresponding threshold(s).

In an example, a post-surgical air leak may be detected or predicted by measuring patient biomarker(s) associated with a patient's lung tissue repair capacity and/or staple line integrity. Post-surgical lung collapse may be detected by measuring patient biomarker(s) associated with rate of fluid build-up, and/or lung tissue repair capacity. Post-surgical cancer relapse may be detected or predicted by measuring patient biomarker(s) associated with tumor presence and/or metastatic risk. Post-surgical hypovolemic shock may be detected by measuring patient biomarker(s) associated with hydration state. Post-surgical acute kidney injury may be detected by measuring patient biomarker(s) associated with hydration state. In an example, a post-surgical internal bleeding may be detected by measuring patient biomarker(s) associated with blood clotting propensity and/or blood pressure. Post-surgical infection may be detected by measuring poor immune response and/or bacterial populations. In an example, patient biomarker measurements may be used post-op to assess a patient's quality of life following a lung segmentectomy or a thoracic surgery. For example, patient biomarkers associated with VO2 max, physical activity, and/or circadian rhythm may be measured to assess a patient's quality of life.

As shown in FIGS. 24A-24D, patient biomarker measurements may be used post-op to inform various decisions, identify various risks pre-surgery, during surgery, post-surgery, and/or determine operational parameters for various surgical tools. For example, post-op patient biomarker measurements may be used to determine a value (e.g., threshold) in which pre-surgical and/or in-surgical measurement data may be compared against.

The value may be used to inform various decisions during a pre-surgical and/or in-surgical procedural step. For example, during a manage major vessels procedural step, as shown in FIG. 24B., patient biomarker measurements associated with connective tissue thickness may be compared against a connective tissue thickness value to determine the ligation height. The value may be used to identify risks associated with a pre-surgical and/or in-surgical procedural step. For example, during manage major vessels procedural step, a patient's lung tissue strength may be compared against a lung tissue strength value (e.g., for identifying the risk of air leak). The value may be used to determine operational parameters for various surgical tools. During manage major vessels procedural step, a patient's blood pressure may be compared against a blood pressure value to determine the operational parameters of a harmonic scalpel. For example, the intensity of the harmonic scalpel may decrease when the patient's blood pressure crosses the blood pressure value.

Multiple post-op patient biomarker measurements may be compared against multiple pre-surgical and/or in-surgical values simultaneously or at different time intervals. In an example, post-op patient biomarker measurements may increase or decrease the pre-surgical and/or in-surgical values.

The invention claimed is:

1. A computing system comprising a processor configured to at least:

determine a first threshold associated with a first thoracic post-surgical patient biomarker associated with a patient, wherein the first thoracic post-surgical patient biomarker is associated with a thoracic post-surgical complication;

determine a second threshold associated with a second thoracic post-surgical patient biomarker associated with the patient, wherein the second thoracic post-surgical patient biomarker is associated with the thoracic post-surgical complication;

obtain a first post-surgical measurement data associated with the first thoracic post-surgical patient biomarker and a second post-surgical measurement data associated with the second thoracic post-surgical patient biomarker, wherein the first post-surgical measurement data is received from a first wearable sensing system and the second post-surgical measurement data is received from a second wearable sensing system;

monitor the first post-surgical measurement data and the second post-surgical measurement data, in real-time, for an amount of time by comparing the first post-surgical measurement data against the first threshold and comparing the second post-surgical measurement data against the second threshold;

predict the thoracic post-surgical complication based on the monitoring of the first post-surgical measurement data and the second post-surgical measurement data; and based on the prediction of the thoracic post-surgical complication, generate a real-time notification wherein the real-time notification is configured to indicate the predicted thoracic post-surgical complication when the first post-surgical measurement data crosses the first threshold or the second post-surgical measurement data crosses the second threshold, and send a control program to a controllable device to alter at least one operating parameter of a chest tube system associated with the patient.

2. The computing system of claim 1, wherein the processor is further configured to:

determine a severity level associated with the thoracic post-surgical complication based on the first post-surgical measurement data; and determine, based on the determined severity level, a notification type associated with the real-time notification.

3. The computing system of claim 2, wherein:

on a condition that the determined severity level is low, the processor is configured to send the real-time notification and the severity level to a display for displaying to the patient; and on a condition that the determined severity level is high, the processor is configured to send the real-time notification and the severity level to a display for displaying to a health care professional (HCP).

4. The computing system of claim 1, wherein the processor is further configured to:

obtain a context associated with setting the first threshold or the second threshold to be used for comparing the first post-surgical measurement data or the second post-surgical measurement data, wherein the context is based on at least one of a thoracic surgery recovery timeline, at least one situational attribute, a baseline data associated with the patient, or at least one environmental attribute; and adjust the first threshold or the second threshold based on the obtained context.

5. The computing system of claim 4, wherein comparing the first post-surgical measurement data against the adjusted first threshold is based on the context.

6. The computing system of claim 4, wherein the monitoring of the second post-surgical measurement data is based on a condition that the first post-surgical measurement data crosses the first threshold for a predetermined amount of time.

7. The computing system of claim 1, wherein the processor being configured to predict the thoracic post-surgical complication comprises the processor being configured to predict the thoracic post-surgical complication based on a patient prediction model.

8. The computing system of claim 1, wherein the thoracic post-surgical complication is a lung collapse, wherein one of the first thoracic post-surgical patient biomarker or the second thoracic post-surgical patient biomarker is a rate of change in patient's Oxygen saturation, a rate of change in patient's blood pressure, or a rate of change in patient's heart rate.

9. The computing system of claim 1, wherein the thoracic post-surgical complication is a prolonged air leak (PAL), wherein the PAL is determined by measuring at least one of the following: an air volume, a respiratory rate, a diaphragmatic muscle tone, or a phase of respiration.

10. The computing system of claim 1, wherein the first patient thoracic post-surgical biomarker is a phase of respiration and the second thoracic post-surgical patient biomarker is a diaphragmatic muscle tone, wherein the processor is further configured to send the control program to modulate a suction level of the chest tube system, wherein the suction level is modulated based at least one or more of the first post-surgical measurement data associated with the phase of respiration or the second post-surgical measurement data associated with the diaphragmatic muscle tone.

11. The computing system of claim 1, wherein the comparing is performed by accounting for an amount of lung volume reduction.

12. The computing system of claim 1, wherein the processor is further configured to:

generate an actionable notification associated with the prediction of the thoracic post-surgical complication, wherein the actionable notification enables the patient or a healthcare provider (HCP) to perform at least one recommended action.

13. A sensing system comprising a processor configured to at least:

obtain a first threshold associated with a first thoracic post-surgical patient biomarker, wherein the first thoracic post-surgical patient biomarker is associated with a thoracic post-surgical complication;

obtain a second threshold associated with a second thoracic post-surgical patient biomarker, wherein the second thoracic post-surgical patient biomarker is associated with the thoracic post-surgical complication;

obtain a first post-surgical measurement data associated with the first thoracic post-surgical patient biomarker and a second post-surgical measurement data associated with the second thoracic post-surgical patient biomarker;

monitor the first post-surgical measurement data and the second post-surgical measurement data, in real-time, by comparing the first post-surgical measurement data against the first threshold and comparing the second post-surgical measurement data against the second threshold;

predict the thoracic post-surgical complication based on the monitoring; and based on the prediction of the thoracic post-surgical complication, generate a real-time notification wherein the real-time notification is configured to indicate the predicted thoracic post-surgical complication, when one or more of the first post-surgical measurement data crosses the first threshold or the second post-surgical measurement data crosses the second threshold, and send a control program to a controllable device to alter at least one operating parameter of a chest tube system associated with a patient.

14. The sensing system of claim 13, wherein the processor is further configured to:

receive a request for predicting the thoracic post-surgical complication based on the first post-surgical measurement data associated with the first thoracic post-surgical patient biomarker crossing the first threshold for a first predetermined amount of time or the second post-surgical measurement data associated with the second thoracic post-surgical patient biomarker crossing the second threshold for a second predetermined amount of time; and generate the real-time notification indicating the predicted thoracic post-surgical complication when the first post-surgical measurement data crosses the first threshold for the first predetermined amount of time or the second post-surgical measurement data crosses the second threshold for the second predetermined amount of time.

15. The sensing system of claim 13, wherein the processor is further being configured to predict the thoracic post-surgical complication comprises the processor being configured to predict the thoracic post-surgical complication based on a patient prediction model.

16. The sensing system of claim 13, wherein the processor is further configured to:

determine a severity level associated with the thoracic post-surgical complication based on at least one of the first post-surgical measurement data or the second post-surgical measurement data; and determine, based on the determined severity level, a notification type associated with the real-time notification.

17. The sensing system of claim 16, wherein;

on a condition that the determined severity level is low, the processor is configured to send the real-time notification and the severity level to a display for displaying to the patient; and on a condition that the determined severity level is high, the processor is configured to send the real-time notification and the severity level to a display for displaying to a health care professional (HCP).

18. The sensing system of claim 13, wherein the processor is further configured to:

determine a context associated with setting the first threshold or the second threshold to be used for comparing the first post-surgical measurement data or the second post-surgical measurement data, wherein the context is based on at least one of a thoracic surgery recovery timeline, at least one situational attribute, a baseline data associated with the patient, or at least one environmental attribute; and adjust the first threshold or the second threshold based on the determined context.

19. The sensing system of claim 18, wherein the at least one situational attribute comprises at least one of a physical mobility state or a sleeping state.

20. The sensing system of claim 13, wherein the thoracic post-surgical complication is a prolonged air leak (PAL), and wherein the first thoracic post-surgical patient biomarker or the second thoracic post-surgical patient biomarker is a rate of change in patient's Oxygen saturation, a rate of change in patient's blood pressure, a rate of change in patient's heart rate, a rate of air flow, or a rate of air volume.

\* \* \* \* \*